US012774304B2

(12) United States Patent
Osmulski et al.

(10) Patent No.: US 12,774,304 B2
(45) Date of Patent: Oct. 27, 2026

(54) PEPTIDE-BASED COMPOSITIONS AND METHODS FOR TREATING ALZHEIMER'S DISEASE

(71) Applicant: Board of Regents, The University of Texas System, Austin, TX (US)

(72) Inventors: Pawel A. Osmulski, San Antonio, TX (US); Maria Gaczynska, San Antonio, TX (US); Andrew Pickering, San Antonio, TX (US); Przemyslaw Karpowicz, Gdansk (PL); Elzbieta Jankowska, Gdansk (PL)

(73) Assignee: Board of Regents, The University of Texas System, Austin, TX (US)

( * ) Notice: Subject to any disclaimer, the term of this patent is extended or adjusted under 35 U.S.C. 154(b) by 1176 days.

(21) Appl. No.: 17/642,499

(22) PCT Filed: Sep. 11, 2020

(86) PCT No.: PCT/US2020/050428
§ 371 (c)(1),
(2) Date: Mar. 11, 2022

(87) PCT Pub. No.: WO2021/050890
PCT Pub. Date: Mar. 18, 2021

(65) Prior Publication Data

US 2022/0332758 A1 Oct. 20, 2022

Related U.S. Application Data

(60) Provisional application No. 62/900,217, filed on Sep. 13, 2019.

(51) Int. Cl.
*A61P 25/28* (2006.01)
*C07K 5/083* (2006.01)
*C07K 7/02* (2006.01)

(52) U.S. Cl.
CPC ................ *C07K 7/02* (2013.01); *A61P 25/28* (2018.01); *C07K 5/0808* (2013.01)

(58) Field of Classification Search
CPC .......... C07K 7/02; C07K 5/0808; A61P 25/28
See application file for complete search history.

(56) References Cited

U.S. PATENT DOCUMENTS

2004/0048347 A1 3/2004 Lorbert et al.
2013/0266634 A1 10/2013 Lin et al.
2017/0298108 A1* 10/2017 Kalvakolanu ........ C12Q 1/6886

OTHER PUBLICATIONS

Costa_et_al_JBC_vol. 286_No. 48_Dec. 2011_pp. 41647-41655 (Year: 2011).*
Sharma_et_al_European_J_of_Pham_vol. 815_2017_pp. 312-323 (Year: 2017).*
Adams, J. "The proteasome: A suitable antineoplastic target." Nat. Rev. Cancer. 2004, 4, 349-360.
Almeida, C. G., et al. "Beta-amyloid accumulation impairs multivesicular body sorting by inhibiting the ubiquitin-proteasome system." J Neurosci. 26, 4277-4288 (2006).
Asano, S., et al. "A molecular census of 26S proteasomes in intact neurons." Science 2015, 347, 439-442.
Bahr, B. A. et al. "Amyloid beta protein is internalized selectively by hippocampal field CA1 and causes neurons to accumulate amyloidogenic carboxyterminal fragments of the amyloid precursor protein." J Comp Neurol 397, 139-147 (1998).
Bedford, L. et al. "Depletion of 26S proteasomes in mouse brain neurons causes neurodegeneration and Lewy-like inclusions resembling human pale bodies." J Neurosci 28, 8189-8198 (2008).
Besse, A., et al. "Proteasome Inhibition in Multiple Myeloma: Head-to-Head Comparison of Currently Available Proteasome Inhibitors." Cell Chem Biol. 2019, 26, 340-351.
Boland B, et al. "Promoting the clearance of neurotoxic proteins in neurodegenerative disorders of ageing." Nat Rev Drug Discov. Aug. 17, 2018;17:660.
Brookmeyer R, et al. "Forecasting the global burden of Alzheimer's disease." Alzheimer's Dement. Jul. 2007;3(3):186-191.
Burgess K. "Solid-phase syntheses of beta-turn analogues to mimic or disrupt protein-protein interactions." Acc Chem Res. Oct. 2001;34(10):826-835.
Butterfield, D. A., et al. "In vivo oxidative stress in brain of Alzheimer disease transgenic mice: Requirement for methionine 35 in amyloid beta-peptide of APP." Free Radic Biol Med 48, 136-144 (2010).
Chakravarty S, et al. "Design of potent, cyclic peptide bradykinin receptor antagonists from conformationally constrained linear peptides." J Med Chem. Aug. 20, 1993;36(17):2569-71.
Chen, S., et al. "Structural basis for dynamic regulation of the human 26S proteasome." Proc Natl Acad Sci U S A. 2016, 113, 12991-12996.
Cheng, I. H. et al. "Accelerating amyloid-beta fibrillization reduces oligomer levels and functional deficits in Alzheimer disease mouse models." J Biol Chem 282, 23818-23828 (2007).
Chondrogianni, N. and Gonos, E.S. "Proteasome dysfunction in mammalian aging: Steps and factors involved." Exp. Gerontol. 2005, 40, 931-938.
Chondrogianni, N. et al. "Overexpression of proteasome beta5 assembled subunit increases the amount of proteasome and confers ameliorated response to oxidative stress and higher survival rates." J Biol Chem 280, 11840-11850 (2005).

(Continued)

*Primary Examiner* — Catherine S Hibbert
(74) *Attorney, Agent, or Firm* — BALLARD SPAHR LLP

(57) ABSTRACT

Disclosed herein, are peptides capable of activating proteasome activity, and pharmaceutical compositions containing the peptides and methods treating Alzheimer's disease. Disclosed herein are compositions comprising: A) a peptide, wherein the peptide comprises the amino acid sequence GRKKR-RQ-AibG-RPS (SEQ ID NO: 4), or a fragment or variant thereof, B) a peptide, wherein the peptide comprises the amino acid sequence GRKKRRQ-AibG-QR-RKKRG (SEQ ID NO: 5), or a fragment or variant thereof, or C) a peptide, wherein the peptide comprises the amino acid sequence KKK/KKK-DABA-K KK (SEQ ID NO: 6) or a fragment or variant thereof.

12 Claims, 22 Drawing Sheets

Specification includes a Sequence Listing.

(56) References Cited

OTHER PUBLICATIONS

Chondrogianni, N., et al."20S proteasome activation promotes life span extension and resistance to proteotoxicity in Caenorhabditis elegans." Faseb J 29, 611-622 (2015).
Chu, J., et al. "Degradation of gamma secretase activating protein by the ubiquitin-proteasome pathway." J Neurochem 133, 432-439 (2015).
Coleman, R.A., et al. "Analysis of chain length, substitution patterns, and unsaturation of AM-404 derivatives as 20S proteasome stimulators." Bioorg Med. Chem Lett. 2019, 29, 420-423.
Coleman, R.A. and Trader, D.J. "Methods to Discover and Evaluate Proteasome Small Molecule Stimulators." Molecules. 2019, 24, 2341.
Cummings J, et al. "Alzheimer's disease drug development pipeline: 2018." Alzheimer's Dement Transl Res Clin Interv; 2018;4:195-214.
Dong, Y., et al. "Cryo-EM structures and dynamics of substrate-engaged human 26S proteasome." Nature 2019, 565, 49-55.
Forster, A., et al. "The pore of activated 20S proteasomes has an ordered 7-fold symmetric conformation." EMBO J. 2003, 22, 4356-4364.
Gaczynska, M. and Osmulski, P.A. "Targeting Protein-Protein Interactions in the Ubiquitin-Proteasome Pathway. in: Advances in Protein Chemistry and Structural Biology. Protein-Protein Interactions in Human Disease, Part A." Elsevier Inc.; Amsterdam, Netherlands, 2018, 123-165.
Gaczynska, M. and Osmulski, P.A. "Harnessing proteasome dynamics and allostery in drug design." Antioxidants Redox Signal. 2014, 21, 2286-2301.
Galvan, V. et al. "Reversal of Alzheimer's-like pathology and behavior in human APP transgenic mice by mutation of Asp664." Proc Natl Acad Sci U S A 103, 7130-7135 (2006).
Giletto, M.B., et al. "Pipecolic esters as minimized templates for proteasome inhibition." Org. Biomol Chem. 2019, 17, 2734-2746.
Giżyńska, M., et al. "Proline- and Arginine-Rich Peptides as Flexible Allosteric Modulators of Human Proteasome Activity." J. Med. Chem. 2019, 62, 359-370.
Greenfield, J. P. et al. "Endoplasmic reticulum and trans-Golgi network generate distinct populations of Alzheimer beta-amyloid peptides." Proc Natl Acad Sci U S A 96, 742-747 (1999).
Gronenberg, W. & Lopez-Riquelme, G. O. "Multisensory convergence in the mushroom bodies of ants and bees." Acta Biol Hung 55, 31-37, (2004).
Heinemeyer, W., et al. "The active sites of the eukaryotic 20 S proteasome and their involvement in subunit precursor processing." J Biol Chem 272, 25200-25209 (1997).
Hicks RP. "Antibacterial and anticancer activity of a series of novel peptides incorporating cyclic tetra-substituted C(α) amino acids." Bioorg Med Chem. 2016;24(18):4056-4065.
Hong, S. et al. "Complement and microglia mediate early synapse loss in Alzheimer mouse models." Science 352, 712-716 (2016).
Hsia, A. Y. et al. "Plaque-independent disruption of neural circuits in Alzheimer's disease mouse models." Proc Natl Acad Sci U S A 96, 3228-3233 (1999).
Huang, X. et al. "The RTP site shared by the HIV-1 Tat protein and the 11S regulator subunit alpha is crucial for their effects on proteasome function including antigen processing." J Mol Biol 323, 771-782 (2002).
Huang, L. et al. "Activation and inhibition of the proteasome by betulinic acid and its derivatives." FEBS Lett. 2007, 581, 4955-4959.
Jankowska E, et al. "Potential allosteric modulators of the proteasome activity." Biopolymers. 2010;93(5):481-495.
Jankowska, E et al. "The proteasome in health and disease." Curr Pharm Des. 2013, 19, 1010-1028.
Jeang, K.-T., et al. "Multifaceted Activities of the HIV-1 Transactivator of Transcription, Tat." J. Biol Chem. 1999, 274, 28837-28840.
Jones, C.L. and Tepe, J.J. "Proteasome Activation to Combat Proteotoxicity." Molecules. 2019, 24, 2841.
Jones, C.L., et al. "Small Molecule Enhancement of 20S Proteasome Activity Targets Intrinsically Disordered Proteins." ACS Chem Biol. 2017, 12, 2240-2247.
Karpowicz, et al. "Interplay between Structure and Charge as a Key to Allosteric Modulation of Human 20S Proteasome by the Basic Fragment of HIV-1 Tat Protein," PLoS One, Nov. 17, 2015, vol. 10, Issue 11, pp. 1-25.
Keck, S., et al. "Proteasome inhibition by paired helical filament-tau in brains of patients with Alzheimer's disease." J Neurochem 85, 115-122 (2003).
Keller, J. N., et al. "Impaired proteasome function in Alzheimer's disease." J Neurochem 75, 436-439 (2000).
Kisselev, A.F., et al. "Binding of hydrophobic peptides to several non-catalytic sites promotes peptide hydrolysis by all active sites of 20 S proteasomes-Evidence for peptide-induced channel opening in the alpha-rings." J. Biol Chem. 2002, 277, 22260-22270.
Kyle DJ, et al. "Probing the bradykinin receptor: mapping the geometric topography using ethers of hydroxyproline in novel peptides." J Med Chem Aug. 1991;34(8):2649-53.
Laferla, F. M., et al. "Intracellular amyloid-beta in Alzheimer's disease." Nat Rev Neurosci 8, 499-509 (2007).
Larregola M, et al. "β-Amino acids containing peptides and click-cyclized peptide as β-turn mimics: a comparative study with 'conventional' lactam- and disulfide-bridged hexapeptides." J Pept Sci 2011;17(9):632-643.
Lata, S., et al. "Proteasomal Degradation Machinery: Favorite Target of HIV-1 Proteins." Front. Microbiol. 2018, 9, 2738.
Lee B-H, et al. "Enhancement of proteasome activity by a small-molecule inhibitor of USP14." Nature Sep. 2010;467(7312):179-184.
Linford, N. J., et al. "Measurement of lifespan in *Drosophila melanogaster*." J Vis Exp, 71:50068 (2013).
Malik, B. R. & Hodge, J. J. "*Drosophila* adult olfactory shock learning." J Vis Exp, e50107 (2014).
Mcnaught, K.S., et al. "Selective loss of 20S proteasome α-subunits in the substantia nigra pars compacta in Parkinson's disease." Neurosci Lett. 2002, 326, 155-158.
Mi, J. et al. "A genetically encoded reporter for real-time imaging of cofilin-actin rods in living neurons." PLoS One 8, e83609 (2013).
Morris, R. "Developments of a water-maze procedure for studying spatial learning in the rat." J Neurosci Methods 11, 47-60 (1984).
Mucke, L. et al. "High-level neuronal expression of abeta 1-42 in wild-type human amyloid protein precursor transgenic mice: synaptotoxicity without plaque formation." J Neurosci 20, 4050-4058 (2000).
Munkacsy, E. et al. "Neuronal-specific proteasome augmentation via Prosβ5 overexpression extends lifespan and reduces age-related cognitive decline." Aging Cell, e13005 (2019).
Myeku N and Duff KE. "Targeting the 26S Proteasome To Protect Against Proteotoxic Diseases." Trends Mol Med; Jan. 11, 2018;24(1):18-29.
Nguyen, N. N. et al. "Proteasome β5 subunit overexpression improves proteostasis during aging and extends lifespan in *Drosophila melanogaster*." Sci Rep 9, 3170 (2019).
Njomen, E. and Tepe, J.J. "Proteasome Activation as a New Therapeutic Approach To Target Proteotoxic Disorders." J. Med. Chem. 2019, 62, 6469-6481.
Njomen, E., et al. "Small Molecule Modulation of Proteasome Assembly." Biochemistry. 2018, 57, 4214-4224.
Nunan, J. et al. "Proteasome-mediated degradation of the C-terminus of the Alzheimer's disease beta-amyloid protein precursor: effect of C-terminal truncation on production of beta-amyloid protein." J Neurosci Res 74, 378-385 (2003).
Ortega, J., et al. "The axial channel of the 20S proteasome opens upon binding of the PA200 activator." J. Mol. Biol. 2005, 346, 1221-1227.
Osmulski, P.A. and Gaczynska, M. "Rapamycin allosterically inhibits the proteasome." Mol. Pharmacol. 2013, 84, 104-113.
Osmulski, et al. "New Peptide-Based Pharmacophore Activates 20S Proteasome," Molecules, Mar. 22, 2020, vol. 26, Issue 6, pp. 1-17.
Osmulski, P.A. and Gaczynska, M. "Nanoenzymology of the 20S proteasome: Proteasomal actions are controlled by the allosteric transition." Biochemistry. 2002, 41, 7047-7053.

(56) References Cited

OTHER PUBLICATIONS

Osmulski, P.A., et al. "Tetrahedral Transition State at the Active Sites of the 20S Proteasome Is Coupled to Opening of the α-Ring Channel." Structure. 2009, 17, 1137-1147.
Peth A, et al. "Ubiquitinated proteins activate the proteasome by binding to Usp14/Ubp6, which causes 20S gate opening." Mol Cell. Dec. 2009;36(5):794-804.
Pierce, A. et al. "Over-expression of heat shock factor 1 phenocopies the effect of chronic inhibition of TOR by rapamycin and is sufficient to ameliorate Alzheimer's-like deficits in mice modeling the disease." J Neurochem 124, 880-893 (2013).
Qing, H. et al. "Degradation of BACE by the ubiquitin-proteasome pathway." Faseb J 18 (21 Pages) (2004).
Rana, T.M., et al. "Biochemical and Functional Interactions between HIV-1 Tat Protein and TAR RNA." Arch. Biochem Biophys. 1999, 365, 175-185.
Ray, A. S. "Intracellular interactions between nucleos(t)ide inhibitors of HIV reverse transcriptase." AIDS Rev 7, 113-125 (2005).
Ren, C., et al. "Conditional inhibition of autophagy genes in adult *Drosophila* impairs immunity without compromising longevity." Exp Gerontol 44, 228-235 (2009).
Roberson, E. D. et al. "Reducing endogenous tau ameliorates amyloid beta-induced deficits in an Alzheimer's disease mouse model." Science 316, 750-754 (2007).
Rodriguez, K.A., et al. "Molecular mechanisms of proteasome plasticity in aging." Mech Ageing Dev. 2010, 131, 144-155.
Romero-Granados, R., et al. "Postnatal proteasome inhibition induces neurodegeneration and cognitive deficiencies in adult mice: a new model of neurodevelopment syndrome." PLoS One 6, e28927 (2011).
Rosen, K. M. et al. "Parkin reverses intracellular beta-amyloid accumulation and its negative effects on proteasome function." Journal of Neuroscience Research 88, 167-178 (2010).
Rubinsztein, D.C. "The roles of intracellular protein-degradation pathways in neurodegeneration." Nature. 2006, 443, 780-786.
Saganich, M. J. et al. "Deficits in synaptic transmission and learning in amyloid precursor protein (APP) transgenic mice require C-terminal cleavage of APP," J Neurosci 26, 13428-13436 (2006).
Schlasner KN, et al. "Structure-Activity Relationships of the Tetrapeptide Ac-His-Arg-( p I)DPhe-Tic-NH2 at the Mouse Melanocortin Receptors: Modification at the ( p I)DPhe Position Leads to mMC3R Versus mMC4R Selective Ligands." Molecules. MDPI; Apr. 13, 2019;24(8):1463.
Schrader, J. et al. "The inhibition mechanism of human 20S proteasomes enables next-generation inhibitor design." Science 2016, 353, 594 (30 Pages).
Schwarze, S.R., et al. "Protein transduction: Unrestricted delivery into all cells?" Trends Cell Biol.2000, 10, 290-295.
Schweitzer, A., et al. "Structure of the human 26S proteasome at a resolution of 3.9 Å." Proc. Natl. Acad. Sci. 2016, 113, 7816-7821.
Shringarpure, R., et al. "4-Hydroxynonenal-modified amyloid-beta peptide inhibits the proteasome: possible importance in Alzheimer's disease." Cell Mol Life Sci 57, 1802-1809 (2000).
Skorupa, D. A., et al. "Dietary composition specifies consumption, obesity, and lifespan in *Drosophila melanogaster*." Aging Cell 7, 478-490 (2008).
Smith, D.M., et al. "Docking of the proteasomal ATPases' carboxyl termini in the 20S proteasome's alpha ring opens the gate for substrate entry." Mol. Cell. 2007, 27, 731-744.
Sopher, B. L., et al. "Neurodegenerative mechanisms in Alzheimer disease. A role for oxidative damage in amyloid beta protein precursor-mediated cell death." Mol Chem Neuropathol 29, 153-168 (1996).
Staudt, N. et al. "Gain-of-function screen for genes that affect *Drosophila* muscle pattern formation." PLoS Genet 1, e55 (2005).
Tanahashi, N., et al. "Hybrid Proteasomes." J. Biol Chem. 2000, 275, 14336-14345.
Tanaka, K., et al. "The proteasome: Molecular machinery and pathophysiological roles." Biol Chem. 2012, 393, 217-234.
Toste Rêgo, A. and Da Fonseca, P.C.A. "Characterization of Fully Recombinant Human 20S and 20S-PA200 Proteasome Complexes." Mol. Cell 2019, 76, 138-147.
Upadhya, S. C. & Hegde, A. N. "Role of the ubiquitin proteasome system in Alzheimer's disease." BMC biochemistry 8 Suppl 1, S12 (2007).
Vakser, I.A. "Long-distance potentials: An approach to the multiple-minima problem in ligand-receptor interaction." Protein Eng. Des. Sel. 1996, 9, 37-41.
Vakser, I.A. "Protein-Protein Docking: From Interaction to Interactome." Biophys, J. 2014, 107, 1785-1793.
Wakata, A., et al. "Simultaneous Fluorescent Monitoring of Proteasomal Subunit Catalysis." J. Am. Chem Soc. 2010, 132, 1578-1582.
Whitby, F.G., et al. "Structural basis for the activation of 20S proteasomes by 11S regulators." Nature 2000, 408, 115-120.
Wilkes BC and Schiller PW. "Theoretical conformational analysis of the opioid delta antagonist H-Tyr-Tic-Phe-OH and the mu agonist H-Tyr-D-Tic-Phe-NH2." Biopolymers. Sep. 1994;34(9):1213-1219.
Witkowska, J., et al. "Crystal structure of a low molecular weight activator Blm-pep with yeast 20S proteasome-insights into the enzyme activation mechanism." Sci Rep. 2017, 7, 6177.
Witkowska, J., et al. "Dissecting a role of a charge and conformation of Tat2 peptide in allosteric regulation of 20S proteasome." J Pept Sci 20 (8 Pages) (2014).
Wright, A. L. et al. "Neuroinflammation and neuronal loss precede Aβ plaque deposition in the hAPP-J20 mouse model of Alzheimer's disease." PLoS One 8, e59586 (2013).
Yoshimura, T., et al. "Molecular Characterization of the "26S" Proteasome Complex from Rat Liver." J. Struct Biol. 1993, 111, 200-211.
International Search Report and Written Opinion were mailed on Dec. 31, 2020 by the International Searching Authority for International Application No. PCT/US2020/050428, filed on Sep. 11, 2020 and published as WO/2021/050890 on Mar. 18, 2021 (Applicant-Board of Regents, The University of Texas System) (13 Pages).
Choi, Sunghyun, et al., "Protective Effect of Tag PTD-Hsp27 Fusion Protein on Tau Hyperphorylation Induced by Okadaic Acid in the Human Neuroblastoma Cell Line SH-SY5Y," Cellular and Molecular Neurobiology, 35(7):1049-1059 (2015), XP035547867.
Supplementary European Search Report mailed Dec. 14, 2023 for European Patent Application No. 20862490.8, based on International Patent Application No. PCT/US2020/050428, 13 Pages.

* cited by examiner

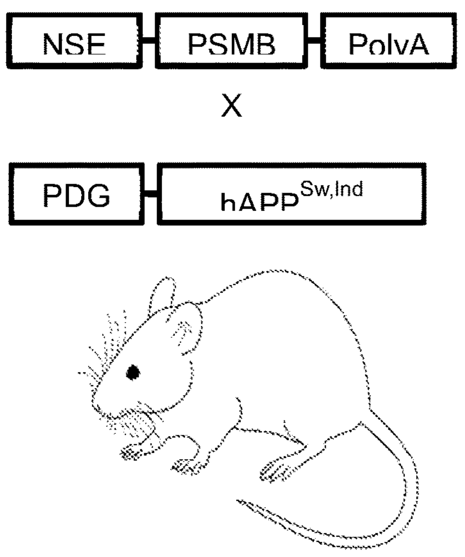
Fig. 2G
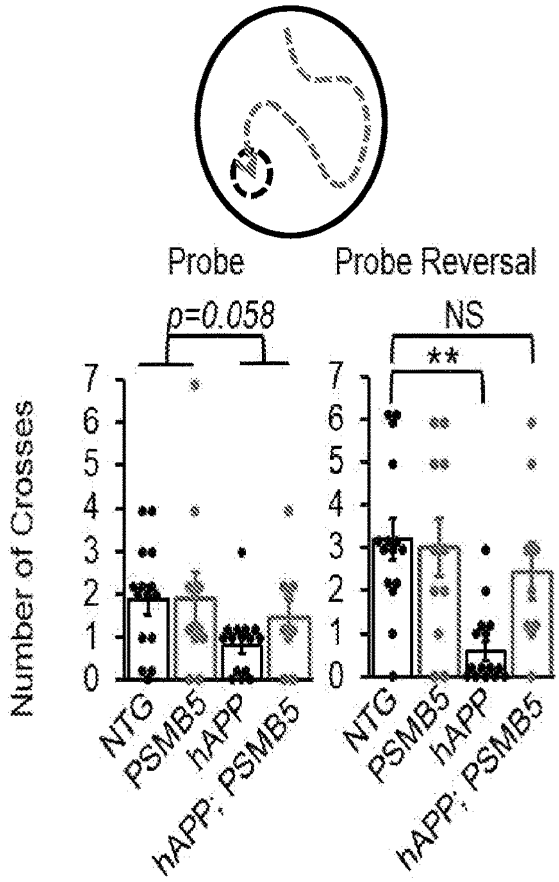
Fig. 2H
Fig. 2I
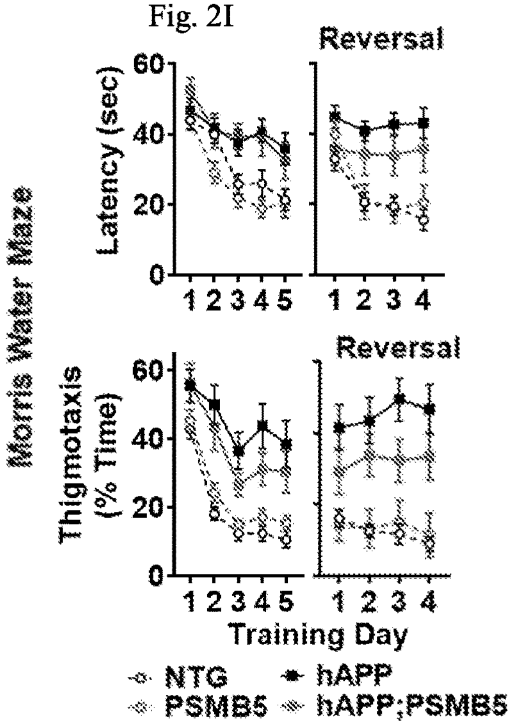
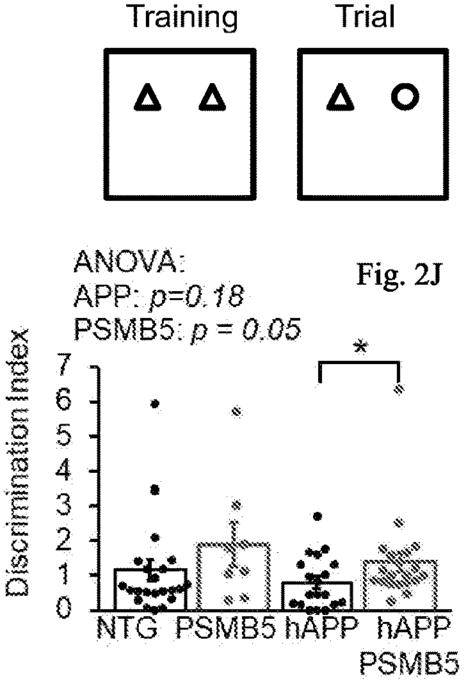
Fig. 2J

| Name | Sequence | SEQ ID NO: | Structure |
|---|---|---|---|
| Tat1 | GRKKRRQRR<br>RPS | 1 |  |
| Tat1 8,9<br>TOD | GRKKRRQ-<br>TOD-RPS | 3 |  |
| Tat1-<br>Dendrite | KKK<br>\<br>KKK-DABA-<br>-KKK | 6 |  |

| | | | |
|---|---|---|---|
| Tat1 8,9 Aib | GRKKRRQ-AibG-RPS | 4 |  |
| Tat5 8,9 Aib | GRKKRRQ-AibG-QRRKKRG | 5 |  |

Tat1-8,9TOD $t_{1/2}$ = 136.4 ± 0.46 min

| | |
|---|---|
| Model<br>Equation | ExpDecay1<br>y = y0 + A1*exp(-(x-x |
| Plot | Mean |
| y0 | -0.06366 ± 0.8073 |
| x0 | -0.74873 ± 1.88326 |
| A1 | 99.83239 |
| t1 | 198.69892 ± 4.24294 |
| Reduced Chi-S | 0.62497 |
| R-Square (CO | 0.99956 |
| Adj. R-Square | 0.99938 |

PEPTIDE-BASED COMPOSITIONS AND METHODS FOR TREATING ALZHEIMER'S DISEASE

CROSS-REFERENCE TO RELATED APPLICATIONS

This application is a national phase application under 35 U.S.C. § 371 of International Application No. PCT/US2020/050428, filed Sep. 11, 2020 and claims the benefit of the filing date of U.S. Provisional Application No. 62/900,217, filed Sep. 13, 2019. The content of these earlier filed applications is hereby incorporated by reference in its entirety.

STATEMENT REGARDING FEDERALLY FUNDED RESEARCH

This invention was made with government support under grant number AG061051 awarded by the National Institutes of Health. The government has certain rights in the invention.

INCORPORATION OF THE SEQUENCE LISTING

The present application contains a sequence listing containing the file name "21105_0073U2. txt" which is 12,288 bytes in size, created on Mar. 16, 2026 and is herein incorporated by reference in its entirety pursuant to 37 C.F.R. § 1.52(e)(5).

BACKGROUND

Alzheimer's disease (AD) is a massive global health problem affecting the rapidly growing aging population in U.S. and in the developed world. Drugs effectively preventing the devastating progression of Alzheimer's disease will be of immediate use in patients with preclinical as well as symptomatic Alzheimer's disease. The forecast is that in 2050 more than 1% of the global population will be living with Alzheimer's disease (Brookmeyer R, Johnson E, Ziegler-Graham K, Arrighi H M. Forecasting the global burden of Alzheimer's disease. Alzheimer's Dement [Internet]. 2007 July; 3(3):186-191). Importantly, it has been estimated that a one-year delay in the onset of Alzheimer's disease by 2020 would translate into 9 million fewer cases in 2050: a huge reduction in health care costs (Brookmeyer R, Johnson E, Ziegler-Graham K, Arrighi H M. Forecasting the global burden of Alzheimer's disease. Alzheimer's Dement [Internet]. 2007 July; 3(3):186-191). Thus, a need exists for new therapeutic strategies for treating Alzheimer's disease.

SUMMARY

Disclosed herein are compositions comprising:

A) a peptide, wherein the peptide comprises the amino acid sequence GRKKRRQ-AibG-RPS (SEQ ID NO: 4), or a fragment or variant thereof;

B) a peptide, wherein the peptide comprises the amino acid sequence GRKKRRQ-AibG-QRRKKRG (SEQ ID NO: 5), or a fragment or variant thereof; or C) a peptide, wherein the peptide comprises the amino acid sequence KKK KKK-DABA-KKK (SEQ ID NO: 6) or a fragment or variant thereof.

Disclosed herein are compounds having a structure represented by a formula (Tat1 8,9 TOD; SEQ ID NO: 3):

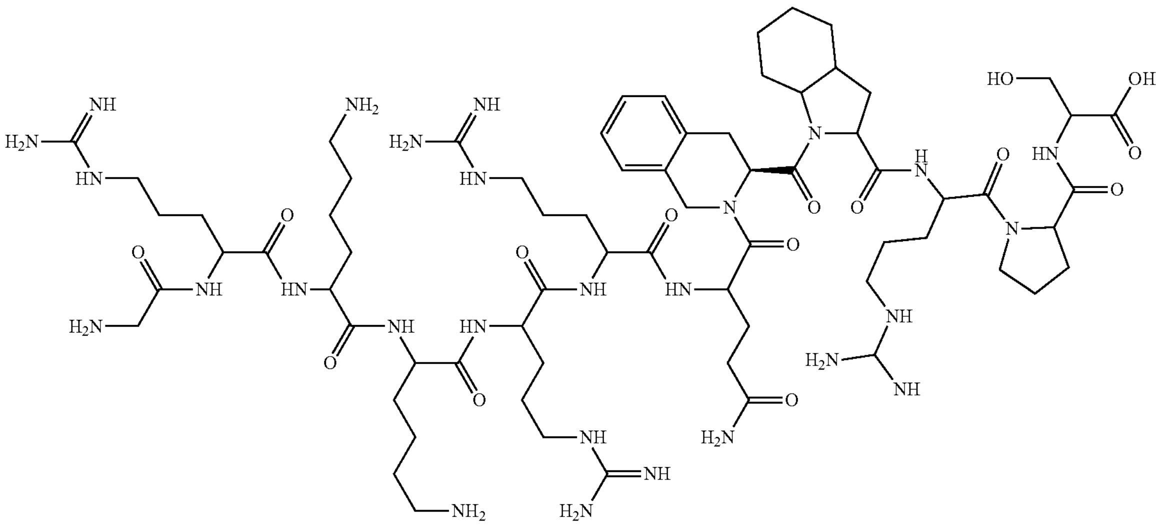 [SMILES: N=C(N)NCCCC(NC(=O)CN)C(=O)NC(CCCCN)C(=O)NC(CCCCN)C(=O)NC(CCCNC(=N)N)C(=O)NC(CCCNC(=N)N)C(=O)NC(CCC(N)=O)C(=O)N1Cc2ccccc2C[C@H]1C(=O)N1C(C(=O)NC(CCCNC(N)N)C(=O)N2CCCC2C(=O)NC(CO)C(=O)O)CC2CCCCC21]

or a pharmaceutically acceptable salt thereof.

Disclosed herein are compounds having a structure represented by a formula (Tat1 8,9 Aib; SEQ ID NO: 4):
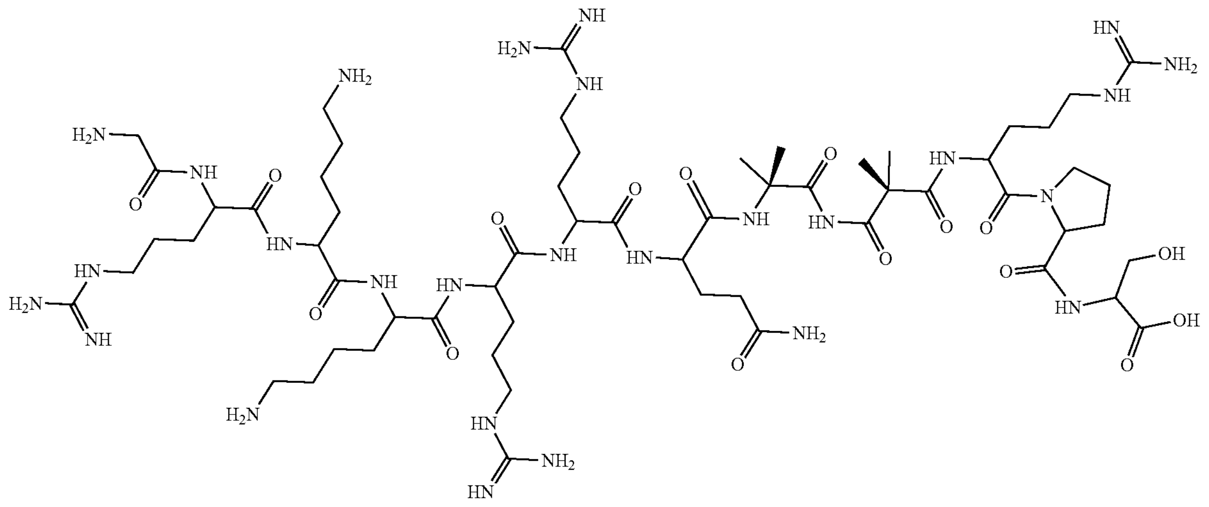
or a pharmaceutically acceptable salt thereof.
Disclosed herein are compounds having a structure represented by a formula (Tat5 8,9 Aib; SEQ ID NO: 5):

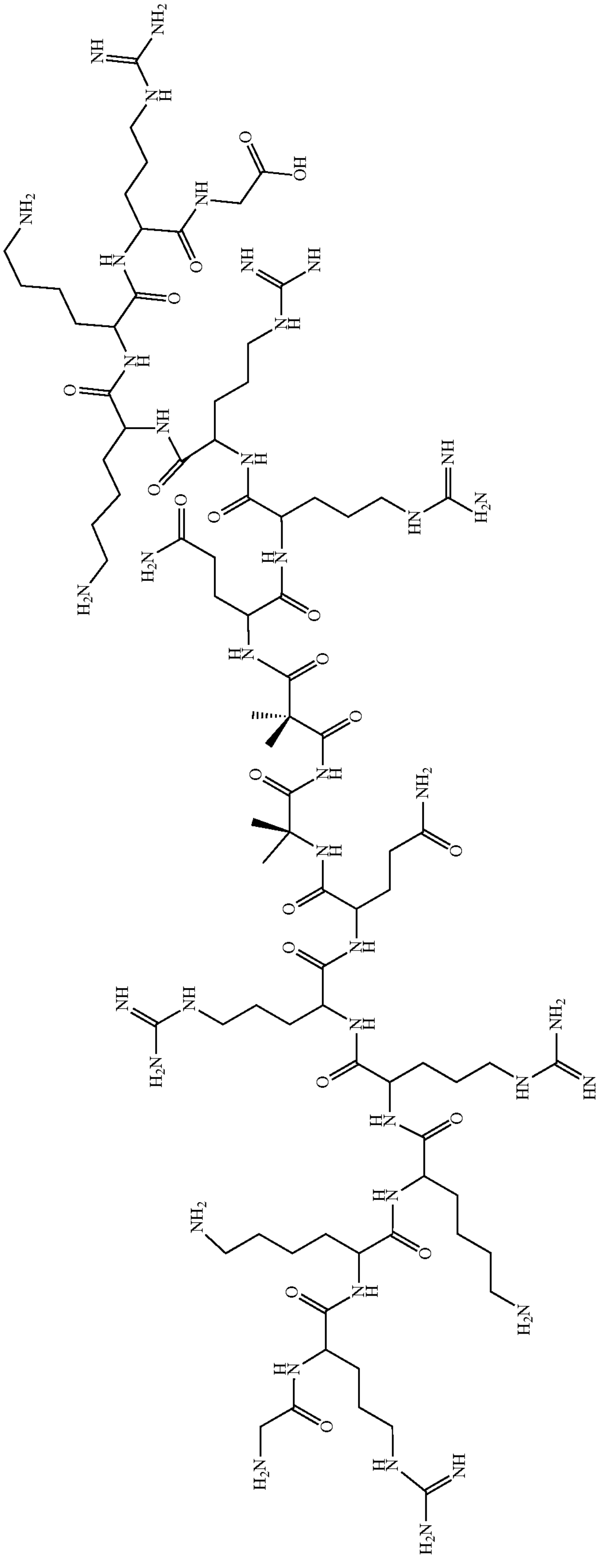

or a pharmaceutically acceptable salt thereof.

Disclosed herein are compounds having a structure represented by a formula (Tat1-Dendrite; SEQ ID NO: 6):

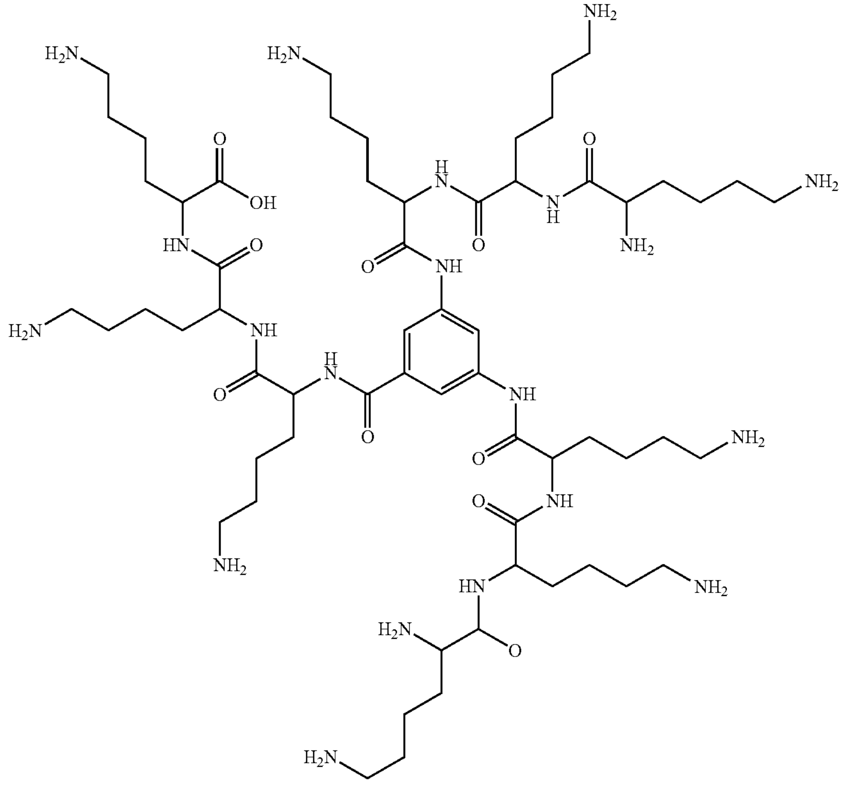 [SMILES: NCCCCC(N)C(=O)NC(CCCCN)C(=O)NC(CCCCN)C(=O)Nc1cc(NC(=O)C(CCCCN)NC(=O)C(CCCCN)NC(O)C(N)CCCCN)cc(C(=O)NC(CCCCN)C(=O)NC(CCCCN)C(=O)NC(CCCCN)C(=O)O)c1]

or a pharmaceutically acceptable salt thereof.

Disclosed herein are Tat1 analogs with a beta-turn conformation at positions 4-5 and/or 8-9.

BRIEF DESCRIPTION OF THE DRAWINGS

FIG. 1A shows that proteasome (Chymotrypsin-like) activity impaired in Alzheimer's disease models, B103 cells treated with 1 μM Aβ42 (N=3), 20 day old Elav-GS-GAL4>UAS-AB3-42 flies (±200 μM RU486, N=12), 7 month old hAPP(J20) mice and NTG littermates (N=5-7). FIG. 1B shows that the fly AD model utilized in rest of this figure. FIG. 1C shows that Alzheimer's disease shortens fly lifespan by 12%, lifespan N=175, (C-inset) dissected brain stained with anti-Aβ. FIG. 1D shows that Alzheimer's disease produces deficits in olfaction aversion training and spontaneous activity N=150-200, day 30. FIG. 1E shows that proteasome overexpression (comparing Elav-GS-GAL4>UAS-APP; UAS-BACE1 (Alzheimer's disease) with Elav-GS-GAL4>UAS-APP; UAS-BACE1; UAS-Prosβ5 (AD w/Prosβ5)) prevents Alzheimer's disease induced proteasome activity deficits and chymoryptsin-like proteasome activity. Flies maintained in SY10 media under 400 μM RU486 until Day 30, N=8. FIG. 1F shows Alzheimer's disease deficits to lifespan restored with proteasome over-expression. N=250. (F-inset) Prosβ5 overexpression does not alter APP mRNA levels, N=8. FIG. 1G shows that proteasome overexpression partially overcomes Alzheimer's disease deficits in olfactory aversion training, 30 day old flies N=150. FIG. 1H shows that proteasome over-expression partially restores Alzheimer's disease-induced deficits in circadian rhythmicity. N=200 at 30 days of age.

FIGS. 2A-L shows PSMB5 overexpression increases proteasome function in mice and delays Alzheimer's disease-like cognitive deficits and mortality. FIG. 2A shows the NSE-PSMB5 transgene. FIG. 2B shows an immunoblot of PSMB5 normalized to β-actin, brains dissected from 3-month-old mice N=6-7. FIG. 2C shows qPCR, brains dissected from 3-month-old mice N=4-6. FIG. 2D shows proteasome activity, chymotrypsin-like, brains dissected from 3-month-old mice N=6-7. FIGS. 2E-F show that NSE-PSMB5 reduces Alzheimer's disease related cell death. Cell Survival (WST-1 assay) in MC65 Alzheimer's disease-like cell culture model transfected with NSE-PSMB5, 4 days after tetracycline withdrawal, N=24. FIG. 2G shows NSE-PSMB5 mice crossed with hAPP(J20) Alzheimer's disease model. FIGS. 2H-K show that NSE-PSMB5 reduces Alzheimer's disease-like learning & memory deficits in: Morris water maze, Y-maze and novel object recognition assay respectively. Animals were 7-8 months old and littermates. N=9-15. FIG. 2L shows that NSE-PSMB5 protects against early mortality in hAPP(J20) mice, N=37-55 animals are littermates.

FIGS. 3A-B show immunoblots of 70 day old Elav-GS-GAL4>UAS-hAPP; UAS-hBACE1 flies Elav-GS-GAL4>UAS-hAPP; UAS-hBACE1; UAS-Prosβ5 flies. Flies were fed 400 μM RU486 N=12. FIG. 3C shows an immunoblot of SK-N-SH cells transfected with either the NSE vector or NSE-PSMB5. N=3. FIG. 3D show an immunoblot of SK-N-SH cells transfected with either the NSE vector or NSE-PSMB5 along with $APP^{GFP}$. N=6. FIGS. 3E,F show immunoblots with DNA gel presented below N=4 hAPP(J20), 8 hAPP(J20); NSE-PSMB5. FIG. 3G shows AB42 Elisa N=4 hAPP(J20), 8 hAPP(J20); NSE-PSMB5.

FIG. 4A shows in vitro proteasome activity assays, TAT1-8,9TOD incubated with purified 20S/26S proteasome. FIG. 4B shows in vitro proteasome activity assays, TAT1-DEN incubated with purified 20S/26S proteasome. FIG. 4C shows that TAT1-8,9TOD and TAT1-DEN enhance proteasome activity when fed to flies, proteasome activity assays in $W^{1118}$ flies treated for 10 days with TAT1-8,9TOD and TAT1-DEN or vehicle, N=8. FIG. 4E shows the results of olfaction aversion training in Elav-gs-GAL4>UAS-APP; UAS-BACE1 flies treated for 10 days with 1 μM TAT1-8,9TOD or 1 μM TAT1-DEN mixed directly into food, N=65. FIG. 4F shows the results of the lifespan assay of Elav-gs-GAL4>UAS-APP, UAS-BACE1 flies treated with 0.25 μM TAT1-8,9TOD N=290-300. FIG. 4G shows neuroblasts cultured with TAT1-8,9TOD. FIG. 4H shows that treatment of MC65 cells with TAT1-8,9TOD reduces Alzheimer's disease related cell death, based on WST1 viability assay N=24. FIG. 4I show mice are treated with TAT1-8,9TOD by IP injection. FIG. 4J shows proteasome activity in CNS of non-transgenic mice, 24 h after IP injection with TAT1-8,9TOD. N=5. FIG. 4K shows the results of the novel object recognition assay in hAPP(J20) mice after 14 days IP injection with 1 mg/kg TAT1-8,9TOD or vehicle, N=5. FIG. 4L shows an immunoblot against Anti-APP and Anti-BACE1 and Aβ42 Elisa in hAPP(J20) mice after 14 treatment with TAT1-8,9TOD or vehicle, N=5.

FIG. 9A shows the crystal structure based model of the 20S catalytic core proteasome. Colored subunits of the tube-shaped core are arranged in four heptameric rings (αββα) that form the inner catalytic chamber and the outer "α face" equipped with a central gate for substrate uptake and product release. The pockets between α subunits are utilized to anchor 19S or other regulatory modules of the catalytic core. Based on Protein Data Bank structure pdb 5t0g [25]. FIG. 9B shows a scheme of HIV-1 Tat protein (SEQ ID NO: 1), with the domain required for transactivation [26,27] shaded blue and with the short fragment designated as TAT1 marked. FIG. 9C shows a reported molecular dynamics simulation of TAT1, suggesting a potential for formation of two turns (modified from [22,24]).

FIG. 14A shows the surface rendering of a fragment of the α face with (5) protruding from the pocket; below—α face with orange colored (5) and α1/α2. FIG. 14B shows the Zoom-in of proposed positioning of (5) in the binding pocket. FIG. 14C shows a schematic positioning of (5) in the α face binding pocket. FIG. 14D shows the molecular dynamics simulation of (5) (from [24]) with putative functional significance of the N-terminal and C-terminal fragments for interactions with the proteasome.

DETAILED DESCRIPTION

Figure 1A:
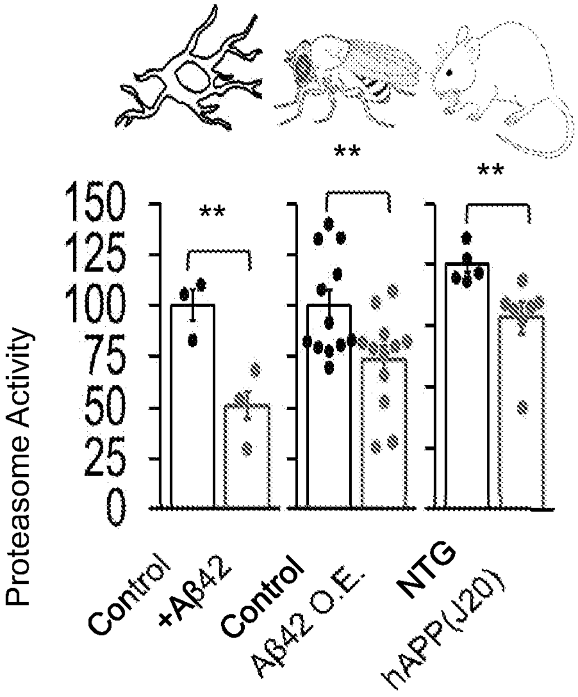
FIGS. 1A-H show that proteasome augmentation delays Alzheimer's disease-like mortality and cognitive deficit in flies.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if "about 10 and 15" are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition or at risk for a disease, disorder or condition. The term "patient" includes human and veterinary subjects. In some aspects of the disclosed methods, the "patient" has been diagnosed with a need for treatment, such as, for example, prior to an administering step.

As used herein, the term "comprising" can include the aspects "consisting of" and "consisting essentially of."

As used herein the terms "amino acid" and "amino acid identity" refers to one of the 20 naturally occurring amino acids or any non-natural analogues that may be in any of the antibodies, variants, or fragments disclosed. Thus "amino acid" as used herein means both naturally occurring and synthetic amino acids. For example, homophenylalanine, citrulline and norleucine are considered amino acids for the purposes of the invention. "Amino acid" also includes amino acid residues such as proline and hydroxyproline. The side chain may be in either the (R) or the (S) configuration. In an aspect, the amino acids are in the D- or L-configuration. If non-naturally occurring side chains are used, non-amino acid substituents may be used, for example to prevent or retard in vivo degradation.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Treatment" and "treating" refer to administration or application of a therapeutic agent (e.g., a Tat 1 analog, peptide or polypeptide described herein) to a subject or performance of a procedure or modality on a subject for the purpose of obtaining a therapeutic benefit of a disease or health-related condition. For example, a treatment may include administration of a pharmaceutically effective amount of a peptide that is capable of activating degradation by the proteasome.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be Alzheimer's disease.

A "variant" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions can be those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH2(CH2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

As used herein, the term "prevent" or "preventing" refers to preventing in whole or in part, or ameliorating or controlling.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The Tat1 analogs and peptide-based compositions described herein can be useful for the treatment of Alzheimer's disease, and the prevention of Alzheimer's disease because they target early processed in Alzheimer's disease development. The compounds disclosed herein can attack the disease by multiple mechanisms and proved to be effective in cell culture and animal models of Alzheimer's disease. Importantly, they reduce the neural cell death and reduce or even reverse the Alzheimer's disease-related cognitive defects in model animals. None of the drugs currently in clinical or preclinical tests utilize the idea of direct activation of the catalytic core proteasome (Cummings J, Lee G, Ritter A, Zhong K. Alzheimer's disease drug development pipeline: 2018. Alzheimer's Dement Transl Res Clin Interv; 2018; 4:195-214). The compounds disclosed herein can be useful for augmentation of Alzheimer's disease as well as other neurodegenerative diseases (e.g., Parkinson's disease).

Disclosed herein are compounds, compositions, peptides and peptidomimetics that activate degradation by the proteasome and protect against Alzheimer's disease progression. Disclosed herein are compounds, compositions, peptides and peptidomimetics that can work as allosteric regulators of the proteasome and are based on a pharmacophore of strongly basic peptide moieties connected by a stable structural turn. Disclosed herein are compounds, compositions, peptides and peptidomimetics that can enhance several-fold the major peptidase activity (chymotrypsin-like; post-hydrophobic cleavages) of the core. This activity is responsible for majority of cleavages in the proteasomal protein substrates. The activation effect is preserved in the 26S assembly, which is the most advanced and most physiologically relevant among the proteasome assemblies sharing the catalytic core. The proteasome activity enhancement is evident not only in vitro but also in heads and brains of drug-treated flies and mice, respectively, with oral (flies, mice) or IP (mice) treatment route. The findings show that the compounds, compositions, peptides and peptidomimetics disclosed herein reduce cell death in a human cell culture model of Alzheimer's disease, reduce cognitive deficits in a fly model of Alzheimer's disease as well as reduce cognitive deficits in a mouse model of Alzheimer's disease Alzheimer's disease. Evidence is provided herein that shows that injection with these are compounds, compositions, peptides and peptidomimetics is capable of penetrating the blood brain barrier in mice and produces protective effects against Alzheimer's disease-like pathology in animals models of the disease. The results also show that the protective effects from these are compounds, compositions, peptides and peptidomimetics stem from enhanced proteasome function and likely employ multiple mutually supportive mechanisms. The results further demonstrate that these are compounds, compositions, peptides and peptidomimetics reduce levels of β-amyloid naturally present in Alzheimer's disease models and also levels of pre-formed introduced β-amyloid and reduce protein levels of BACE1.

Currently there is no effective treatment for Alzheimer's disease which is a mounting and extremely costly public health problem. The compounds, compositions, peptides, peptidomimetics and methods described herein represent the first demonstration that a direct enhancement of proteasome function with designer compounds can protect from Alzheimer's disease pathology and disease progression. An important aspect of the present disclosure is that these are compounds, compositions, peptides and peptidomimetics act through both β-amyloid dependent and independent mechanisms. This is important because most of the failed clinical trials for Alzheimer's disease have been based on technologies which target removal of β-amyloid. Most likely, such intervention comes too late during the irreversible progress of the disease. To the contrary, the compounds, compositions, peptides and peptidomimetics disclosed herein target earlier stages of disease development and thus may prevent neuronal damage. Multiple actions of the compounds, compositions, peptides and peptidomimetics described herein (e.g., activators) augmenting performance of the ubiquitin-proteasome pathway in general and the proteasome in particular: (i) general improvement of protein turnover in aging brain cells; (ii) prevention of formation of polymerization-prone toxic monomers; and (iii) elimination of the toxic monomers before they polymerize and irreversibly harm the cells in brain.

Proteasome is an important protease from the ubiquitin-proteasome pathway responsible for majority of regulated protein turnover in human cells. The giant protease consists of 20S catalytic core that can be decorated with specific protein regulatory modules to form 26S proteasome, distinct forms of "activated" proteasome and a variety of mixed-module assemblies. Small-molecule inhibitors of the catalytic core are established anti-cancer drugs. Small-molecule or peptide-based activators are scarce, with limited reports of in vitro and cell culture tests. The "detergent-activator" often used for in vitro tests with the core proteasome, sodium dodecyl sulfate, is unsuitable as a lead since it damages the enzyme and destroys its ability to interact with regulatory modules.

The compounds, compositions, peptides and peptidomimetics disclosed herein can be referred to as "the Tat compounds", "Tat1 analog" or "Tat1 analogs" and are based on fragments of a viral protein, the HIV-1Tat that binds the 20S core proteasome and competes with the "activator" module. The peptide fragments of the viral protein such as Tat1 and Tat2 are ultimately degraded by the proteasome and thus unsuitable as leads in the unmodified form (Jankowska E, et al. Biopolymers. 2010; 93(5):481-495).

For example, in an aspect, following small-scale SAR studies, a structural beta turn was introduced to the strongly positive Tat1 structure to improve bio-stability and potency toward the core proteasome. The Tic-Oic (TO) provides a synthetic beta turn in Tat-TOD and also in simplified peptidomimetic Tat-3KTO (abbreviated as Tat-KTO) and in Tat-ATO, a negative control devoid of the strong positive charge. A stable beta turn was also introduced to the Tat1 structure by Aib, and a resulting mimetic was a strong activator. The three-turns-like and branching effect in a strong activator Tat Dendrite is achieved with the central benzene.

Tat-TOD and Tat-Den in vitro strongly enhance catalytic performance of the major peptidase (chymotrypsin-like, post-hydrophobic cleavages) of the latent human housekeeping core 20S proteasome at high nanomolar/low micromolar concentrations. The compounds also elevate peptidase activity of the fully assembled human 26S proteasome, an uncommon feature for non-protein regulators. Activation of the 20S core is preserved in the simplified Tat-KTO, however it is low in the ATO derivative, pointing at the significance of both positive charge and a stable structural turn for the biological effect on proteasome. Destabilization of the turn by introducing alanine residues to the Tat1 structure destroyed the activation potency. Introduction of two adjacent turns in the Tat1 structure (Tat1 51/55-TOD) eliminated the activation as well, likely due to a steric hindrance by two rigid turns.

It was tested whether a stable beta turn flanked by short peptide moieties with net positive charge is the proteasome-activating pharmacophore.

Treatment of *Drosophila melanogaster* that model aspects of Alzheimer's disease with either Tat1 8,9TOD or Tat-Dendrite (mixed into food) significantly enhances response to measures of learning, memory and functionality. Improved performance in olfaction aversion training and increased spontaneous activity was observed in elav-GS-Gal4>UAS-APP, UAS-Bace1 flies fed 1 μM Tat-TOD and 1 μM Tat-Den.

Treatment of Tat-TOD significantly enhances cell survival in a cell line that models aspects of Alzheimer's disease. The MC65 cell line overexpresses a C99 fragment of the β-amyloid precursor protein APP under withdrawal of tetracycline, which causes cell death. Treatment with Tat-TOD significantly reduces cell death in this line under conditions of tetracycline withdrawal.

Treatment of Tat-TOD significantly enhances proteasome activity in the central nervous system of mice 24 hours after intraperitoneal injection. Significant increases are seen in a cell line that models aspects of Alzheimer's disease. The MC65 cell line overexpresses a C99 fragment of the β-amyloid precursor protein APP under withdrawal of tetracycline that causes cell death. Treatment 0.04, 0.2 and 1 mg/kg.

Injection of hAPP(J20) mice (which model aspects of Alzheimer's disease pathogenesis) with Tat-TOD significantly reduces protein levels of β-amyloid and protein levels of BACE1 (part of β-amyloid machinery).

Injection of hAPP(J20) mice with Tat-TOD significantly enhances learning and memory based on performance in a novel object recognition.

As described herein, proteasome is an important enzyme of controlled proteolysis responsible for the catabolic arm of proteostasis. The proteasome-dependent functions include among many others, processes important for neuronal functions such as synaptic plasticity, vesicle transport, and synaptic signaling. Ominously, proteasome activity is known to be lowered and followed by deregulation of proteasome-related degradation in brains ravaged by Alzheimer's disease. Consequently, deterioration of the proteasome-related proteostasis would be expected to affect neuronal functions and to drive many of the physiological and symptomatic deficits observed under Alzheimer's disease. Thus, augmentation of the proteasome activity may at least prevent the progression of Alzheimer's disease. To meet the challenge, a set of Tat1 analogs (also herein referred to as proteasome-activating peptidomimetics) based on proteasome-binding and blood-brain-barrier-passing fragments of the viral protein HIV-1 Tat was developed. These compounds enhance the major peptidase activity of the proteasome in vitro by an allosteric mechanism. The activation effect is preserved in cellulo and in vivo. The compounds at low-micromolar concentrations reduce cell death in cell lines that either overexpress APP (amyloid precursor protein) or have been treated with β-amyloid. The peptides and peptidomimetics described herein effectively cross the blood brain barrier in mice and to reduce or even reverse Alzheimer's disease-related deficits in learning and memory in fruit fly and mouse models.

Compositions

Figure 5:
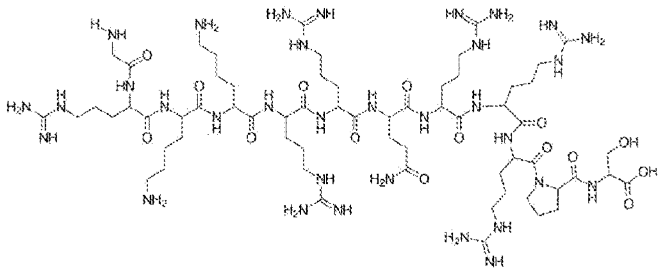
FIG. 5 shows selected derivatives of Tat1 peptide fragment of HIV-1 Tat protein.
Figure 5:
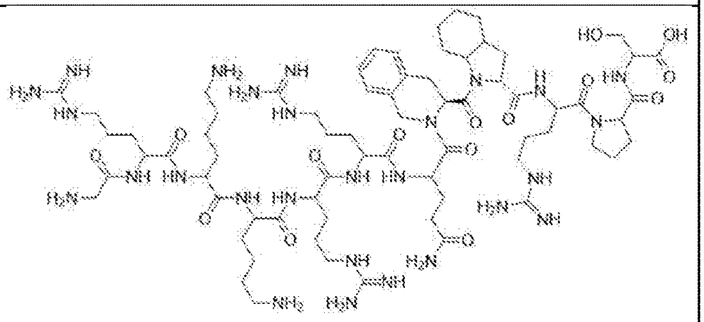
Figure 5:
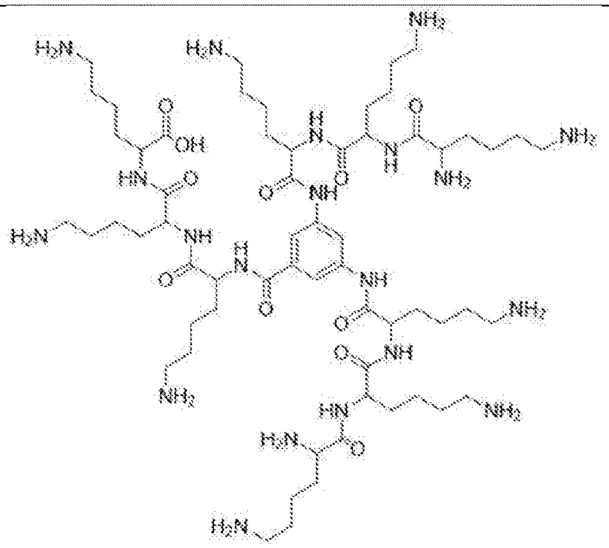
Figure 5:
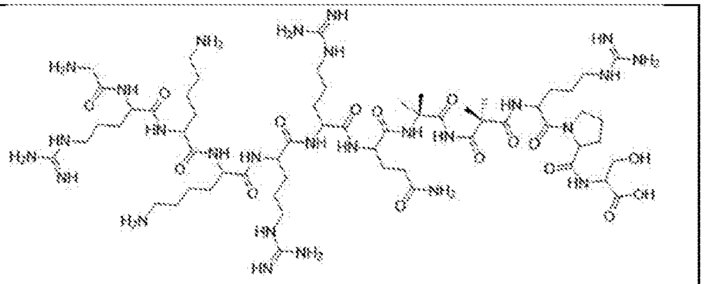
Figure 5:
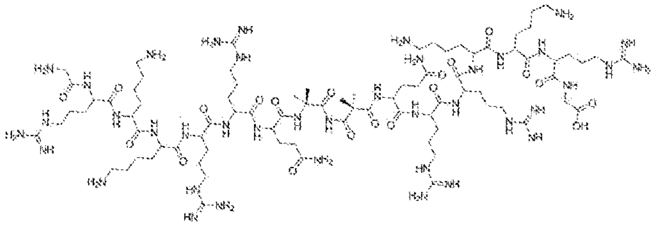

Disclosed herein are Tat1 analogs. For example, Tat1 analogs can be any of SEQ ID NOs: 3-6. In some aspects, the Tat1 analog can be one or more of the sequences or structures shown in FIG. 5. In some aspects, Tat1 (SEQ ID NO: 1) can be modified to prepare a Tat1 analog. Disclosed herein are Tat1 analogs that can have a modification at the 4-5 and/or the 8-9 position of Tat1. In some aspects, the Tat1 analog can comprise a beta-turn conformation at positions 4-5 and/or 8-9 of Tat1. In some aspects, the modification of Tat1 can increase the stabilization of the beta-turn and/or of the Tat1 analog. Also disclosed herein are variants and/or fragments of Tat1 or the Tat1 analogs disclosed herein.

Also disclosed herein are compositions, including pharmaceutical compositions comprising Tat1 analogs, or variants and/or fragments of Tat1 or Tat1 analogs. Disclosed herein are compositions, including pharmaceutical compositions, comprising a Tat1 analog, or variants and/or fragments of Tat1 or Tat1 analogs capable of activating 20S and/or 26S proteasome activity. Also, disclosed herein are compositions, including pharmaceutical compositions, comprising a Tat1 analog, or variants and/or fragments of Tat1 or Tat1 analogs, capable of ameliorating one or more symptoms of Alzheimer's disease in a subject. Further disclosed herein are compositions, including pharmaceutical compositions, comprising a Tat1 analog, or variants and/or fragments of Tat1 or Tat1 analogs capable of increasing turnover of amyloid precursor protein or β-secretase enzyme BACE1.

Disclosed herein are compositions comprising any of the peptides disclosed herein, including but not limited to Tat1 analogs. In some aspects the peptide can comprise the amino acid sequence GRKKRRQ-AibG-RPS (SEQ ID NO: 4), or a fragment or variant thereof; GRKKRRQ-AibG-QRRKKRG (SEQ ID NO: 5), or a fragment or variant thereof; or the amino acid sequence (Tat1-Dendrite) SEQ ID NO: 6, or a fragment or variant thereof.

Disclosed herein are compositions comprising peptides that comprise the amino acid sequence of SEQ ID NO: 3: GRKKRRQ-TOD-RPS; SEQ ID NO: 4: GRKKRRQ-AIBG-RPS; SEQ ID NO: 5: GRKKRRQ-AibG-QRRKKRG; or SEQ ID NO: 6: Tat1-Dendrite.

In some aspects, the peptides comprise the amino acid sequence GRKKRRQ-TOD-RPS (SEQ ID NO: 3). In some aspects, the peptides comprise the amino acid sequence GRKKRRQ-AIBG-RPS (SEQ ID NO: 4). In some aspects, the peptides comprise the amino acid sequence GRKKRRQ-AibG-QRRKKRG (SEQ ID NO: 5). In some aspects, the peptides comprise the amino acid sequence (Tat1-Dendrite) (SEQ ID NO: 6).

In some aspects, the peptides described herein can have at least 80% sequence identity to any of SEQ ID NOs: 1, and 3-6. In some aspects, the peptides described herein can have at least 85% sequence identity, at least 90% sequence identify, at least 95% sequence identity, or at least 98% sequence identity to any of SEQ ID NOs: 3-6.

In some aspects, any of the compositions described herein can further comprise a pharmaceutically acceptable carrier. In some aspects, any of the compositions described herein can be formulated for intravenous, subcutaneous or intranasal administration.

Disclosed herein are peptides that comprise variants of GRKKRRQRRRPS (SEQ ID NO: 1). In some aspects, the variants can comprise a sequence having at least 20%, 30%, 40%, 50%, 60%, 70%, 80%, 90%, 95%, 98%, 99% identity to SEQ ID NO: 1. In some aspects, the variants retain at least 50%, 75%, 80%, 85%, 90%, 95% or 99% of the biological activity of the reference protein described herein.

Disclosed herein are peptides that comprise variants of GRKKRRQ-TOD-RPS (SEQ ID NO: 3), GRKKRRQ-AIBG-RPS (SEQ ID NO: 4), GRKKRRQ-AibG-QRRKKRG (SEQ ID NO: 5), or SEQ ID NO: 6 (Tat1-dendrite). In some aspects, the variants can comprise a sequence having at least 20%, 30%, 40%, 50%, 60%, 70%, 80%, 90%, 95%, 98%, 99% identity to SEQ ID NO: 1, SEQ ID NO: 3, SEQ ID NO: 4, SEQ ID NO: 5, or SEQ ID NO: 6. In some aspects, the variants retain at least 50%, 75%, 80%, 85%, 90%, 95% or 99% of the biological activity of the reference protein described herein.

As used herein, the term "peptide" refers to a linear molecule formed by binding amino acid residues to each other via peptide bonds. As used herein, the term "polypeptide" refers to a polymer of (the same or different) amino acids bound to each other via peptide bonds.

In some aspects, the peptide or polypeptide can be of any length so long as the peptides described herein can activate 20S and/or 26S proteasome activity.

In some aspects, the peptides described herein can further comprise 1, 2, 2, 4, 5, 10, 15, 20, 25, 30, 35, 40, 45, 50 amino acid residues at the N-terminal end of the disclosed peptides. In some aspects, the peptides described herein can further comprise 1, 2, 2, 4, 5, 10, 15, 20, 25, 30, 35, 40, 45, 50 amino acid residues at the C-terminal end of the disclosed peptides disclosed herein. For example, disclosed herein a Ta1 analogs that comprise SEQ ID NO: 3, SEQ ID NO: 4, SEQ ID NO: 5, or SEQ ID NO: 6 and further comprise 1, 2, 2, 4, 5, 10, 15, 20, 25, 30, 35, 40, 45, 50 amino acid residues at the N-terminal or C-terminal end of the Tat1 analog. In some aspects, the amino acid residues that can be present at either the N-terminal end or the C-terminal end of any of the peptides disclosed herein can be unimportant for activating 20S and/or 26S proteasome activity. In some aspects, the amino acid residues added to the N-terminal end or the C-terminal end of the peptides disclosed herein may prevent ubiquitination, improve stability, help maintain the three dimensional structure of the peptide (e.g., Tat1 analog), or a combination thereof.

In some aspects, the peptides disclosed herein can further comprise one or more amino acid residues that comprise a modified side chain. In some aspects, one or more amino acids of any of the peptides disclosed here can have a modified side chain. Examples of side chain modifications include but are not limited to modifications of amino acid groups, such as reductive alkylation; amidination with methylacetimidate; acylation with acetic anhydride; carbamolyation of amino groups with cynate; trinitrobenzylation of amino acid with 2,4,6-trinitrobenzene sulfonic acid (TNBS); alkylation of amino groups with succinic anhydride; and pyridoxylation with pridoxal-5-phosphate followed by reduction with $NaBH_4$.

In some aspects, a guanidine group of an arginine residue may be modified by the formation of a heterocyclic condensate using a reagent, such as 2,3-butanedione, phenylglyoxal, and glyoxal. In some aspects, the carboxyl group may be modified by carbodiimide activation via O-acylisourea formation, followed by subsequent derivatization, for example, to a corresponding amide.

In some aspects, a sulfhydryl group may be modified by methods, such as carboxymethylation with iodoacetic acid or iodoacetamide; performic acid oxidation with cysteic acid; formation of mixed disulfides by other thiol compounds; a reaction by maleimide, maleic anhydride, or other substituted maleimide; formation of mercury derivatives using 4-chloromercuribenzoate, 4-chloromercuriphenylsulfonic acid, phenylmercury chloride, 2-chloromercuri-4-nitrophenol, and other mercurial agents; and carbamolyation with cyanate at alkaline pH. In addition, the sulfhydryl group of cysteine may be substituted with a selenium equivalent, whereby a diselenium bond may be formed instead of at least one disulfide bonding site in the peptide.

In some aspects, the tryptophan residue may be modified by, for example, oxidation with N-bromosuccinimide or alkylation of the indole ring by 2-hydroxy-5-nitrobenzyl bromide or sulfonyl halide. Meanwhile, the tyrosine residue may be modified by nitration using tetranitromethane to form a 3-nitrotyrosine derivative.

In some aspects, the modification of the imidazole ring of a histidine residue may be accomplished by alkylation with an iodoacetic acid derivative or N-carbethoxylation with diethylpyrocarbonate.

In some aspects, the proline residue may be modified by, for example, hydroxylation at the 4-position.

In some aspects, the peptides described herein can be further modified to improve stability. In some aspects, any of the amino acid residues of the peptides described herein can be modified to improve stability. In some aspects, peptide can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the peptide described herein.

As used herein, the term "peptide" can also be used to include functional equivalents of the peptides described herein (e.g., functional equivalents of the Tat1 analogs disclosed herein). As used herein, the term "functional equivalents" can refer to amino acid sequence variants having an amino acid substitution, addition, or deletion in some of the amino acid sequence of the peptide or polypeptide while simultaneously having similar or improved biological activity, compared with the peptide as described herein. In some aspects, the amino acid substitution can be a conservative substitution. Examples of the naturally occurring amino acid conservative substitution include, for example, aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met). In some aspects, the amino acid deletion can be located in a region that is not directly involved in the activity of the peptide and polypeptide disclosed herein.

In some aspects, the amino acid sequence of the peptides described herein can include a peptide sequence that has substantial identity to any of sequence of the peptides disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the peptides described herein can include a peptide sequence that has some degree of identity or homology to any of sequences of the peptides disclosed herein. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The peptides described herein can have at least or about 25%, 50%, 65%, 75%, 80%, 85%, 90%, 95%, 96%, 97%, 98%, or 99% identity or homology to the peptide or polypeptide, wherein the peptide is one or more of SEQ ID NOs: 1, 3-6.

Disclosed herein are compounds having a structure represented by a formula (Tat1 8,9 TOD; SEQ ID NO: 3):

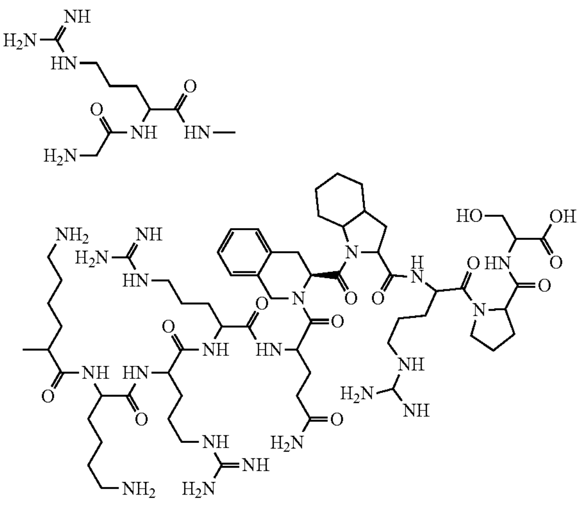

or a pharmaceutically acceptable salt thereof.

Disclosed herein are compounds having a structure represented by a formula (Tat1 8,9 Aib; SEQ ID NO: 4):

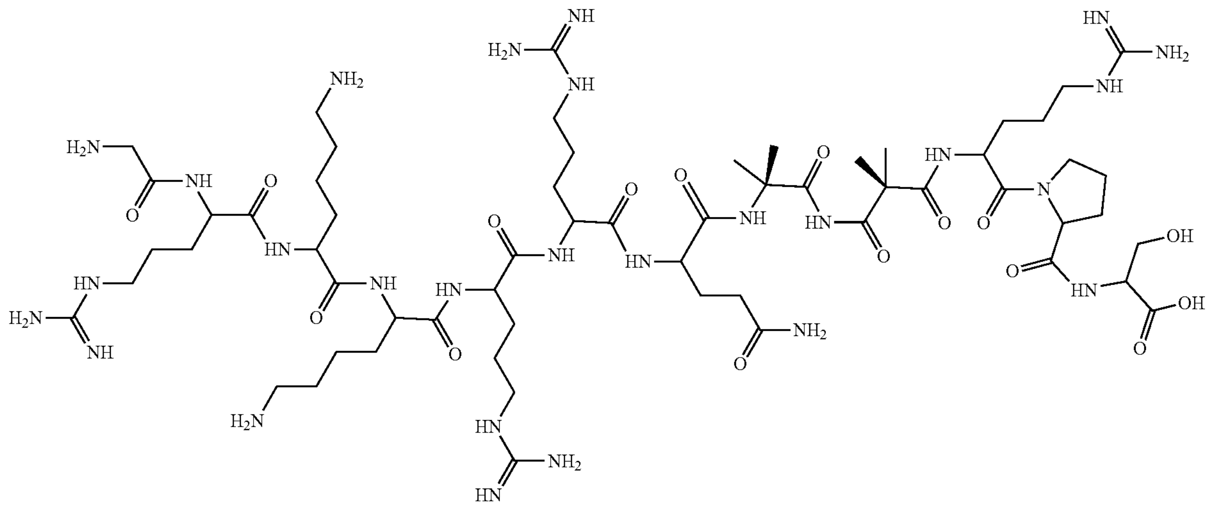

or a pharmaceutically acceptable salt thereof.

Disclosed herein are compounds having a structure represented by a formula (Tat1-Dendrite; SEQ ID NO: 6):

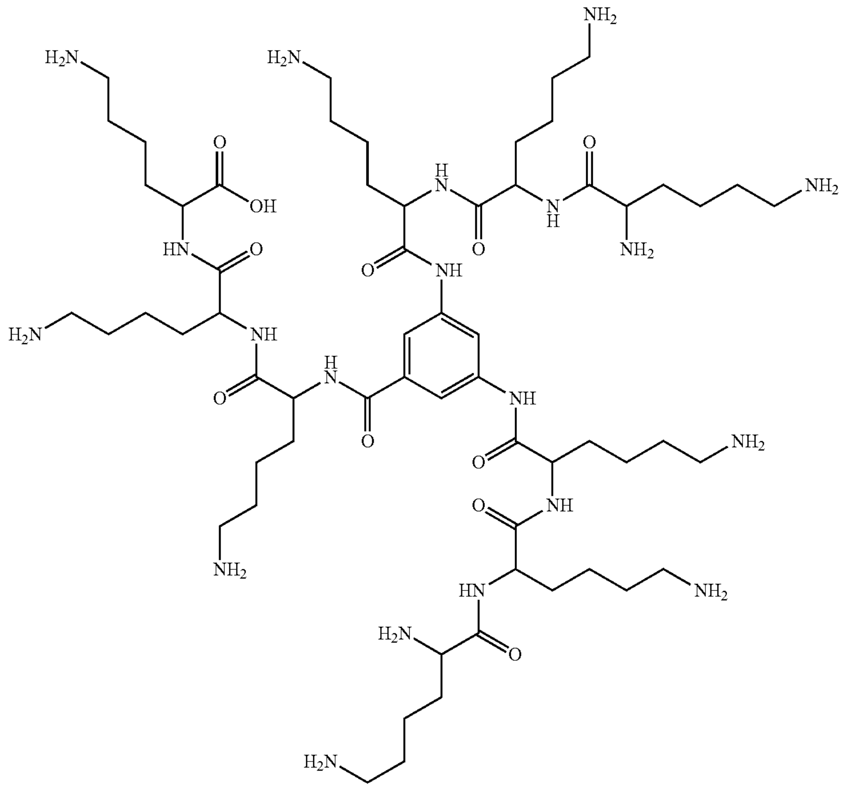 [SMILES: NCCCCC(N)C(=O)NC(CCCCN)C(=O)NC(CCCCN)C(=O)Nc1cc(NC(=O)C(CCCCN)NC(=O)C(CCCCN)NC(=O)C(N)CCCCN)cc(C(=O)NC(CCCCN)C(=O)NC(CCCCN)C(=O)NC(CCCCN)C(=O)O)c1]

or a pharmaceutically acceptable salt thereof.

Disclosed herein are compounds having a structure represented by a formula (Tat5 8,9 Aib; SEQ ID NO: 5):

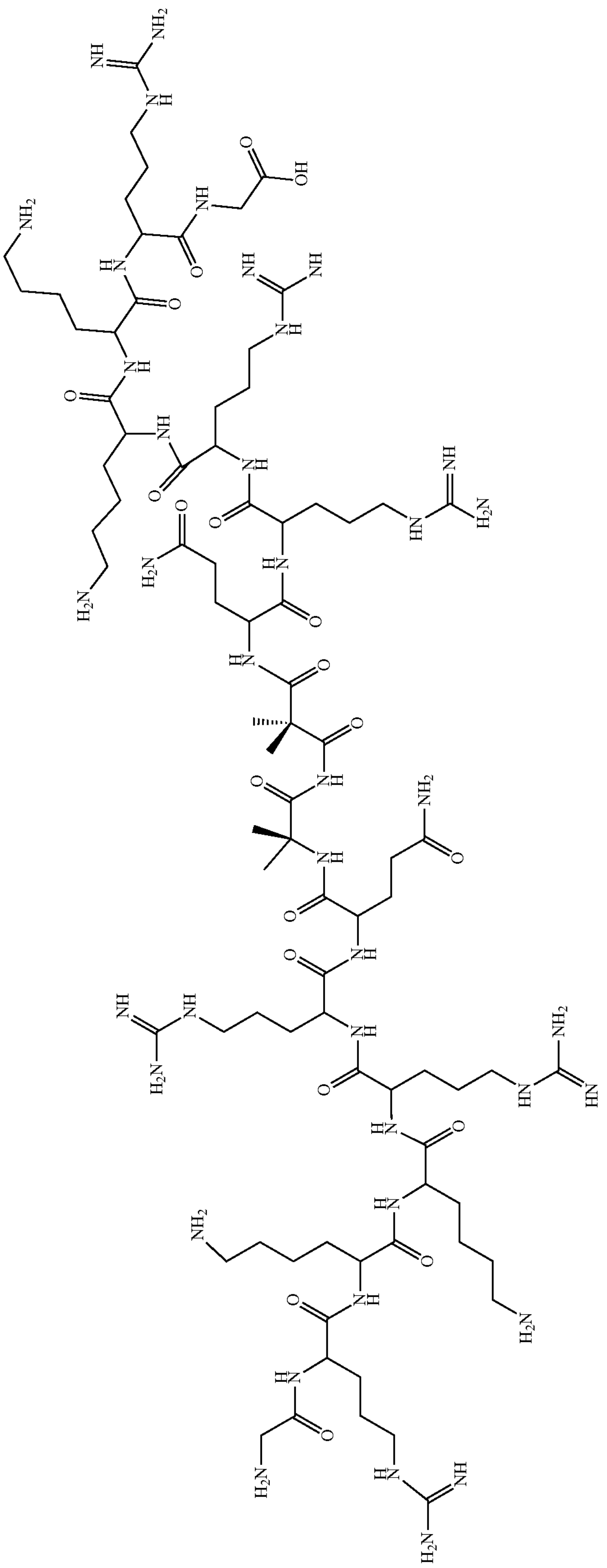

or a pharmaceutically acceptable salt thereof.

As used herein, the term "stability" refers to storage stability (e.g., room-temperature stability) as well as in vivo stability. The foregoing protective group can protect the peptides described herein from the attack of protein cleavage enzymes in vivo.

Pharmaceutical Compositions

As disclosed herein, are pharmaceutical compositions, comprising the peptides and/or Tat1 analogs described herein. Also disclosed herein, are pharmaceutical compositions, comprising the peptides and/or Tat1 analogs described herein and a pharmaceutical acceptable carrier. Further disclosed herein are pharmaceutical compositions for increasing turnover of amyloid precursor protein or β-secretase enzyme BACE1; activating 20S or 26S proteosome activity; ameliorating one or more symptoms of Alzheimer's disease; or increasing 20S or 26S proteasome activity in a subject. In some aspects, the pharmaceutical compositions can comprise: a) a therapeutically effective amount of the peptides and/or Tat1 analogs described herein; and b) a pharmaceutically acceptable carrier.

The pharmaceutical compositions described above can be formulated to include a therapeutically effective amount of a peptides and/or Tat1 analogs disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to Alzheimer's disease.

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with Alzheimer's disease in an amount sufficient to at least partially improve a sign or symptom or to inhibit the progression of (and preferably arrest) the symptoms of the condition, its complications, and consequences (e.g., developing Alzheimer's disease). An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of Alzheimer's disease or a symptom of Alzheimer's disease is ameliorated. One or more of the symptoms can be less severe. Recovery can be accelerated in an individual who has been treated.

In some aspects, the pharmaceutical composition can be formulated for intravenous administration. In some aspects, the pharmaceutical composition can be formulated for subcutaneous, intranasal, oropharyngeal or oral administration. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the peptides disclosed herein. Thus, compositions can be prepared for parenteral administration that include the peptides dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein are methods of increasing 20S or 26S proteasome activity in a subject. In some aspects, the methods can comprise administering to the subject with a disease a therapeutically effective amount of a composition of any of the peptides or compounds or pharmaceutical compositions disclosed herein. In some aspects, the compositions can further comprise a pharmaceutically acceptable carrier. In some aspects, the 20S or the 26S proteasome activity can be increased. In some aspects, the chymotrypsin-like activity of latent human 20S proteasome can be activated. In some aspects, the chymotrypsin-like activity of latent human 26S proteasome can be activated. In some aspects, the composition increases degradation of Aβ machinery/substrate. In some aspects, the disease can be Alzheimer's disease or a cancer. In some aspects, the cancer can be a blood cancer.

Disclosed herein are methods treating a disease. In some aspects, the treating of the disease requires proteasome activation. In some aspects, the methods can comprise administering to a subject with the disease a therapeutically effective amount of a composition of any of the peptides or compounds or pharmaceutical compositions disclosed herein. In some aspects, the compositions can further comprise a pharmaceutically acceptable carrier. In some aspects, the 20S or the 26S proteasome activity can be increased. In some aspects, the chymotrypsin-like activity of latent human 20S proteasome can be activated. In some aspects, the chymotrypsin-like activity of latent human 26S proteasome can be activated. In some aspects, the composition increases degradation of Aβ machinery/substrate. In some aspects, the disease can be Alzheimer's disease or a cancer. In some aspects, the cancer can be a blood cancer.

Disclosed herein are methods of increasing turnover of amyloid precursor protein or β-secretase enzyme BACE1. In some aspects, the methods can comprise administering to a subject a therapeutically effective amount of a composition of any of the peptides or compounds or pharmaceutical compositions disclosed herein. In some aspects, the compositions can further comprise a pharmaceutically acceptable carrier.

Disclosed herein are methods of increasing survival of neuroblasts. In some aspects, the methods can comprise administering to a subject a therapeutically effective amount of a composition of any of the peptides or compounds or pharmaceutical compositions disclosed herein. In some aspects, the compositions can further comprise a pharmaceutically acceptable carrier.

Disclosed herein are methods of reducing amyloid precursor protein levels. In some aspects, the methods can comprise administering to a subject a therapeutically effective amount of a composition of any of the peptides or compounds or pharmaceutical compositions disclosed herein. In some aspects, the compositions can further comprise a pharmaceutically acceptable carrier.

Disclosed herein are methods of improving cognitive function in a subject. In some aspects, the methods can comprise administering to the subject a therapeutically effective amount of a composition of any of the peptides or compounds or pharmaceutical compositions disclosed herein. In some aspects, the compositions can further comprise a pharmaceutically acceptable carrier.

Disclosed herein are methods of activating 20S or 26S proteosome activity. In some aspects, the methods can comprise administering to a subject a therapeutically effective amount of a composition of any of the peptides or compounds or pharmaceutical compositions disclosed herein. In some aspects, the compositions can further comprise a pharmaceutically acceptable carrier. In some aspects, the 20S or the 26S proteasome activity can be increased. In some aspects, the chymotrypsin-like activity of latent human 20S proteasome can be activated. In some aspects, the chymotrypsin-like activity of latent human 26S proteasome can be activated. In some aspects, the composition increases degradation of Aβ machinery/substrate.

Disclosed herein are methods of ameliorating one or more symptoms of Alzheimer's disease. In some aspects, the methods can comprise administering to a subject a therapeutically effective amount of a composition of any of the peptides or compounds or pharmaceutical compositions disclosed herein. In some aspects, the compositions can further comprise a pharmaceutically acceptable carrier. In some aspects, the 20S or the 26S proteasome activity can be increased. In some aspects, the chymotrypsin-like activity of latent human 20S proteasome can be activated. In some aspects, the chymotrypsin-like activity of latent human 26S proteasome can be activated. In some aspects, the composition increases degradation of Aβ machinery/substrate.

In some aspects, the methods can comprise administering a composition that can be formulated for intravenous, subcutaneous, intranasal, or oral administration.

In some aspects, the subject can be identified as being in need of treatment before the administration step. In some aspects, the subject can have Alzheimer's disease. In some aspects, the subject can have a cancer. In some aspects, the cancer can be a blood cancer.

Amounts effective for this use can depend on the severity of the condition, disease or disease or the severity of the risk of the condition, disease or disorder, and the weight and general state and health of the subject, but generally range from about 0.05 μg to about 1000 μg (e.g., 0.5-100 μg) of an equivalent amount of the peptide per dose per subject. Suitable regimes for initial administration and booster administrations are typified by an initial administration followed by repeated doses at one or more hourly, daily, weekly, or monthly intervals by a subsequent administration. For example, a subject can receive peptides in the range of about 0.05 to 1,000 μg equivalent dose per dose one or more times per week (e.g., 2, 3, 4, 5, 6, or 7 or more times per week). For example, a subject can receive 0.1 to 2,500 μg (e.g., 2,000, 1,500, 1,000, 500, 100, 10, 1, 0.5, or 0.1 μg) dose per week. A subject can also receive peptides in the range of 0.1 to 3,000 μg per dose once every two or three weeks. A subject can also receive 2 mg/kg every week (with the weight calculated based on the weight of the peptide.

The total effective amount of the peptides disclosed herein in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the peptides present within the compositions described herein and used in the methods as disclosed herein applied to mammals (e.g., humans) can be determined by one of ordinary skill in the art with consideration of individual differences in age, weight, and other general conditions (as mentioned above).

Kits

The kits can comprise one or more of the peptides or pharmaceutical compositions disclosed herein. The peptides or compositions described herein can be packaged in a suitable container labeled, for example, for use to treat Alzheimer's disease or a cancer. Accordingly, packaged products (e.g., sterile containers containing the composition described herein and packaged for storage, shipment, or sale at concentrated or ready-to-use concentrations) and kits, including at least one or more of the peptides as described herein and instructions for use, are also within the scope of the disclosure. A product can include a container (e.g., a vial, jar, bottle, bag, or the like) containing the peptides or compositions described herein. In addition, the kits further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The peptides or compositions can be ready for administration (e.g., present in dose-appropriate units), and may include a pharmaceutically acceptable adjuvant, carrier or other diluent. Alternatively, the compounds can be provided in a concentrated form with a diluent and instructions for dilution.

EXAMPLES

Example 1

Genetic and Pharmacologic Proteasome Augmentation Ameliorates Alzheimer's Disease-like Symptom and Pathology Progression Through Increased Turnover of Amyloid Precursor Protein Abstract. The proteasome has roles in neuronal proteostasis, including removal of misfolded or oxidized proteins, presynaptic protein turnover, as well as synaptic efficacy and plasticity. Proteasome dysfunction is a feature of Alzheimer's disease (Almeida, C. G., et al. *The Journal of neuroscience: the official journal of the Society for Neuroscience* 26, 4277-4288, doi:10.1523/ JNEUROSCI.5078-05.2006 (2006); Shringarpure, R., et al. *Cell Mol Life Sci* 57, 1802-1809 (2000); and Rosen, K. M. et al. *Journal of neuroscience research* 88, 167-178, doi:10.1002/ jnr.22178 (2010)). Artificially impairing proteasome can mimic many neurodegeneration-like phenotypes (Bedford, L. et al. *J Neurosci* 28, 8189-8198, doi:10.1523/ JNEUROSCI.2218-08.2008 (2008); and Romero-Granados, R., et al. *PLoS One* 6, e28927, doi:10.1371/ journal.pone.0028927 (2011)). The results disclosed herein show that manipulation of proteasome activity can influence the rate of Alzheimer's disease-like progression. The results also show that augmentation of proteasome function in flies and cell cultures delays Alzheimer's disease-like mortality, cell death and cognitive deficits. Described herein is a transgenic mouse with neuronal-specific proteasome overexpression. When crossed with a mouse model of Alzheimer's disease, reduced mortality and diminished Alzheimer's disease-like cognitive deficits result. To establish translational relevance, a set of proteasome activating peptide mimetics based on modification of the HIV protein TAT1 were developed. These agonists enhance 20S as well as 26S proteasome activity and stably penetrate the blood-brain-barrier. The results also show that treatment with these agonists protect against Alzheimer's disease-like cell death in a cell culture model of Alzheimer's disease and cognitive decline as well as mortality in fly, and mouse models of Alzheimer's disease. The protective effects observed from proteasome overexpression in the models described herein appear at least in part driven by increased turnover of the amyloid precursor protein (APP) or β-secretase enzyme BACE1 by the proteasome. The results disclosed herein demonstrate that proteasome plays an important role in Alzheimer's disease-like pathogenesis in diverse models of the disease, and thus that it may represent a new therapeutic target for Alzheimer's disease.

Alzheimer's disease affects millions world-wide, producing cognitive deficits and increased mortality. Brain tissue from patients with Alzheimer's disease have reduced proteasome function (Keller, J. N., et al. *J Neurochem* 75, 436-439, doi:10.1046/ j.1471-4159.2000.0750436. x (2000); and Keck, S., et al. *J Neurochem* 85, 115-122, doi:10.1046/ j.1471-4159.2003.01642. x (2003)). Proteasome represents the major, multifunctional and multi-subunit protease of the ubiquitin-proteasome-pathway (Keller, J. N., et al. *J Neurochem* 75, 436-439, doi:10.1046/ j.1471-4159.2000.0750436. x (2000)). Proteasome impairment in Alzheimer's disease represents a robust feature of the disease occurring in mouse, cell culture and *Drosophila* models of Alzheimer's disease (FIG. 1A). This is driven by direct inhibition of the enzymatic activity of the proteasome complex by intracellular Aβ (Almeida, C. G., et al. *The Journal of neuroscience: the official journal of the Society for Neuroscience* 26, 4277-4288, doi:10.1523/ JNEUROSCI.5078-05.2006 (2006); and Shringarpure, R., et al. *Cell Mol Life Sci* 57, 1802-1809 (2000)). Many pathological aspects of Alzheimer's disease are thought to stem from accumulation of intracellular Aβ (LaFerla, F. M., et al. *Nat Rev Neurosci* 8, 499-509, doi:10.1038/ nrn2168 (2007)), either internalized by membrane trafficking (Bahr, B. A. et al. *J Comp Neurol* 397, 139-147 (1998)) or generated from APP present on the Golgi and other intracellular membranes (Greenfield, J. P. et al. *Proc Natl Acad Sci USA* 96, 742-747 (1999)). The proteasome has roles in presynaptic protein turnover, synaptic efficacy and plasticity, along with many other functions impaired in Alzheimer's disease (Upadhya, S. C. & Hegde, A. N. *BMC biochemistry* 8 Suppl 1, S12, doi:10.1186/1471-2091-8-S1-S12 (2007)). Thus, toxicity of internal/internalized Aβ may come, in part, from its ability to impair proteasome function. In support of this, mice with inhibited neuronal proteasome function show neurodegeneration and formation of Lewy-like bodies (Bedford, L. et al. *J Neurosci* 28, 8189-8198, doi:10.1523/ JNEUROSCI.2218-08.2008 (2008)), furthermore injection with a proteasome inhibitor causes neurodegeneration and cognitive deficits (Romero-Granados, R., et al. *PLoS One* 6, e28927, doi: 10.1371/ journal.pone.0028927 (2011)).

Figure 1B:
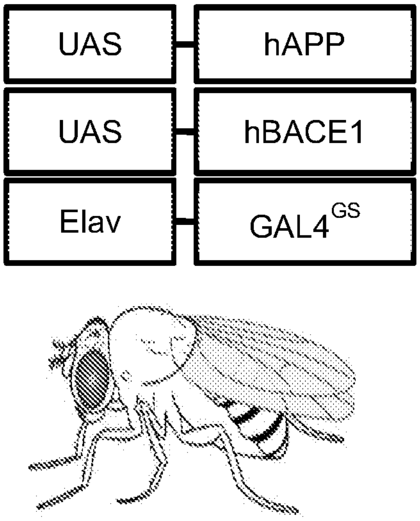
Figure 1C:
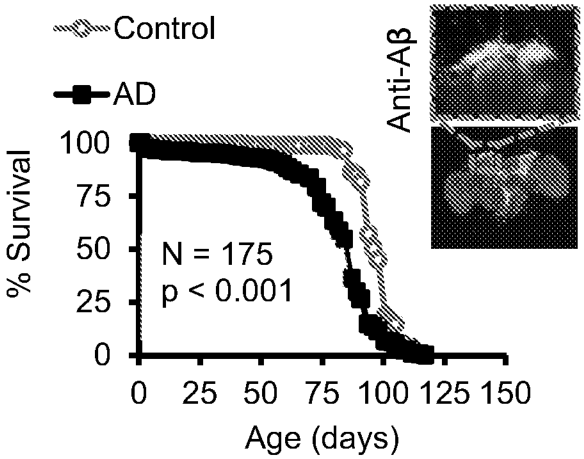
Figure 1D:
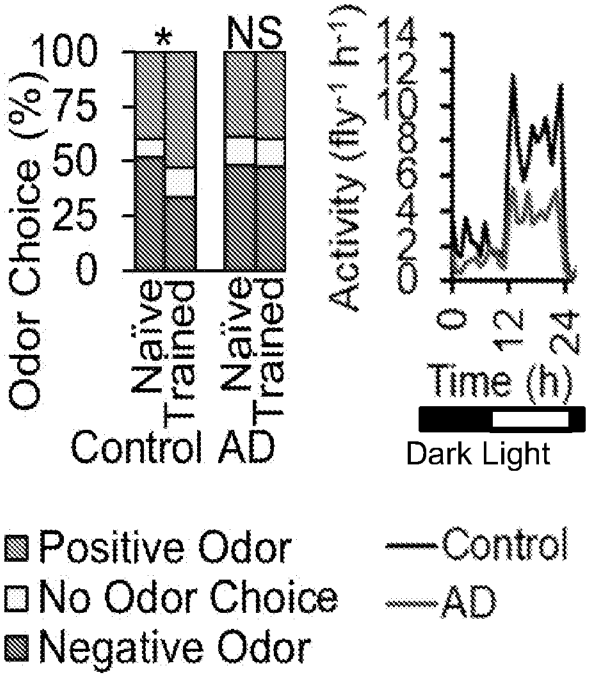

Alzheimer's disease was initially modelled through overexpression of wild-type human APP and BACE1, with expression limited to post-adulthood to avoid developmental artifacts (FIG. 1B). This model displayed shortened lifespan (FIG. 1C) Aβ accumulation in the mushroom body (learning and memory center (Gronenberg, W. & Lopez-Riquelme, G. O. *Acta Biol Hung* 55, 31-37, doi:10.1556/ ABiol.55.2004.1-4.5 (2004))) (FIG. 1C inset), cognitive deficits (olfaction aversion training) and spontaneous activity deficits (FIG. 1D).

Proteasome function was enhanced through overexpression of Prosβ5 (major, chymotrypsin-like peptidase in proteasome core (Heinemeyer, W., et al. *J Biol Chem* 272, 25200-25209, doi:10.1074/ jbc.272.40.25200 (1997))). Proteasome assembly can be driven via an autoregulatory process where overexpression of Prosβ5 increases whole proteasome assembly and expression of other proteasome subunits in cell culture (Chondrogianni, N. et al. *J Biol Chem* 280, 11840-11850, doi:10.1074/ jbc.M413007200 (2005)), *C. elegans* (Chondrogianni, N., et al. *Faseb J* 29, 611-622, doi:10.1096/ fj.14-252189 (2015)) and *Drosophila* (Munkacsy, E. et al. *Aging Cell, e*13005, doi:10.1111/ acel.13005 (2019); and Nguyen, N. N. et al. *Sci Rep* 9, 3170, doi:10.1038/ s41598-019-39508-4 (2019)).

Figure 1E:
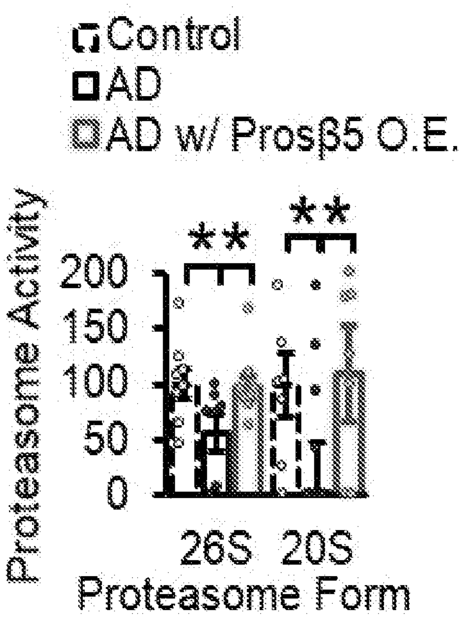
Figure 1F:
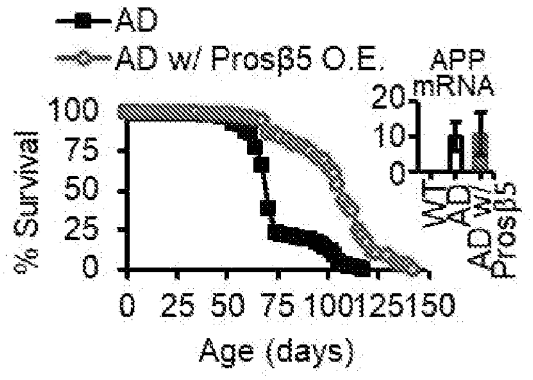
Figure 1G:
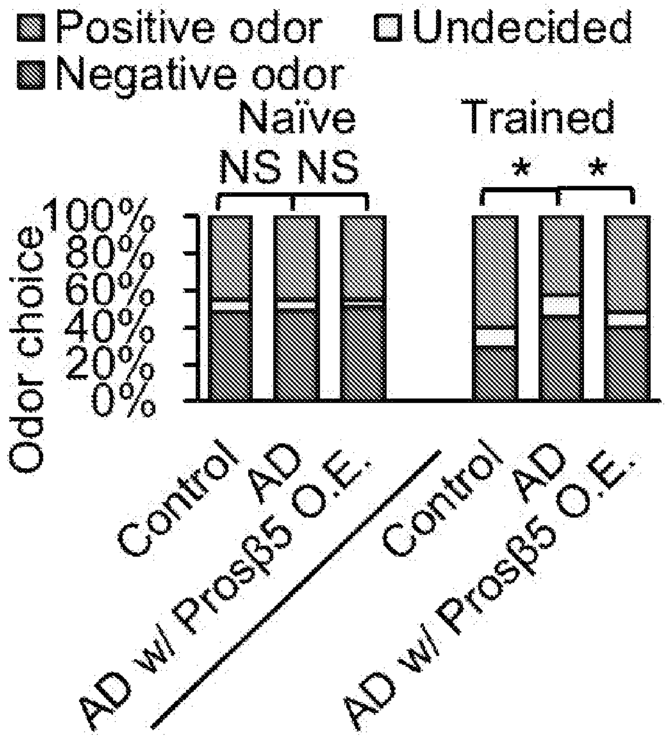
Figure 1H:
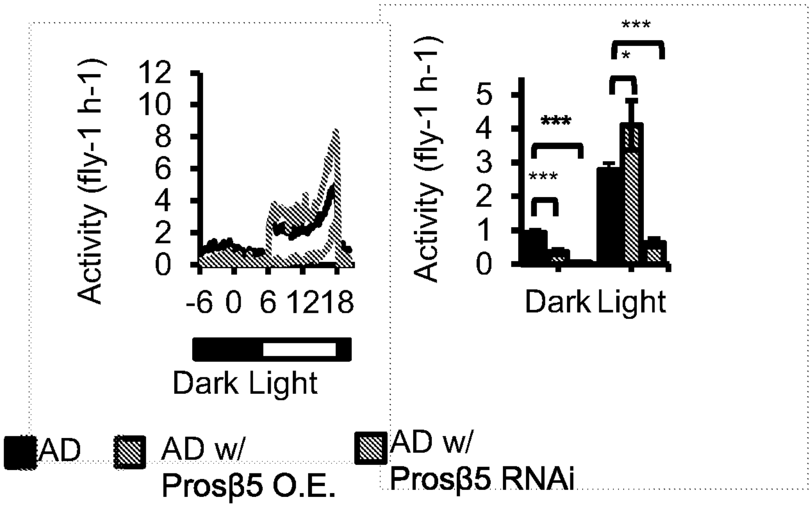

Prosβ5 overexpression prevents Alzheimer's disease-like proteasome activity deficits (FIG. 1E). This abrogates Alzheimer's disease-like mortality (FIG. 1F). Prosβ5-transgene overexpression does not alter mRNA levels of APP thus this does not represent an artifact from GAL4 competition (FIG. 1F inset). Furthermore enhancing proteasome function prevents Alzheimer's disease-like deficits in associative learning and memory (olfaction aversion training). Flies are exposed to two neutral odors (3-octanol & 4-methylcyclohexanol) and trained to associate one with a negative sensation (mild electric shock). Odor choice is then evaluated by T-maze (Malik, B. R. & Hodge, J. J. *J Vis Exp, e*50107, doi:10.3791/50107 (2014)). Control flies showed a significant increase in avoidance of the 'negative' odor after training. While Alzheimer's disease flies showed no improvement. However, when ProsB5 was overexpressed in the Alzheimer's disease background, a restoration of post-training improvement was observed (FIG. 1G), demonstrating a retention of associative learning/memory. In addition, enhancing proteasome function reduced Alzheimer's disease-like deficits in spontaneous activity and circadian rhythmicity (FIG. 1H). This data shows that proteasome overexpression can reduce Alzheimer's disease-like deficits in a fly model of the disease.

Figure 2A:
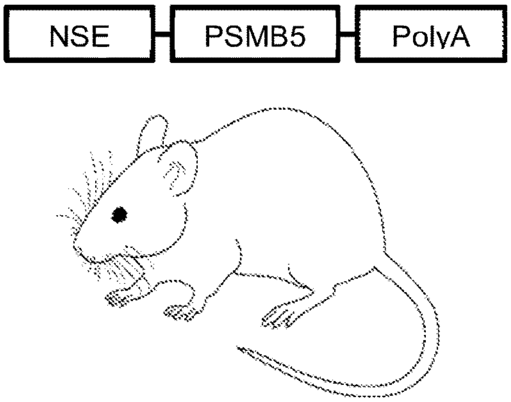
Figure 2B:
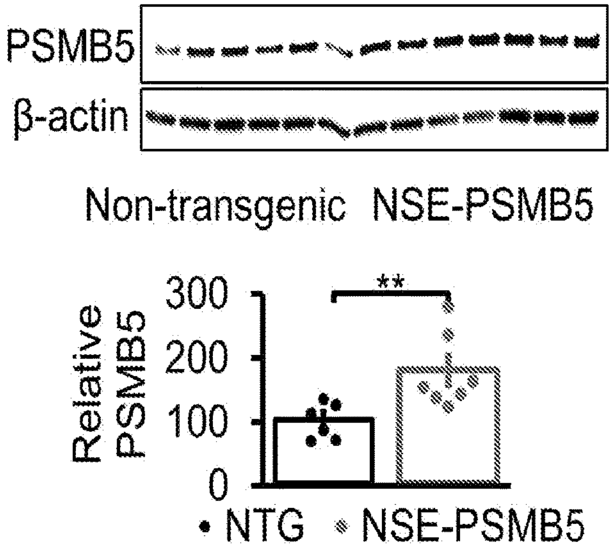
Figure 2C:
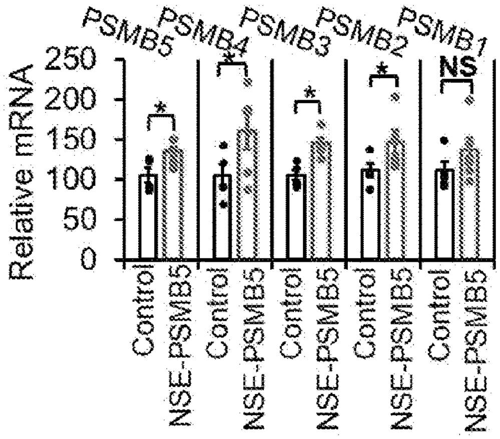
Figure 2D:
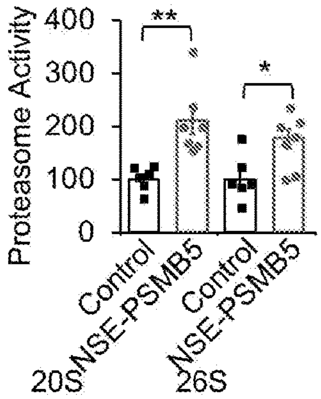
Figure 2E:
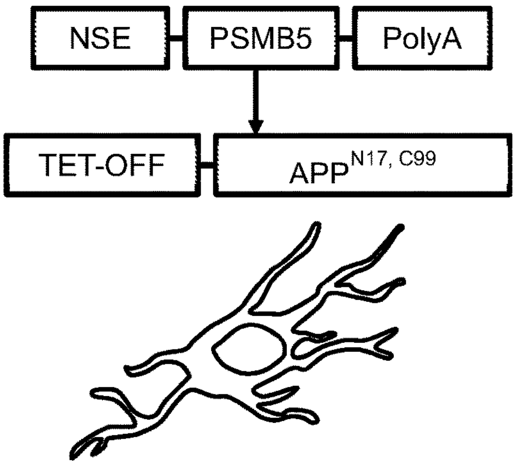
Figure 2F:
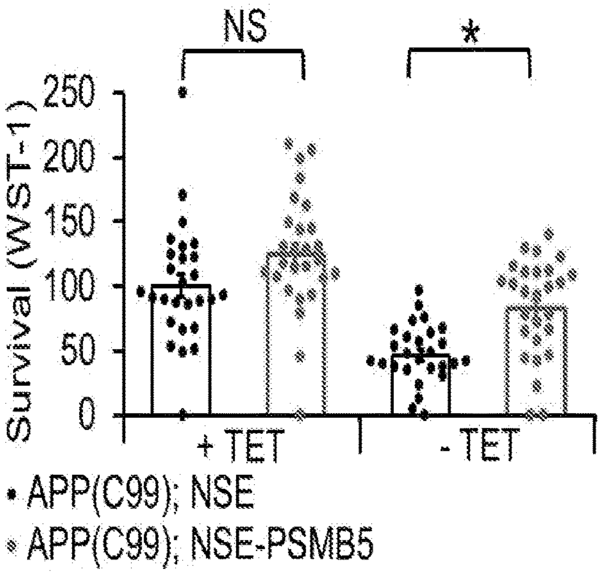
Figure 2K:
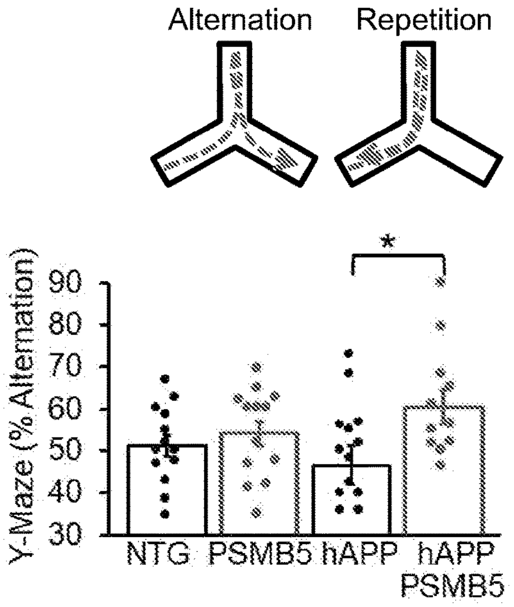

To investigate the translational potential, a transgenic mouse containing an additional copy of mouse PSMB5 (Prosβ5 orthologue) fused to the Neuron Specific Enolase promoter (Mi, J. et al. *PLoS One* 8, e83609, doi:10.1371/journal.pone.0083609 (2013)) (NSE-PSMB5) (FIG. 2A) was generated. The mice appear physiologically normal and display no recorded physiological deficits. Brains taken at 3-months show a modest increase in PSMB5 protein levels (FIG. 2B), elevated expression of multiple proteasome subunits (FIG. 2C), consistent with findings from other model systems (Chondrogianni, N. et al. *J Biol Chem* 280, 11840-11850, doi:10.1074/ jbc.M413007200 (2005); Chondrogianni, N., et al. *Faseb J*29, 611-622, doi:10.1096/ fj.14-252189 (2015); Munkacsy, E. et al. *Aging Cell, e*13005, doi:10.1111/ acel.13005 (2019); and Nguyen, N. N. et al. *Sci Rep* 9, 3170, doi:10.1038/ s41598-019-39508-4 (2019)), along with increased proteasome activity (FIG. 2D). To test Alzheimer's disease-protective capacity, this construct was transfected into MC65 cells (TET-OFF $APP^{\Delta N17-C99}$ overexpression cell-line (Sopher, B. L., et al. *Mol Chem Neuropathol* 29, 153-168 (1996)). This significantly reduced APP-overexpression-induced cell death showing a protective effect against Alzheimer's disease-like toxicity (FIG. 2E-F)

Figure 2L:
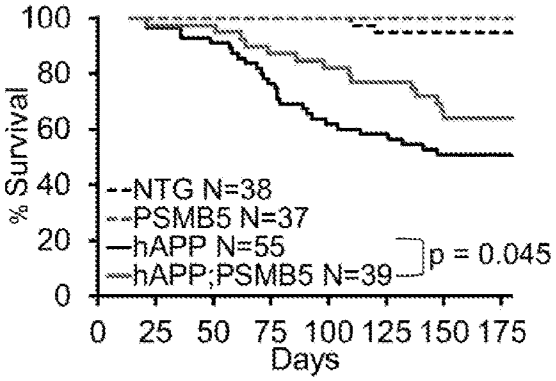

To establish if proteasome overexpression could protect against Alzheimer's disease-like deficits in a mouse model of Alzheimer's disease, NSE-PSMB5 was crossed with hAPP(J20) (Mucke, L. et al. *J Neurosci* 20, 4050-4058 (2000)) mice which overexpress familial-mutant human APP and recapitulate aspects of Alzheimer's disease pathogenesis (Wright, A. L. et al. *PLoS One* 8, e59586, doi: 10.1371/ journal.pone.0059586 (2013); Hong, S. et al. *Science* 352, 712-716, doi:10.1126/ science.aad8373 (2016); Cheng, I. H. et al. *J Biol Chem* 282, 23818-23828, doi: 10.1074/ jbc.M701078200 (2007); and Saganich, M. J. et al. *J Neurosci* 26, 13428-13436, doi:10.1523/ JNEUROSCI.4180-06.2006 (2006)) (FIG. 2G). At 7-8 months, hAPP (J20) mice displayed deficits in spatial learning and memory based on Morris water maze with probe reversal (more cognitively challenging variant). In the probe reversal trial, a significant decline in spatial memory in hAPP(J20) mice was observed; this deficit was prevented in hAPP(J20) mice with enhanced neuronal proteasome function (FIG. 2H). hAPP(J20) mice also had a trend for higher thigmotaxis and greater latency which were reduced with enhanced neuronal proteasome function (FIG. 2I). As a secondary measure, working memory through Y-maze and spatial memory through Novel Object Recognition was evaluated. In both assays, a significant improvement with enhancement of proteasome function in hAPP(J20) mice (FIGS. 2J,K) was observed. However, for these two measures, it was not possible to determine if this represented protection against Alzheimer's disease-related deficits or cognitive benefits produced by enhanced proteasome function independent of the disease model. (FIGS. 2J,K). As well as improved learning and memory, mice also displayed reduced Alzheimer's disease-related mortality. In this genetic background, hAPP(J20) mice display ≈50% mortality by 6 months. Littermates that overexpress proteasome in the hAPP(J20) background show reduced total mortality and delayed mortality occurrence (78% increase relative to hAPP(J20) at $75^{th}$ percentile) (FIG. 2L).

Figure 3A:
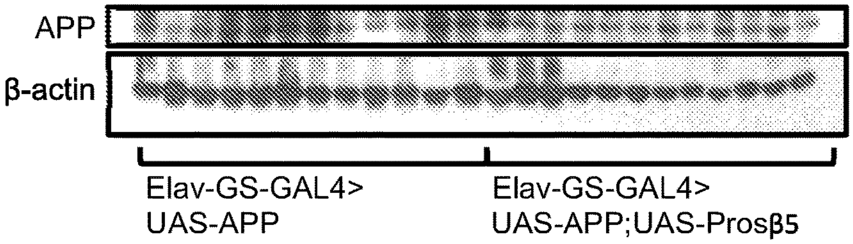
FIGS. 3A-G show PSMB5 overexpression increases degradation of APP.
Figure 3B:
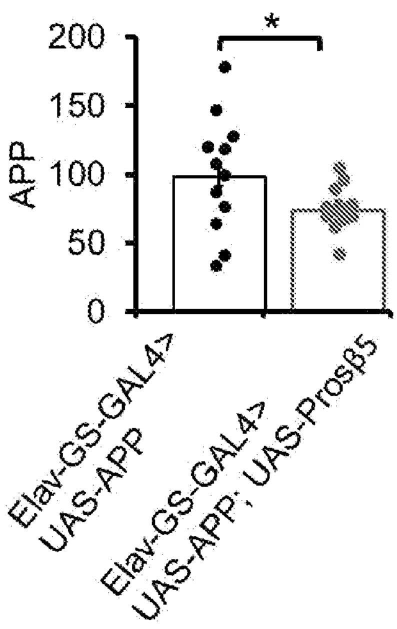
Figure 3C:
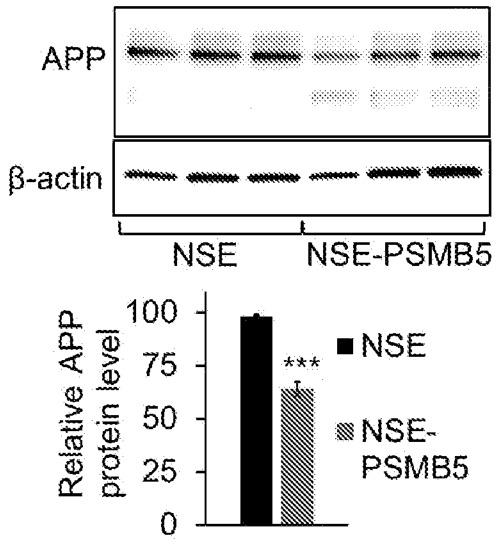
Figure 3D:
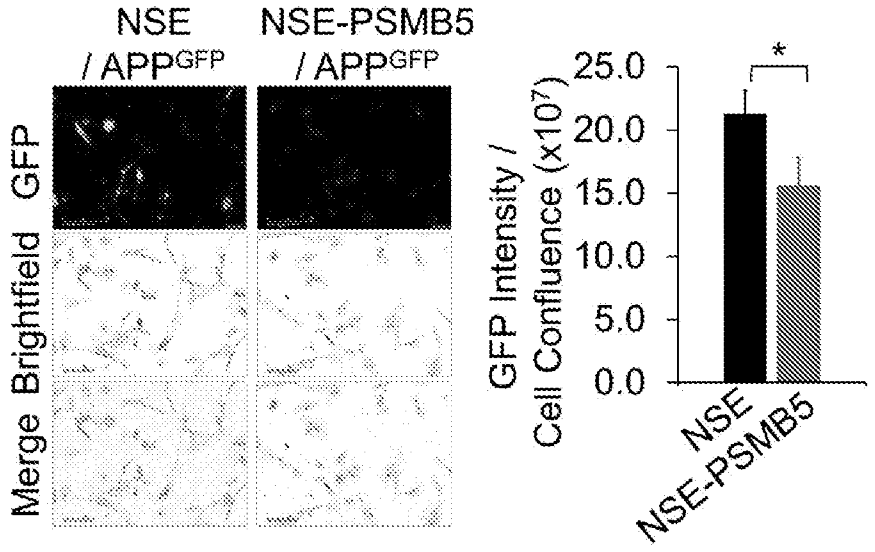
Figure 3E:
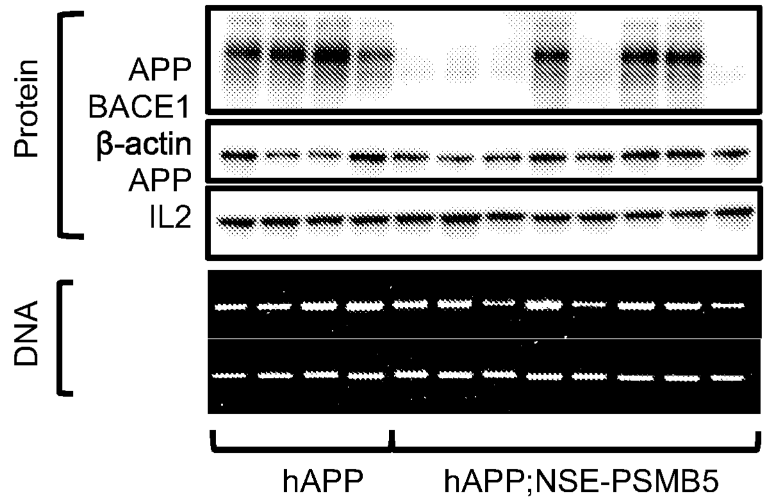
Figure 3F:
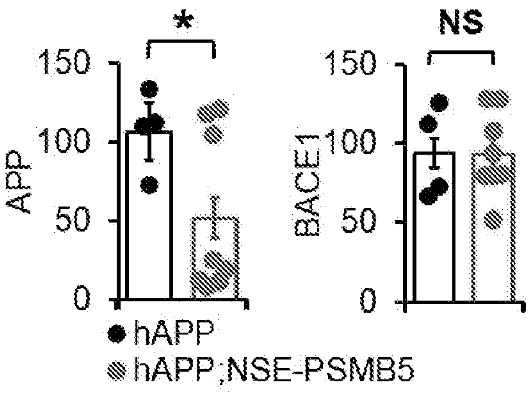
Figure 3G:
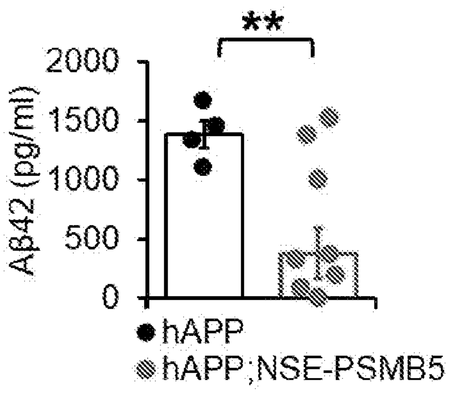

The proteasome protective effects may stem from degradation of the Aβ precursor machinery and substrate. Previous reports have shown APP, BACE1 and γ-secretase activating protein GSAP are degraded by the proteasome, and treatment of cells with proteasome inhibitors increases BACE1 and GSAP (Qing, H. et al. *Faseb J* 18, 1571-1573, doi:10.1096/ fj.04-1994fje (2004); Nunan, J. et al. *J Neurosci Res* 74, 378-385, doi:10.1002/ jnr.10646 (2003); and Chu, J., et al. *J Neurochem* 133, 432-439, doi:10.1111/ jnc.13011 (2015)). Enhancing proteasome function in flies that overexpress hAPP and hBace1 resulted in significantly less detectable APP protein (FIG. 3A-B) despite no change in mRNA (FIG. 1F inset). Transfection of SK-N-SH neuroblastoma cells with NSE-PSMB5 reduced levels of APP levels, cells also showed a lower MW band which may represents a cleavage product (FIG. 3C). Furthermore, a reduction in fluorescence in $APP^{GFP}$ transfected cells when co-transfected with NSE-PSMB5 was observed (FIG. 3D). Additionally, despite showing presence of the hAPP transgene we were unable to detect hAPP protein in 5/8 NSE-PSMB5; hAPP(J20) mice evaluated we hypothesize that this represents high levels of turnover of hAPP in these mice (FIG. 3E-F). These animals also show reduced level of the 42AA β-amyloid variant (FIG. 3G).

Figure 4A:
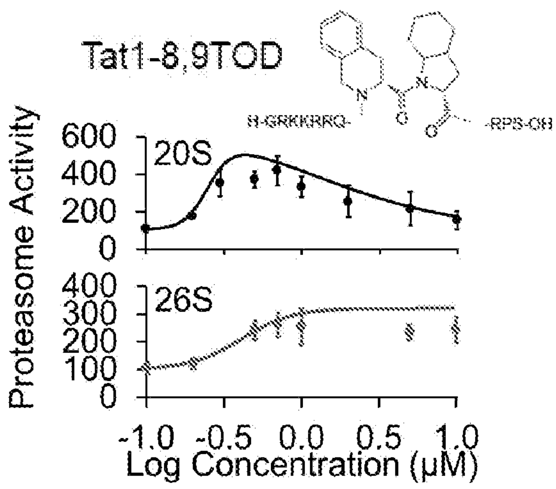
FIGS. 4A-L show TAT1-8,9TOD and TAT1-DEN enhance both 20S and 26S proteasome while reducing cell death, cognitive deficits and abundance of Aβ machinery in fly, cell culture and mouse models of Alzheimer's disease.
Figure 4B:
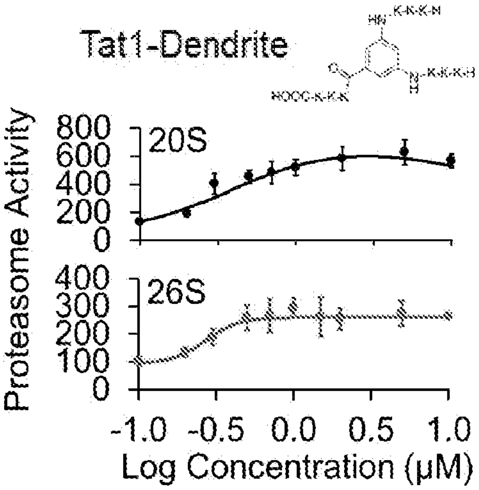
Figure 4C:
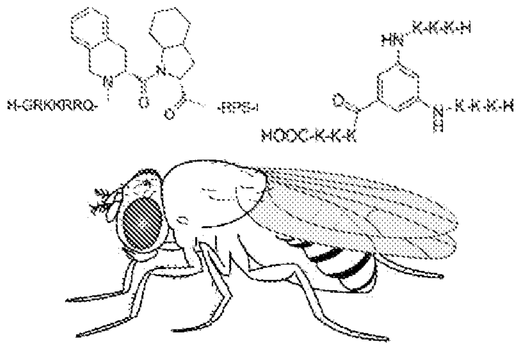

Next, it was determined whether pharmacologic manipulations which enhance proteasome function could also reduce Alzheimer's disease-like symptom presentation and progression. A set of peptidomimetics which activate the proteasome were developed. The design was based on proteasome-binding fragments of the viral protein HIV-1 Tat (Jankowska, E. et al. *Biopolymers* 93, 481-495, doi:10.1002/ bip.21381 (2010)), which shares a short proteasome binding motif with the 11S/REG/PA28 natural proteasome activator (Huang, X. et al. *J Mol Biol* 323, 771-782, doi:10.1016/ s0022-2836(02)00998-1 (2002)). Since proteasome activated with 11S takes significant part in the cellular immune response, the viral protein uses competition with 11S as a part of its anti-immune response strategy (Huang, X. et al. *J Mol Biol* 323, 771-782, doi:10.1016/ s0022-2836(02) 00998-1 (2002)). While Tat1 inhibits the artificially activated core proteasome (Witkowska, J., et al. *J Pept Sci* 20, 649-656, doi:10.1002/ psc.2642 (2014); and Karpowicz, P. et al. *PLoS One* 10, e0143038, doi:10.1371/ journal-.pone.0143038 (2015)), its physiological relevance lies in the ability to activate the native latent core (Jankowska, E. et al. *Biopolymers* 93, 481-495, doi:10.1002/ bip.21381 (2010)). A peptidemimetic composed of the 12AA proteasome binding region was generated. A peptide, Gly48-Arg58, is a well-known 'cell-penetrating-peptide' with blood-brain-barrier-passing capacity due to its highly positive charge and peculiar structure. The 12AA-residue is not sufficient to carry the transcription-stimulating functions of the full-length HIV-1 Tat protein (Ray, A. S. *AIDS Rev* 7, 113-125 (2005)). This positioned Tat1 peptide as an attractive lead for design of proteasome agonists with excellent absorption ability. The compositions disclosed herein have an improved proteasome-targeting efficiency and are more stable. Previous work indicated the potential presence of two structural turns (Jankowska, E. et al. *Biopolymers* 93, 481-495, doi:10.1002/ bip.21381 (2010)). Destabilizing the turns by Ala-walking or stabilizing by introduction of synthetic turn-inducers led to the following the pharmacophore: a hook-like structure with a strongly positively charged peptide moiety connected by a β-type turn to short peptide fragment (Karpowicz, P. et al. *PLoS One* 10, e0143038, doi:10.1371/ journal.pone.0143038 (2015)). Synthetic stabilization of the turn bestowed resistance to degradation by the proteasome to the peptidomimetic, TAT1-8,9TOD (Karpowicz, P. et al. *PLoS One* 10, e0143038, doi:10.1371/ journal.pone.0143038 (2015)), which appeared to strongly activate in vitro the "workhorse" chymotrypsin-like activity of both latent 20S and assembled 26S proteasome (FIG. 4A) (Osmulski, P. et al. Molecules (2020) March; 25(6): 1439). The activation of 26S proteasome was not an effect of the 20S core stimulation after a hypothetical 26S disassembly (Osmulski, P. et al. Molecules (2020) March; 25(6): 1439)). Further attempts to modify the Tat fragment lead to the basic sequence shortened to triple-Lys but multiplied to three fragments joined by aminobenzyl (Tat-Dendrite; which appeared to be an excellent activator of 20S and 26S proteasomes (FIG. 4B) (Osmulski, P. et al. Molecules (2020) March; 25(6): 1439)).

Figure 4D:
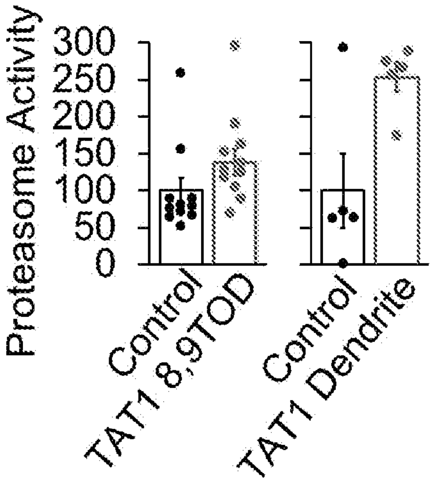
Figure 4E:
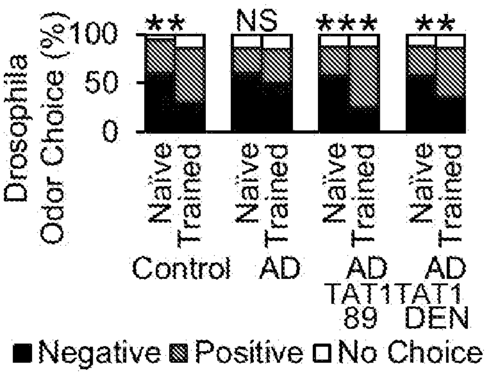
Figure 4F:
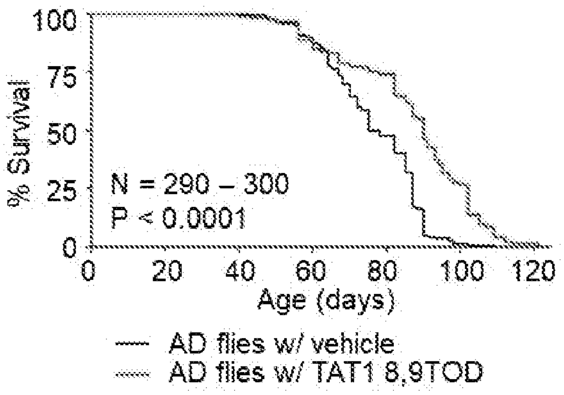

The in vitro results indicate strong activation of the proteasome, thus, the next step was to establish the efficacy of the compounds disclosed herein in an Alzheimer's disease model. The compounds disclosed herein showed increased proteasome activity in flies (FIG. 4D). Further, when fed to a fly model of Alzheimer's disease, the compounds reduced Alzheimer's disease-like deficits in associative learning (FIG. 4E) and mortality (FIG. 4F).

Figure 4G:
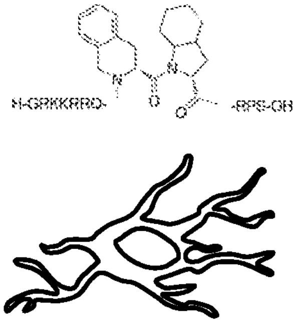
Figure 4H:
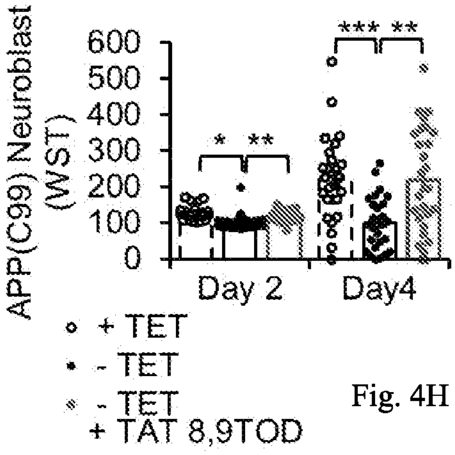
Figure 4I:
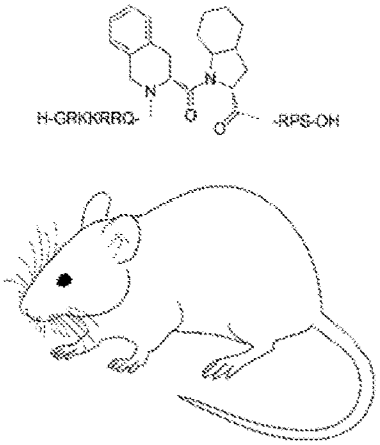
Figure 4J:
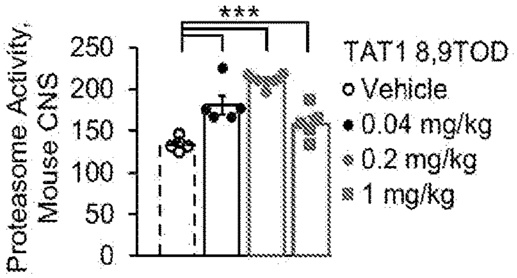
Figure 4K:
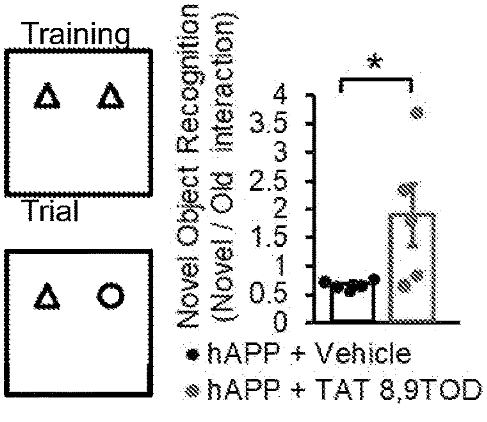
Figure 4L:
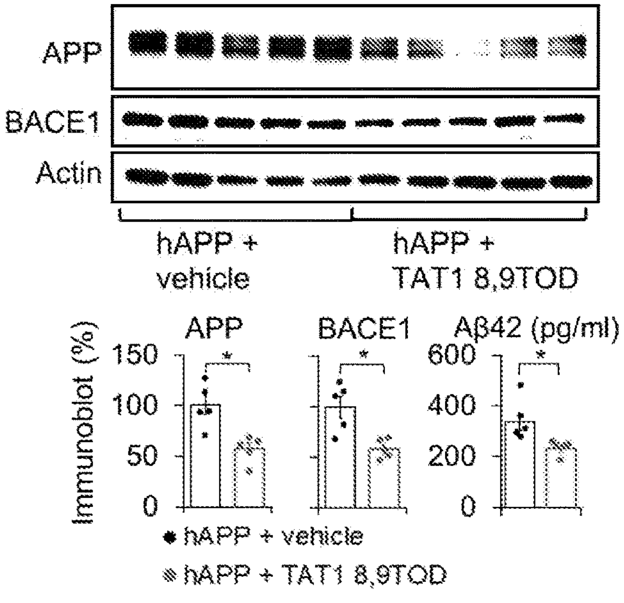

Next, TAT1-8,9TOD was tested. The results showed that treatment of the TET-OFF $APP^{N17-C99}$ overexpression cell line MC65 reduced Alzheimer's disease-like cell death (FIGS. 4G, H). The results demonstrated that TAT1-8,9TOD stably penetrates the blood-brain-barrier and enhances proteasome function in the brains of mice (FIG. 4I-J). Next, a cohort of 6 month old hAPP(J20) mice were subjected to 14 days treatment with TAT1-8,9TOD. This reduced deficits in associative learning in the mice (novel object recognition assay) (FIG. 4K). This was associated with and likely driven by a decline in both APP and BACE1 protein levels and a resultant reduction in Aβ42 levels (FIG. 4L).

These findings demonstrate the capacity of proteasome augmentation as a germane target for treatment of Alzheimer's disease-like symptoms in a range of model systems. The proteasome activating peptide mimetic TAT1-8,9TOD can be used as pharmacologic treatment. The findings also show that proteasome protective effects stem at least in part from increased degradation of Aβ machinery/substrate.

Experimental Procedures.

Fly Lines and Strain Maintenance. UAS-ProsBeta5 (Staudt, N. et al. *PLoS Genet* 1, e55, doi:10.1371/ journal.pgen.0010055 (2005)) and Elav-GS-GAL4; UAS-hAPP; UAS-hBACE1 (56756) stocks were obtained from the Bloomington *Drosophila* Stock Center (NIH P40OD018537). The lines were maintained on agar-cornmeal-dextrose-yeast growth media (Ren, C., Finkel, S. E. & Tower, J. *Exp Gerontol* 44, 228-235, doi:10.1016/ j.exger.2008.10.002 (2009)) in a humidified 24° C. incubator with 12:12-hour light:dark cycle. The crosses were set up with female virgins of the respective GAL4 driver line and male UAS-ProsBeta5 or $W^{1118}$ flies. Progeny were collected within 48 hours of eclosion and allowed to mate on 10% sugar/yeast (SY10) media (Skorupa, D. A., et al. *Aging Cell* 7, 478-490, doi:10.1111/ j.1474-9726.2008.00400. x (2008)) for another 48 hours. After this period, females were separated and sorted into sets of 25 flies per vial containing SY10 media supplemented either with 400 μM mifepristone (RU486) or ethanol vehicle, mixed directly into the food. 8 μM Blue Dye #1 was added to food containing RU486 for the purpose of identification. Carbon dioxide was used to briefly anesthetize flies for sorting. Flies were moved to vials of fresh media every two to three days.

Cell culture. Cells were cultured in EMEM (SK-N-SH), DMEM (MC65) supplemented with 10% heat-inactivated fetal bovine serum and antibiotics (100 U $mL^{-1}$ penicillin, 100 μg $mL^{-1}$ streptomycin, and 0.25 μg $mL^{-1}$ of amphotericin B; Gibco-Invitrogen). Incubators were maintained at 5% $CO_2$, and 37° C. Medium was replaced every 3-4 days. For most experiments, cells were seeded at 100,000 cells $mL^{-1}$ in either 6-well or 96 well plates 24 h prior to assay. In most cases, media was replaced with serum free optimem media 24 h prior to assay.

Transfections and imaging. Cells were seeded at 75,000 cells per well in 6 well plates. They were transfected the day after with 1.4 μg of NSE-PSMB5 vector or NSE empty vector control plus 1 μg of GFP-APP vector per well using Lipofectamine LTX and Plus reagent (Thermofisher #15338030) following manufacturer's instructions. Cells were passaged to a 96 well plates the day after transfection for some experiments. Cells were imaged with the Incucyte system (Sartorius) and images were analyzed with manufacturer's software for GFP Fluorescence intensity normalized by cell confluence.

NSE-PSMB5. A full length mouse PSMB5 plasmid was utilized (MR203485, Origene), PSMB5 was excised removing the Myc-DDK-tag, and cloned into the ShuttleNSE empty vector (50958, Addgene) (Mi, J. et al. *PLoS One* 8, e83609, doi:10.1371/ journal.pone.0083609 (2013)) adjacent to the NSE promoter. The NSE-PSMB5 region was excised and microinjected into (C57BL/6 X SJL)F2 mouse eggs by the University of Michigan Transgenic Animal Model Core. Mice were then bred into a C57BL/6J Background for 3 generations. The mouse is still in a mixed background which may confound some of the outcome measures. To control for this, the experimental comparisons were made between littermates.

Mice. hAPP(J20) (Mucke, L. et al. *J Neurosci* 20, 4050-4058 (2000); Hsia, A. Y. et al. *Proc Natl Acad Sci USA* 96, 3228-3233, doi:10.1073/ pnas.96.6.3228 (1999); Roberson, E. D. et al. *Science* 316, 750-754, doi:10.1126/ science.1141736 (2007)) and NSE-PSMB5 mice were maintained by heterozygous crosses with C57BL/6J mice (Jackson Laboratories, Bar Harbor, Me.). Non-transgenic littermates were used as controls. Animals were house in ventilated cage racks under with up to 5 animals per cage under 12 hr light/dark cycles at 24° C. Animals received daily monitoring by Laboratory of Animal Research (LAR) staff and were transferred to new cages weekly.

Quantitative PCR. mRNA was isolated using standard Trizol method and cDNA prepared using High-capacity cDNA reverse transcriptase kit (Applied Biosystems). Quantitative PCR was carried out using SYBR Green and normalized to beta-actin.

Plate-based proteasome activity assay. Samples were homogenized by pestle in 100 μL chilled proteasome buffer (50 mM Tris, 5 mM MgCl2, 1 mM DTT, pH 7.4, vortexed and then centrifuged at 21,000 g at 4° C. for 15 minutes and supernatant transferred. Protein content was recorded by Bradford assay and samples diluted as appropriate. In a black 96-well plate, 10 μL of samples were added to 80 μL proteasome buffer supplemented with addition of 5 mM ATP for measuring 26S proteasome activity. Finally, 50 μM Suc-LLVY-AMC fluorogenic substrate in 10 μL proteasome buffer was added to each well to measure chymotrypsin-like activity. The plate was incubated at 37° C. in a SpectrumMax M2 plate reader for four hours with fluorescence measured every 10 minutes with 355 nm excitation and reading 460 nm emission. Total proteasome activity per sample was defined as the gradient of the linear trendline over this incubation period.

*Drosophila* lifespans. Flies were transferred to fresh media and survival scored every two to three days. dLife software (Linford, N. J., et al. *J Vis Exp*, doi:10.3791/50068 (2013)) was used to record survival and to compare median and maximum lifespan via Logrank analysis. Vials were randomized in terms of tray position and semi-blinded to reduce impacts of environment or investigator bias.

Olfactory aversion training. Experiments were performed broadly (Malik, B. R. & Hodge, J. J. *J Vis Exp, e*50107, doi:10.3791/50107 (2014)). Animals were exposed (via an air pump) in alternation to two neutral odors (3-octanol and 4-methylcyclohexanol, prepared as a 1/10 dilution in mineral oil) for 5 minutes under low red-light and a 100V 60 Hz shock was applied during exposure to one of the two odors. The odor associated with the electric shock was alternated between vials. After three training rounds per odor, animals were given one hour to recover then placed in a T-maze (Celexplorer labs) with opposing odors from either side. Flies were allowed two minutes to explore the maze after which the maze sections were sealed and the number of flies in each chamber scored.

Spontaneous activity and circadian rhythm. Spontaneous activity was monitored using a Trikinetic activity monitor, in which vials containing 20-25 flies were secured and activity recorded in a humidified 24° C. incubator with 12:12-hour light:dark cycles as described herein. Flies were allowed to acclimate for 8 hours prior to data collection. Activity was averaged for each twelve-hour cycle and normalized per fly.

Cell viability. Cell maintained in a clear 96 well plate. On the day of assay, 10 μl of WST-1 reagent (11644807001, Sigma Aldrich) was added to each well and cells incubated in a 37° C. 5% CO2 incubator for 2-4 hours. Absorbance was measured at 450 nm using a gemini series spectrophotometer.

Morris water maze (MWM) (Morris, R. *J Neurosci Methods* 11, 47-60 (1984); Galvan, V. et al. Reversal of Alzheimer's-like pathology and behavior in human APP transgenic mice by mutation of Asp664. *Proc Natl Acad Sci USA* 103, 7130-7135, doi:10.1073/ pnas.0509695103 (2006); Butterfield, D. A. et al. *Free Radic Biol Med* 48, 136-144, doi:10.1016/ j.freeradbiomed.2009.10.035 (2010); and Pierce, A. et al. *J Neurochem* 124, 880-893, doi:10.1111/ jnc.12080 (2013)). This test provides measures of hippocampal-dependent spatial learning and memory. Animals are given a series of 4, 1 min trials, 20-30 min apart, per day for 5 days to find a submerged platform (~1.5 or 1 cm below water level respectively) in a large tank (210 and 120 cm in diameter respectively) filled with opaque white-colored water at 24.0±1.0° C. surrounded by panels with geometric black and white designs that serve as distal cues. At the end of training, a probe trial in which the platform is lowered so that it is not available is administered to measure retention of the former platform location. The time each animal spends in the former location of the platform, the number of passes over that location provide a measure of memory. At the end of the probe trial, the platform will be raised to its previous location to maintain response-reinforcement contingency. Time-at-testing for groups will be alternated daily. Intertrial time will be ~30 min. On week 2 of training, reversals are performed, followed by a probe trial. Data is collected using TopScan (CleverSys) or Noldus EthoVision by operators blinded to genotype and treatment.

Y maze. Working memory is assessed by placing animals in a Y-shaped maze made of black Plexiglas with 3 arms, with equal angles between all arms. Each animal is placed in a pseudo-randomized arm of the maze and allowed to move freely around the apparatus, while the sequence and number of arm entries for each animal per minute for a 5-min period is recorded using TopScan (CleverSys) software. The percentage of movements in which the three arms were represented (ABC, CAB, or BCA, but not BAB) is calculated, as well as alternations among arms, to estimate short-term memory of the last arms entered. The total number of possible alternations is the number of arm entries minus two. Additionally, the total number of arm entries is an indicator of activity.

Novel object recognition test. To measure recognition of a previously encountered object, animals are placed in an opacified rat cage with bedding for 10 min. The following (training) day, mice are returned to the chamber, which now contains two identical objects, and allowed to explore the arena for 5 minutes. Percent of time exploring each object is recorded using TopScan. During testing (4 hours after training) one of the objects in the box is replaced with a new object and the side of the replaced object randomized amongst animals. Mice are given 5 mins to explore the two objects, and percent time exploring each object is recorded using TopScan. A discrimination ratio calculated as $(t_{novel}-t_{familiar})/(t_{novel}+t_{familiar})$ is used as a measure of retention of the priorly encountered object (positive and negative discrimination ratio values indicate a preference for exploration of the novel and familiar objects, respectively).

Statistics. Morris water maize was evaluated by two-way ANOVA followed by Tukey posthoc test. Y-Maze was evaluated by Two-way ANOVA followed by Bonferoni posthoc test. Olfaction Aversion Training was evaluated by Chi Squared. Lifespan analyses were evaluated by Log Rank investigation. Where not states statistical evaluations were performed by Student's T-Test.

Example 2

Tat Based Peptides Activate 20S and 26S Proteasome

Abstract. Proteasome is an element of controlled proteolysis responsible for catabolic arm of proteostasis. A proteasome can be a target for inhibition of its peptidolytic activities. This mechanism is utilized in clinical treatment of blood cancers because of a comfortable window of proteasome dependency of normal and cancerous cells. The latter are often addicted to proteasome activity as a motor of their high proliferative and metabolic capacity. The results described herein show that substantial augmentation of proteasome activity with specific pharmacological interventions can be achieved with Tat peptides leading to positive responses in symptoms of Alzheimer's disease in fly and mouse models. Described herein, is the molecular basis of proteasome activation with Tat derived peptides. It was tested whether an activation anchor responsible for upregulation of catalytic activity via allosteric signaling is connected via a β turn inducer to a specificity clamp that binds on an α surface of 20S proteasome achieving the proper location on α1 subunit. Elements that potentially control these effects were evaluated and mechanistic consequences of Tat binding to the α3 groove of proteasome is discussed herein.

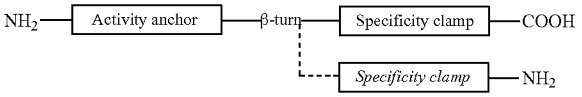

Docking of Tat-TOD scaffold to the α ring of 20S proteasome shows preferential peptide binding in a groove between α1 and α2 subunits. The activity anchor penetrates deep between the subunits, whereas the specificity clamp is positioned on the surface of α1 subunit by the β turn. A block scheme of Tat1 derivatives showing position of the activity anchor connected to the specificity clamp through a β-turn. Tat-Den is built from three identical blocks playing roles of specificity clamps and activity anchors.

Tat proteins. Full length HIV-1 Tat protein stimulates transcription from a viral promoter by binding to the TAR hairpin of the RNA transcript. It functions as a transcriptional transactivator that increases the production of the full length viral RNA. Binding to TAR is mediated by a 10 residue long basic region of Tat that maps in part to Tat1 peptide. However, for regulatory function such as binding to elements of the transcriptional complex, Tat protein requires its 47 long N-terminal domain encompassing an acidic and cysteine rich domains and hydrophobic core (Ray A S. AIDS Rev [Internet]. 2005; 7(2):113-125). The basic domain has a helical structure when built into Arginine Rich Motif RNA binding protein (ARM) such as Tat. This structure is apparently not preserved in the excised peptide. On this basis, it was assumed that this important function of Tat protein is not sustained in Tat1 peptide.

Tat protein fragments. Conformationally constrained peptides, in context of proteasome binding and regulation.

Means to activate proteasome (Myeku N, Duff K E. Trends Mol Med [Internet]. Elsevier; 2018 Jan. 11; 24(1): 18-29). (1) Natural activators of proteasome: phosphorylation, inhibition of DUBs (USP14 inhibitors) (Peth A, et al. Mol Cell. 2009 December; 36(5):794-804; and Lee B-H, et al. Nature [Internet]. 2010 September [cited 2015 Feb. 13]; 467(7312):179-184), clearance (Boland B, et al. Nat Rev Drug Discov [Internet]. 2018 Aug. 17; 17:660).(2) Natural protein modules—activators (e.g., PA28/ REG/11S, PA200/ Blm10, 19S). (3) Detergent (low concentration of sodium dodecyl sulfate; SDS). (4) Synthetic small molecule activators.

Incorporation of Tic (1,2,3,4-tetrahydroisoquinoline-3-carboxylic acid) and Oic (octahydroindole-2-carboxylic acid) residues into bradykinin sequence was applied to achieve structurally constrained peptides for study on a bradykinin receptor (Chakravarty S, et al. J Med Chem [Internet]. 1993 Aug. 20; 36(17):2569-71; and Kyle D J, et al. J Med Chem [Internet]. 1991 August; 34(8):2649-53). Extensive studies were carried on antimicrobial peptides that incorporated Tic Oic moieties showing promising actions toward select agents (Hicks R P. Bioorg Med Chem [Internet]. 2016; 24(18):4056-4065).

Application of β turn inducers to disrupt protein-protein interactions was explored for example in the case of a tyrosine kinase receptor (Burgess K. Acc Chem Res [Internet]. 2001 October; 34(10):826-35; and Larregola M, et al. J Pept Sci [Internet]. 2011; 17(9):632-643).

Conformational analysis of the Tic containing tripeptide antagonist of opioid receptor showed that L and D variants of the peptide always produced compact structures but pointing at the opposite site of the Tic residue (Wilkes B C, Schiller P W. Biopolymers [Internet]. 1994 September; 34(9):1213-1219). This change in the structure produced highly specific antagonists of δ or μ receptors, respectively. Tic is also used as a substitute for a planar amino acid such as tryptophan in tetrapeptide as a ligand of melanocortin receptor (Schlasner K N, et al. Molecules [Internet]. MDPI; 2019 Apr. 13; 24(8):1463).

Results and Discussion. The tested peptides (FIG. 5) affected ChT-L activity of human housekeeping proteasome in a dose dependent manner (except 3A-TO-3A, see below). Other two peptidase activities were poorly or non-responding to the presence of the peptides.

Figure 6:
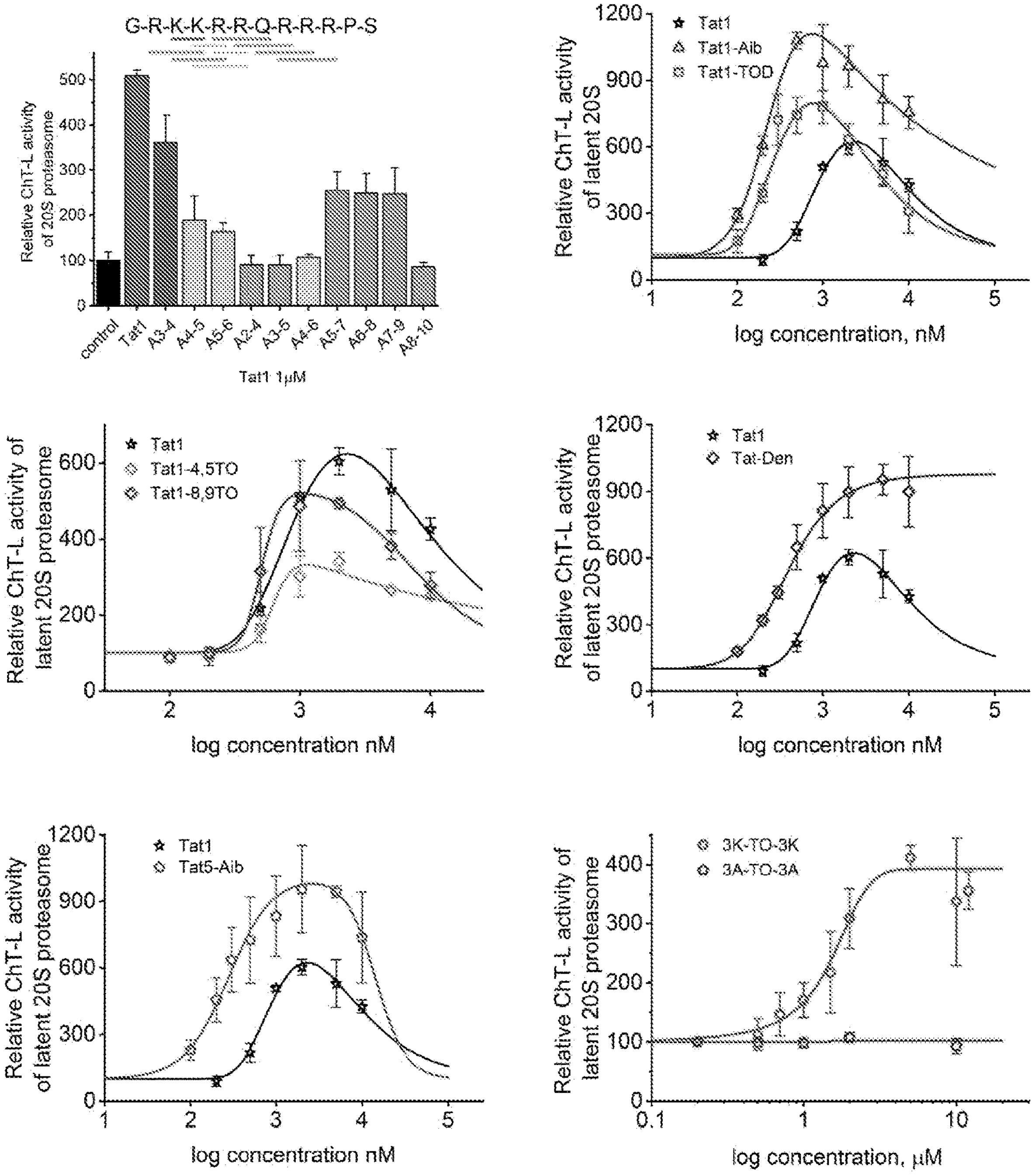
FIG. 6 shows that the chymotrypsin-like activity of latent human 20S proteasome is activated by Tat1 peptide derivatives in a dose dependent manner. Top left panel: Peptides (1 μM) with selected residues replaced by alanines were tested for their activating abilities; The sequence for Tat1 fragment is shown as GRKKRRQRRRPS (SEQ ID NO: 1).
Figure 7:
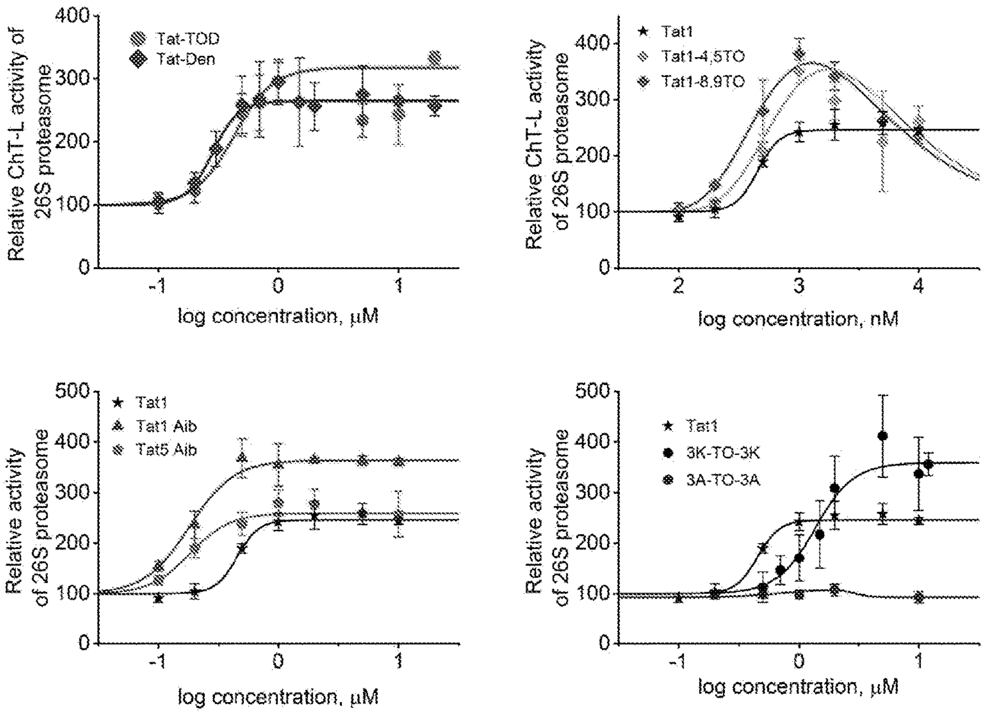
FIG. 7 shows that the chymotrypsin-like activity of human 26S proteasome is activated by Tat1 peptide derivatives in a dose dependent manner.

Tat1 (GRKKRRQRRRPS; SEQ ID NO: 1) activated 20S proteasome 7 fold and 2 fold 26S proteasome (Table 1). Surprisingly, an AC50 parameter (a peptide concentration at which the half of maximum activation effect was measured) was lower for 26S than for 20S proteasome (Table 1). Substitution of a single residue of Tat1 with Ala along the whole length of the sequence showed a weak decrease of activating capabilities of ChT-L activity. A substantial drop of this potential was noted when two consecutive residues were substituted with Ala residues at positions from 3 to 6. Moreover, an elongation of the Ala stretch to 3 residues led to a complete abrogation of proteasome activation (FIG. 6A). A region 5-9 was less prone to Ala caused disturbance, however, a region 8-10 responded with complete loss of activation. It was concluded that the Tat1 activation potential is associated with two regions: 2-5 and 8-10 (FIG. 6A). These observations are in agreement with published results of molecular dynamics studies of Tat1 (Karpowicz P, et al. PLoS One [Internet]. 2015 November; 10(11):e0143038). They showed that the peptide backbone tends to preferentially form β-type turns in positions 4,5 and 8,9. Therefore, a series of peptide derivatives were prepared, where several β-turn inducers were introduced in these positions. TO and TOD groups were first introduced separately and ChT-L of 20S and 26S proteasome were measured in the presence of these peptides. The TO substitutions produced rudimentary better activators of 20S proteasome but better activators of 26S when compared the activation folds. Interestingly, the TOD substitution at the position 8,9 generated a much better activator of 20S proteasome with a very low AC50 (220 nM) but the disappointingly poorer 26S activator (Table 1, FIGS. 6, 7). However, promotion of turns in both positions 4,5 and 8,9 (Tat1 4,5 TO 8,9 TOD) did not support proteasome activation beyond about 60% at 10 μM concentration. It was concluded that orientation of the β-turn influences interactions of Tat1 with the binding domain and that TOD supports such binding better than the TO moiety, in a full agreement with molecular dynamics showed preferred conformation of the Tat1 peptide (Karpowicz P, et al. PLoS One [Internet]. 2015 November; 10(11):e0143038).

Figure 8:
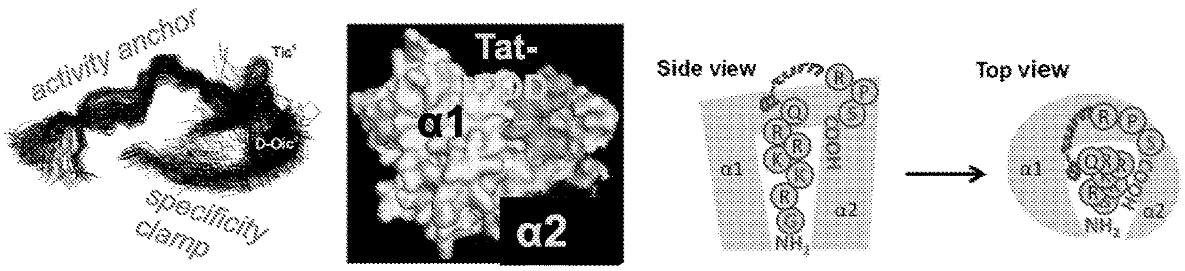
FIG. 8 shows molecular docking indicates the preferred binding site of Tat-TOD on the a face of the 20S proteasome, in the pocket between subunits α1 and α2. From the left: molecular dynamics structure of Tat-TOD[13]; molecular docking of Tat-TOD binding to the 20S proteasome (5le5). Only 10 Å vicinity of the ligand is shown. Right-cartoon demonstrating the positioning of Tat-TOD in the pocket.

These observations were further confirmed by the docking of Tat-TOD scaffold to the α ring of 20S proteasome that shows preferential peptide binding in a groove between α1 and α2 subunits (FIG. 8). In this model, the activity anchor penetrates deep between the subunits, whereas the specificity clamp is positioned on the surface of α1 subunit by the β turn. A block scheme of Tat1 derivatives shows a position of the activity anchor connected to the specificity clamp through a β-turn inducer.

Next, Aib-Gly was introduced as a turn inducer at positions 8,9. This modification led to formation of a superior activator of both 20S and 26S proteasome with AC50 below 200 nM and 11 fold activation for 20S. The replacement of the C terminal (R-P-S; 10-12) sequence with a reversed N-terminal 1-8 sequence (Tat5-8,9Aib), created a surprisingly excellent activator slightly less potent than Tat1-8, 9Aib. These results show that a relatively slight stiffening of the peptide with the Aib-Gly moiety improves peptide capability to interact with binding site. The lack of the specificity clamp (RPS) does not influence AC50, although it diminished the activating potential slightly.

These peptides competed with pRpt3 peptide (KDEQEHEFYK; SEQ ID NO: 2) for binding site, a 10 residue C-terminal fragment of Rpt3 protein which forms with other 5 ATPases a ring on the α face of 20S proteasome responsible for unfolding and threading substrates into the axial channel of the protease.

To determine if a simplified sequence of Tat1 can retain activating potential, TO peptides decorated with 3 lysines or 3 alanines on its both sides were prepared. The 3A-TO-3A peptide was totally inactive, whereas 3K-TO-3K retained substantial activating capabilities but with a disappointingly high AC50. This peptide is also a poor competitor with pRpt3 peptide that binds into the same pocket. Surprisingly, an additional 3K sequence but decorating a benzoyl moiety (creating Tat1-Den with three 3K peptides in a star like orientation) produced one of the best proteasome activators. It was concluded that a three-lysine sequence is sufficient to activate proteasome, however, activation occurred in the presence of an actual clamp formed by two other 3K sequences (Table 1, FIGS. 5-7).

Titration of latent 20S proteasome with most of the tested peptides presented a clear maximum after which a decrease in the activation was noted. Based on the fitted traces it seems that the activation may never drop to 100% since it would call for physically unachievable peptide concentrations. Tat-Den was a sole exception to this rule and likely reached a saturating effect. This type of response was characteristic for 26S proteasome with the following exceptions: Tat1-4,5TO and Tat1-8,9TO. The titration traces resembled in these cases those observed with 20S proteasome. It was then tested whether the maximum peak type response may correspond to the effect of occupancy at other binding sites where affinity or specificity is substantially lower. Likely, it does not correlate with potential competition with the substrate since Tat1 is digested by 20S proteasome and Tat1-8,9TOD is resistant to degradation.

TABLE 1

Peptides based on HIV-1 Tat protein fragment, Tat1, are potent activators of the proteasome. $AC_{50}$: concentration at which the compound reaches 50% of the maximal activation effect. Chymotrypsin-like (post-hydrophobic) peptidase activity of the proteasome was measured with model fluorogenic peptide substrate Suc-LLVY-MCA, with human purified housekeeping 20S and 26S proteasomes (Boston Biochemicals).

| | 20S proteasome | | 26S proteasome | |
|---|---|---|---|---|
| compound | $AC_{50}$ [nM] | Max activation fold | $AC_{50}$ [nM] | Max activation fold |
| Tat1 | 710 | 6.2 | 453 | 2.5 |
| Tat1-8, 9 TOD | 221 | 7.8 | 424 | 3.2 |
| Tat1-4, 5 TO | 602 | 3.3 | 489 | 3.5 |
| Tat1-8, 9 TO | 499 | 5.2 | 348 | 3.6 |
| Tat1-Den | 374 | 9.6 | 281 | 2.6 |
| Tat1-8, 9 Aib | 194 | 11.1 | 180 | 3.6 |
| Tat5-8, 9 Aib | 183 | 8.9 | 184 | 2.6 |
| 3K-TO-3K | 1560 | 4 | 1368 | 3.6 |
| 3A-TO-3A | ND | 1.0 | ND | 1.0 |

Example 2

Peptide-Based Pharmacophore Activates 20S Proteasome

Abstract. The proteasome is an important element of controlled proteolysis, responsible for the catabolic arm of proteostasis. By inducing apoptosis, small molecule inhibitors of proteasome peptidolytic activities are successfully utilized in treatment of blood cancers. However, the clinical potential of proteasome activation remains relatively unexplored. Described herein are short TAT peptides derived from the HIV-1 Tat protein and modified with synthetic turn-stabilizing residues as proteasome agonists. Molecular docking and biochemical studies point to the α1/α2 pocket of the core proteasome α ring as the binding site of TAT peptides. It was tested whether the TATs' pharmacophore consists of an N-terminal basic pocket-docking "activation anchor" connected via a β turn inducer to a C-terminal "specificity clamp" that binds on the proteasome a surface. By allosteric effects—including destabilization of the proteasomal gate—the compounds substantially augment activity of the core proteasome in vitro. Significantly, this activation is preserved in the lysates of cultured cells treated with the compounds.

Figure 9A:
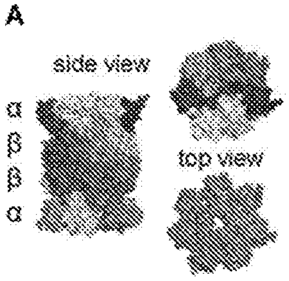
FIGS. 9A-C shows the human 20S core proteasome, Human Immunodeficiency Virus-1 (HIV-1) Transcriptional Activator TAR (Tat) protein and TAT1 peptide.

Introduction. As the central protease of the ubiquitin-proteasome pathway, the proteasome has long been considered an attractive target for drugs potentially affecting multiple aspects of cell physiology [1]. Indeed, small molecules targeting the proteasome have entered the clinic with great success [2]. However, their scope at present is very limited: the proteasome-modifying compounds currently approved or clinically tested as drugs are competitive inhibitors and are used to treat advanced blood cancers [1,3]. Turning to the opposite side of pharmacological intervention into the proteasome: augmentation of catalytic activity. Since dysfunction of proteasome-mediated controlled protein degradation is a hallmark of both cellular aging [4,5] and neurodegenerative diseases [6-9], enhancement of the enzyme's activity should be considered an attractive therapeutic option. The complex structure of the catalytic core 20S proteasome (the "core particle"; FIG. 9A) presents fascinating options for allostery-based augmentation [10,11]. The peptidase responsible for post-hydrophobic (chymotrypsin-like, ChT-L) cleavages is considered a rate-limiting "workhorse" and is the major target for inhibitors and activators alike [3,12]. Indeed, overexpression of a catalytic subunit harboring the active site of the ChT-L peptidase has been shown to extend lifespan as well as to reduce age-related cognitive decline in animal models [13-15]. However, reports on pharmacological augmentation are limited to in vitro and cell culture studies. [16-20].

Figure 9B:
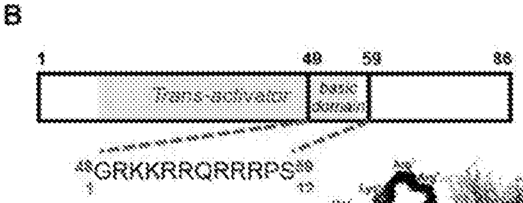
Figure 9C:

Described herein are a series of short, modified peptides based on the basic domain of the viral Human Immunodeficiency Virus-1 (HIV-1) Transcriptional Activator TAR (Tat) protein (FIG. 9B). Among many intracellular effects, the HIV-1 Tat protein inhibits the core proteasome [21]. It is noted that short peptide fragments of HIV-1 Tat displayed peculiar in vitro properties: they inhibited detergent-treated core particle but mildly activated the latent core [22-24]. However, treatment with sodium dodecyl sulfate detergent, although convenient for in vitro assays, yields mildly denatured proteasome and, under these far-from-physiological conditions, likely with destroyed natural allosteric routes [10]. Therefore, the activating properties of HIV-1 Tat protein-derived "TAT peptides" were assessed. After observing a strong in vitro proteasome augmentation by modified HIV-1 Tat-derived peptides, selected compounds were tested in cell culture. In a separate study, it was found that proteasome stimulation by TAT peptides partially prevented cognitive deficits and mortality in animal models of Alzheimer's disease [15]. The results showed increased proteasome-mediated turnover of amyloid precursor protein (APP) and β-secretase (which cleaves APP to generate β-amyloid peptide), concomitant with lowered levels of β-amyloid, lowered mortality and protection against cognitive decline [15].

Figure 10:
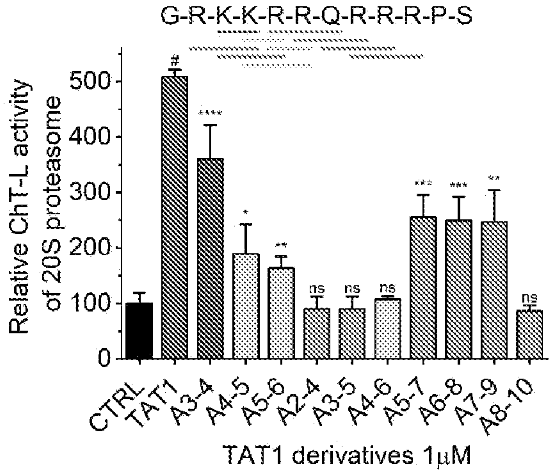
FIG. 10 shows TAT1 derived peptides (1 μM) with selected residues replaced by alanine were tested for their activating capabilities of the chymotrypsin-like (ChT-L) activity of human latent 20S proteasome. Activity of 20S proteasome in the absence of any TAT peptide (DMSO) was set at 100%. Mean and SD of three independent experiments are presented. Top: The amino acid sequence of TAT1 peptide (SEQ ID NO: 1) (1). Bars mark residues replaced by alanine. Green-like colors indicate no significant effect of the substitution, whereas orange-like colors mark hot spots resulting in loss of activation effect. Substitution of any single residue with alanine did not have a noticeable systematic effect on ChT-L activity. Columns show average+SD; *, $p<0.05$; , $p<0.005$; *, $p<0.0005$; ****, $p<0.0001$; #, $p<1\times10^{-7}$; ns: not significant; n=3-5, t-test performed against the activity of control, untreated 20S proteasome.

Results and Discussion. Design of TAT Peptides. A set of proteasome agonists were developed and designed to activate the proteasome in vitro, to support blood-brain-barrier (BBB) transition, and to stably augment the proteasome in the nervous system. This design was based on a basic domain of the Human Immunodeficiency Virus-1 (HIV-1) Transcriptional Activator TAR (Tat) protein $^{48}$GRKKRRQRRRPS$^{59}$ (TAT1 (SEQ ID NO: 1); (1)), which contains a proteasome-binding RTP (REG/Tat-proteasome-binding site) motif [26]. This RTP motif is shared with subunits of the endogenous PA28/ REG protein (proteasome activator/regulator with 28 kDa subunits; 11S), which targets pockets on the core proteasome α face [21] (FIG. 9A). These pockets are established allosteric hotspots and specific binding sites for the REG activator and, importantly for the Rpt (Regulatory Particle ATP-ase) subunits of the 19S component of 26S proteasome. This holoenzyme is the most advanced and physiologically involved among assemblies sharing the 20S proteasome catalytic core [28]. Beyond their proteasome-binding capacity, TAT peptides have a strong cell-penetrating potential: a fragment nearly identical to TAT1, $^{47}$Y-R$^{57}$, was reported as a "cell-penetrating-peptide" with high blood-brain barrier (BBB)-passing capacity due to its structure and highly positive charge [29]. Importantly, the basic domain extracted from the HIV-1 Tat protein context is devoid of either the transactivation or E3 recruitment capability of the viral factor [26,27,30] (FIG. 9B). The whole Tat protein inhibits the core proteasome and also competes with the PA28/ REG activator [21]. As mentioned above, it was found that TAT1 inhibits the artificially activated 20S core in vitro, and it can activate the naturally latent core [22-24]. The goal of the design described herein was to enhance the proteasome activation and improve the peptide's stability while preserving BBB penetrance. This goal was accomplished by generating structural derivatives of the TAT1 peptide that contained turn-inducing moieties and the preserved important basic residues (Table 2). Structural studies of the TAT1 peptide suggested a strong preference toward formation of two β-like turns in positions 4,5 and 8,9 [22,24] (FIGS. 9B, C). Substitutions of residues in TAT1 with alanines (Ala-walking) confirmed the significance of the putative turn regions for core proteasome activation (FIG. 10).

As the next step, the effects of introducing TO (Tic: L-1,2,3,4-tetrahydroisoquinoline-3-carboxylic acid, Oic: Octahydroindole-2-carboxylic acid), TOD (Tic D-Oic) or DABA (3,5-diaminobenzoic acid) as synthetic turn inducers in the important positions of TAT1 were assessed. Since the putative turn was flanked by predominantly basic sequences, the robustness of the design was explored by simplifying the Arg and Lys stretches to triple-Lys (Table 2).

TABLE 2

TAT1 derivatives explored in this study. Compounds (7) and (9) constitute negative controls.

| Compound | Structure |
|---|---|
| (1) TAT1 | GRKKRRQRRRPS (SEQ ID NO: 1) |
| (2) TAT1-4,5 TO 8,9-TOD | R3-Tic-Oic-R4-Tic-D-Oic-R5 (SEQ ID NO: 15) |
| (3) TAT1-4,5 TO | R3-Tic-Oic-R2 (SEQ ID NO: 16) |
| (4) TAT1-8,9 TO | R1-Tic-Oic-R5 (SEQ ID NO: 17) |
| (5) TAT1-8,9 TOD | R1-Tic-D-Oic-R5 (SEQ ID NO: 13) |
| (6) 3K-TO-3K | R6-TicOic-R6 (SEQ ID NO: 18) |
| (7) 3A-TO-3A | R7-TicOic-R7 (SEQ ID NO: 19) |
| (8) TAT1-Den | R6<br>R6-DABA<<br>R6 (SEQ ID NO: 6) |
| (9) TAT1 A8-10 | GRKKRRQ-R7-PS (SEQ ID NO: 7) |

R1 GRKKRRQ (SEQ ID NO: 8)
R2 RQRRRPS (SEQ ID NO: 9)
R3 GRK
R4 RQ
R5 RPS
R6 KKK
R7 AAA

TAT Peptides Activate the ChT-L Peptidase of the Human Proteasome in vitro and in Cellulo. As summarized in Table 3 and demonstrated in FIG. 11, TAT1 and peptides with turn inducers in either of the predicted turn-promoting positions activated the latent human core 20S proteasome. Stabilization of a turn in the position 8,9 seemed superior to the position 4,5 for activating potential. Importantly, simultaneous stabilization of both turns in (2) was detrimental to the activation capability. On the other hand, replacement of TAT1 basic fragments with a KKK sequence yielded (6) with activation preserved, albeit with disappointingly high $AC_{50}$. The negative control (7), with an AAA stretch replacing KKK, displayed no ability to activate the core proteasome. With the goal of improving affinity of (6) to the proteasome, it was with an additional KKK sequence and joined the three triple-Lys fragments via diaminobenzoic acid in (8) (Tat1-Den). Consequently, (8) displayed one of the highest activation folds for the 20S core and one of the lowest $AC_{50}$ (Table 3, FIG. 11).

TABLE 3

Peptides based on HIV-1 Tat protein fragment, Tat1, are potent activators of the 20S core proteasome in vitro (purified 20S proteasome in Tris/HCl buffer pH 8 with model substrate for the ChT-L activity). $AC_{50}$: concentration at which the compound reaches 50% of the maximal activation effect. Titration curves for the compounds are presented in FIG. 11.

| | Compound | $AC_{50}$ [nM] ± SE | Max activation fold ± SE |
|---|---|---|---|
| (1) | Tat1 | 710 ± 12 | 6.2 ± 0.20 |
| (2) | Tat1-4, 5 TO 8, 9-TOD | 1528 ± 208 | 1.5 ± 0.26 |
| (3) | Tat1-4, 5 TO | 643 ± 74 | 3.3 ± 0.23 |
| (4) | Tat1-8, 9 TO | 499 ± 62 | 5.2 ± 0.76 |
| (5) | Tat1-8, 9 TOD | 220 ± 89 | 7.9 ± 0.74 |
| (6) | 3K-TO-3K | 1199 ± 118 | 8.0 ± 0.12 |
| (7) | 3A-TO-3A | 1744 ± 414 | 1.2 ± 0.04 |
| (8) | Tat1-Den | 374 ± 13 | 9.8 ± 0.18 |
| (9) | TAT1 A8-10 | ND | 0.9 ± 0.12 |

Interestingly, two types of titration profiles with TAT peptides were observed (FIG. 11): The most common was a profile with a pronounced maximum of activation followed by a systematic drop of the effect, resulting in a bell-shaped curve. It is thought that this type of response is characteristic for compounds that have additional binding sites with a weaker apparent binding constant and negative cooperativity with the primary binding site. The role of the secondary binding site can be played by the homologous sites present on the opposite side of 20S complex. The primary binding of these TAT ligands may stimulate secondary binding sites characterized by distinct thermodynamic properties. The secondary sites may bind accumulating products of substrate digest instead of TAT ligands and trigger partial inhibition of the activation effect. Finally, binding of the ligands may affect performance of a single active center as well as the cooperativity between them. It is established that the active centers responsible for breaking peptide bonds at hydrophobic residues (ChT-L activity) are linked by positive cooperativity [31, 32]. The second type of response followed a typical sigmoidal shape reaching the saturation level. This titration profile was found in three cases: a poor activator (2) containing two turn inducers, a good activator (6) with one TO turn and two simplified KKK "whiskers", and a similar but DABA-based dendritic peptide with three KKK "whiskers" (8). The most straightforward explanation would imply that, for these compounds, any meaningful secondary site binding and accompanied activity drop required impractical or unachievably high ligand concentrations. Alternatively, it is possible that these compounds simply do not have secondary binding sites that induce proteasome inhibition. Instead, they may have additional binding sites that prompt the positive cooperativity. The current biochemical data preclude conclusion if this titration shape reflects binding to the analogous site on the other side of the proteasome molecule or additional unidentified binding pockets.

Figure 11:
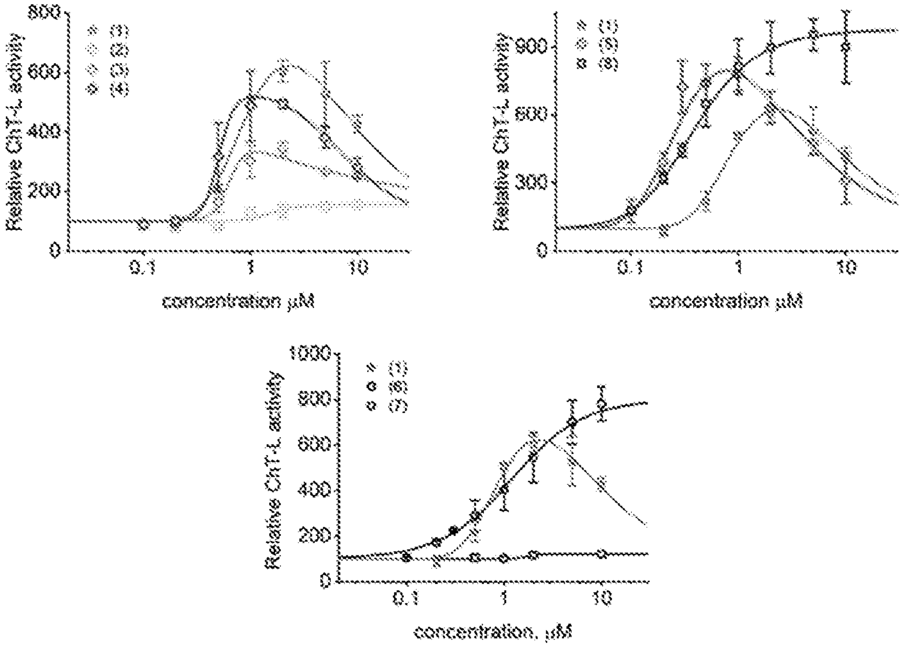
FIG. 11 shows that the chymotrypsin-like activity of latent human 20S proteasome was activated by TAT1 (1) and its derivatives in a dose dependent manner. (4)-(5) with turn inducers at the 8,9 position outperformed (3) with a TO turn inducer at the position 4,5. Interestingly, (2) that contains TO and TOD turn inducers at the positions 4,5 and 8,9, respectively, was a very poor activator. (8) exhibited the highest fold of activation potential and a low $AC_{50}$. No ability to activate was detected for (7) where the lysines were substituted with alanines and for (9) with alanines replacing turn-promoting residues. Means±SD, n=3-8. The control activity presented as 100% corresponded to 5 nanomoles of the fluorescent AMC product released per minute by 1 mg of 20S proteasome from the Suc-LLVY-AMC substrate (succinyl-LeuLeuValTyr-7-amino-4-methylcoumarin).
Figure 12:
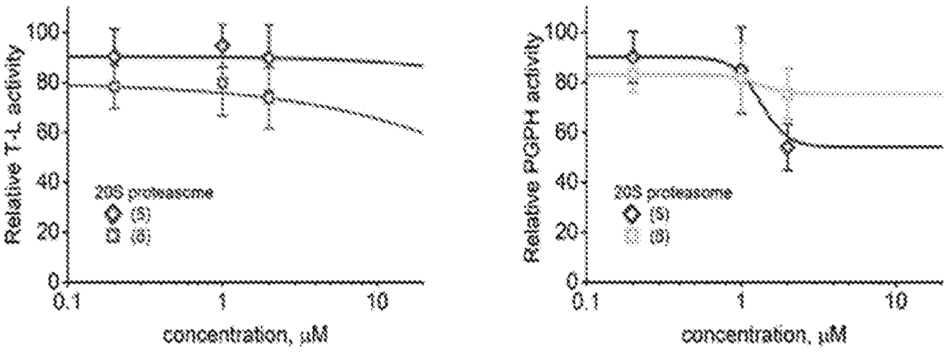
FIG. 12 shows that as demonstrated for (5) and (8), the TAT1 derivatives did not seem to significantly affect the post basic (trypsin-like; T-L) and post acidic (post glutamyl peptide hydrolyzing; PGPH) peptidase activities of the core proteasome. Means±SD, n=3-4. The control relative activities (100%) corresponded to 9.2±1.4; n=3 (T-L) and 3.1±0.3; n=4 (PGPH) nanomoles of the AMC (7-amino-4-methylcoumarin) product per mg of latent 20S per minute, respectively.

Among the three proteasomal cleavage specificities, the "workhorse" ChT-L peptidase was significantly affected, as demonstrated for selected compounds (FIGS. 10, 11). Compounds (5) and (8) actually showed weak inhibitory effects on T-L (trypsin-like) and postglutamyl peptide hydrolyzing (PGPH) activities (FIG. 12).

Taken together, a structural constraint induced by a single turn placed close to the C-terminus and selected basic residues were important to achieve the strongest activation at the lowest peptide concentration.

Figure 13:
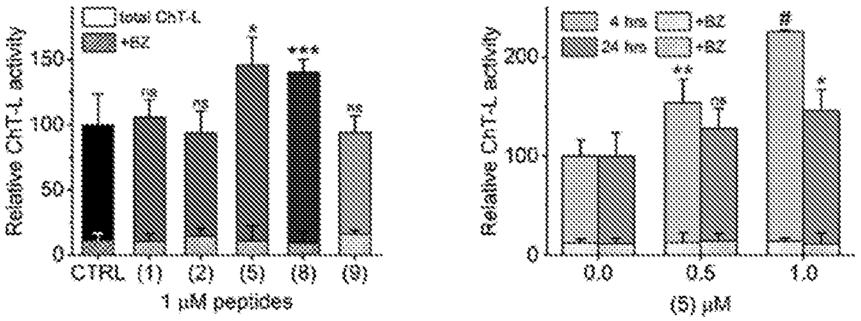
FIG. 13 shows that treatment of human neuroblastoma SK-N-SH (ATCC HTB-11) cell line with selected TAT1 derivatives resulted in significant augmentation of the proteasome activity. Left: After 24 h treatment with vehicle (DMSO) or TAT compound, cell lysates were prepared and ChT-L activity measured. Relative activity per mg of protein in lysates is presented. Treatment of the same cell lysates with 1 μM Bortezomib lead to almost complete abrogation of ChT-L activity independent of the type of TAT peptide used. Proliferation and viability of cells were not affected by the treatments: live cell counts remained at the level of 95%-107% of control, with the sole exception of a lower count for (9) (86%, non-significant difference). The content of dead cells varied between 9% and 12% for the samples tested (no significant differences). Right: SK-N-SH cells were treated for four or 24 h with 0.5 or 1.0 μM of (5) and processed as above. An increase of proteasome activity was dose dependent and was affected by the treatment interval. Exposure of the cell lysates to 1 μM BZ almost completely eliminated ChT-L activity and its dependence on treatment time and the applied (5) dose. The control 100% activity corresponded to 1.1 (24 h treatments) or 0.31 (4 h treatments) nanomol of the AMC product released by mg of the lysate per minute. *, p≤0.05; , p<0.01; *, p<0.001; #, p<0.00001 (t test; n=3-4); ns—not significant difference.

The strong in vitro performance of TAT peptides led to the testing of selected activators on proteasome activity in cultured cells. Human neuroblastoma SK-N-SH (ATCC/American Type Culture Collection HTB-11) line was chosen as a representative for neural cells as these may become future targets of proteasome agonists in treatment of neurodegenerative diseases with compromised proteasome performance. None of the tested compounds at 1 μM significantly affected proliferation and viability of the cells after 24 h of treatment (see caption of FIG. 13). However, the proteasome activity in lysates prepared from the treated cells was significantly higher than activity in control lysates for (5) and (8). The lack of significant activation for (1) (FIG. 13, left) could be explained by significantly compromised cytosolic stability of the TAT1 peptide, as compared with the derivatives that may be protected from degradation by the synthetic turn inducers. This conclusion is further supported by the observation that dose dependent proteasome activation with (5) in SK-N-SH cells was substantially stronger after 4 h exposure than after 24 h (FIG. 13, right). Importantly, both (2) and (9) followed in cellulo their poor in vitro performance. The activation by (5) and (8) detectable in the lysate could be explained by two non-excluding phenomena: the direct enhancement of the peptidolytic activity by strongly binding compounds or enrichment of the content of active proteasomes in treated cells. Initial experiments point at the strong binding of these otherwise reversible compounds. Since 1 μM bortezomib treatment of the lysates from both control and TAT-exposed cells abolished ChT-L activity to a comparable extent (>85% (FIG. 5)), the possibility that the observed increase of peptidase activity was due to upregulation of other proteases was excluded.

The α1/α2 Inter-Subunit Pocket on the a Face of Core Proteasome is the Primary Binding Site of TAT Peptides. The Binding Changes Conformational Equilibrium of the Proteasome's Gate. To gain mechanistic insight and to aid further modifications of the compounds, molecular docking of (5) to the human core proteasome was performed using Rhodium® software suite (Southwest Research Institute; SwRI; San Antonio). In its docking approach, different locations on the surface were seeded with $10^4$ to $10^5$ copies of a ligand conformer, generating trial candidate binding configurations. The inhibitor's seeded configurations were allowed to move independently over the surface, optimizing the coordinates of the binding location along a path to a local energy minimum on the surface. Certain ligand molecules starting at different locations converged to several common locations. The docking was performed in two steps. First, a square-well interatomic potential for docking, similar to the approach published by Vakser [33,34] was used for the primary docking. Next, the identified docking pose candidates were screened with a second tier docking for pose refinement, typical for the traditional docking codes.

Figure 14:
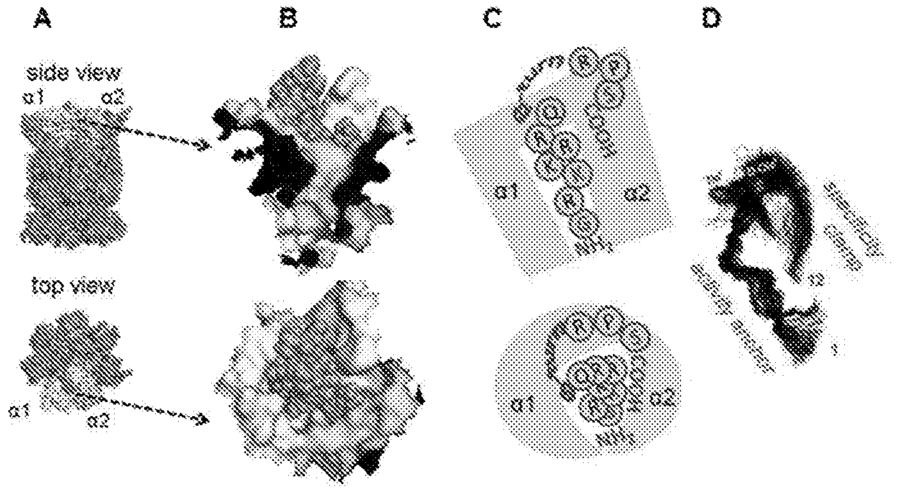
FIGS. 14A-D show that molecular docking (Rhodium®) of (5) to the human 20S (pdb: 5LE5; [35]), pointed to the α1/α2 pocket as the preferred binding site.

FIG. 14A demonstrates the proposed docking with (5) positioned in the pocket between the core subunits α1 and α2. The N-terminal part of (5) was proposed to penetrate deep into the pocket, with multiple potential hydrogen bonds engaging the N-terminal (1-7) residues of (5) and stabilizing the binding. The predicted turn extended above the α face, whereas the C-terminal Ser showed propensity to interact with exposed residues of al (FIG. 14B). Based on this result, it was tested whether the N-terminal part of (5) may serve as an "activation anchor", whereas the turn positions the C-terminal part to interact with the α face as a "specificity clamp" (FIG. 14C). The improved performance of (8) as compared with (6) could be then explained by beneficial actions of an additional "specificity clamp", possibly strengthening the ligand binding.

Figure 15:
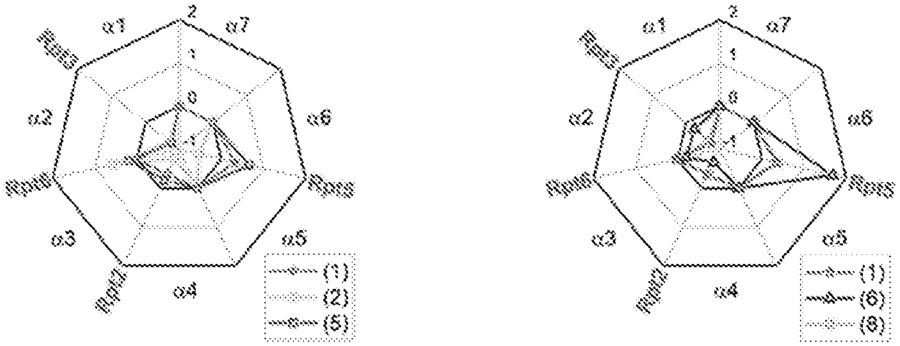
FIG. 15 shows TAT1 derivatives competed with selected C-terminal tails of Rpt (Regulatory Particle ATPases) subunits for binding to specific α face pockets. The scores presented in radar plots were calculated as ((relative activation by the [x] and Rpt tail)−(theoretical sum of activation by [x] and Rpt tail))/(theoretical sum of activation by [x] and Rpt tail), where [x] represent any TAT peptide. Score=1 indicates a pure additive effect of Rpt and TAT peptides, score <1 suggests competition, score >1 hints at synergy. (5) competed fairly specifically with Rpt3 tail, expected to dock in the α1/α2 pocket, as evident from the strongly negative score. (1) and (8) added a weakly negative score for the Rpt2 tail to the presumed major competitor Rpt3. In turn, Rpt2 tail was a major competitor for (6). The poor activator (2) was the least specific ligand of the α face, competing with Rpt2, Rpt3, and Rpt5 tails. The positive scores for combinations of selected compounds with Rpt5 or Rpt6 tails indicated a presumed synergy in activation of the core. Average scores derived from three to six experiments are presented. The competition effects were statistically significant (at least p<0.05) for Rpt3 peptide and (1) and (8), as well as for Rpt2 peptide and (6).

As mentioned herein, the binding pockets on the α face accept "anchors" from natural protein ligands of the 20S core [25,36,37]. Certain anchoring peptides are known to interact with the α face in trans, most notably C-terminal "tails" of Rpt ATPase subunits of the 19S complex bearing the "HbYX" (hydrophobic-Y-any amino acid) C-terminal motif [38]. The 10-residue Rpt-derived C-terminal "tail" peptides ("Rpt peptides") can be used as competitors with the Rpt subunits or with small allosteric ligands [19,38,39]. Importantly, the Rpt peptides interject between the subunits with their C-termini, whereas TAT peptides, according to the modeling, use their N-termini for this purpose. To test the specificity of interactions between TAT compounds and the α face, competition experiments were performed. The 20S core was challenged with selected TAT compounds after treatment with Rpt peptides. Peptides of Rpt2 (QEGTPEGLYL; SEQ ID NO: 10), Rpt3 (KDEQEHEFYK; SEQ ID NO: 11), Rpt5 (KKKANLQYYA; SEQ ID NO: 12) and Rpt6 (KNMSIKKLWK; SEQ ID NO: 13) subunits were selected, docking in α3/α4, α1/α2, α5/α6 and α2/α3 pockets, respectively. Tails of Rpt2, 3, and 5 display the canonical HbYX motif, whereas the LeuTrpLys C-terminus of Rpt6 may be considered "pseudo-HbYX", with a bulky Trp replacing Tyr. Results of the competition experiments are presented as radar plots in FIG. 15. Relative ChT-L proteasome activity at or near 1 indicated that activations by a Tat compound and by the Rpt tail (if detectable) were fully preserved and therefore no competition between the peptides was considered. A score below 1 indicated active competition, whereas a score above 1 suggested enhanced, possibly synergistic, activation (positive cooperativity) in the presence of a TAT and an Rpt tail. The indications of the molecular docking (FIG. 14) were fully confirmed for (5): the Rpt3 peptide (α1/α2 pocket) was its sole competitor. This pocket also emerged as the major binding site for (1) and (8). However, these compounds likely weakly competed with the Rpt2 tail for binding to the α3/α4 pocket as well. The α3/α4 pocket seemed to be favored by (6). The poor activator (2) was, not surprisingly, least specific in its binding preferences, adding the spacious α5/α6 (Rpt5) pocket to the putative sites of competition. Interestingly, (1), (5), (6), and (8) displayed enhanced activation in the presence of one of Rpt tails, namely Rpt5 or Rpt6. The presumed synergy was pronounced for the Rpt6-(2) pair, as well as Rpt5-(1), (5), and (6) pairs (FIG. 15). These complex patterns point at the importance of allosteric effects between the α face ligands, the gate and the catalytic chamber.

Figure 16:
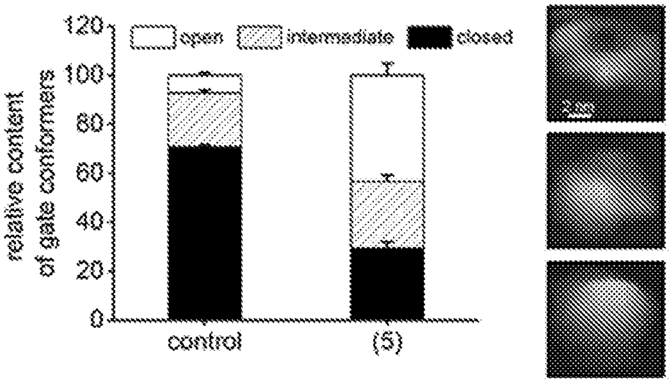
FIG. 16 shows AFM (Atomic Force Microscopy) imaging detected a larger abundance of open-gate conformers after treatment of 20S proteasomes with (5). In control samples treated with vehicle (DMSO) the closed-gate conformation prevailed (71%), with 7% of open-gate particles and 22% assuming intermediate conformation. The partition for latent, untreated proteasomes was undistinguishable from DMSO-treated controls ([20, 39]). In the presence of 1 μM of (5) 43% of core proteasomes assumed the open-gate conformation at any given time of AFM probing. 29% of the molecules remained in closed conformation, and 27% proteasomes were classified as intermediates. In total, 180 control and 337 (5)-treated particles/cases from n=4 independent experiments were analyzed. Based on the results of the chi squared test, it was concluded that the partition of 20S proteasome gate conformers is associated with the presence of (5) and significantly different from the partition found in the control (DMSO-treated) proteasome.

The putative binding site corresponds to one of the natural "anchoring spots" on the a face of the core proteasome. The inter-subunit pockets are used to attach regulatory proteins: PA28/ REG (all pockets), PA200 (proteasome activator of 200 kDa; α5/α6 pocket), as well as the Rpt subunits of the 19S particle (all pockets except α6/α7 and α7/α1) [26, 36, 40]. Peptide-activators of the core that utilize the structure of docking fragments of these natural activators were found to bind into the α5/α6 pocket, while a small molecule activator TCH-165 reportedly preferred the α1/α2 site [19,20,41]. Binding of these ligands resulted in opening or at least destabilizing the gate in the center of the α face, as revealed by crystal structures, cryoEM (cryo-electron microscopy) and atomic force microscopy (AFM) imaging [19,20,25,40-43]. Gate opening is prerequisite for the uptake of substrates and release of products from the concealed catalytic chamber of the core proteasome (FIG. 9A). Conformational diversity of the latent core proteasome allows for periodic gate opening and potential substrate uptake [44]. Moreover, the gate is allosterically connected by a positive feedback loop(s) with active sites: a catalytic act in any of the sites sends a signal to open the gate and upkeep enzymatic action [45]. As previously established, AFM collects images of single, native proteasome particles at nanometer resolution. The particles exhibit a well discernible gate area, assuming dynamic "open", closed" or "intermediate" positions, corresponding to the gate conformations detected by cryoEM [20,25,39,46]. These observations led to the search for structural consequences of (5) binding to the proteasome with AFM. The latent core is known to preferentially remain in the closed-gate conformation, accounting for about three-quarters of particles detected by cryoEM or AFM, with less than 10% assuming the fully open-gate position [20,25,39]. In contrast, treatment with 1 μM of (5) resulted in a dramatic shift in partition of conformations toward more abundant, over 40%, open-gate proteasomes, and less prominent, below 30%, closed-gate particles (FIG. 16). Also, slightly (albeit significantly) more particles assumed the intermediate gate position in (5)-treated preparation than in vehicle-treated control (FIG. 16). In control and compound-treated preparations alike, the single particles could freely change their conformations with time, as detected in consecutive scans. The conformational landscape with such a prominent representation of open-gate particles is uncommon among proteasome partitions detected in the presence of other small proteasome ligands. Pro-Arg-rich and HbYX-accommodating peptide activator PR2 prompted a strong increase in intermediate (nearly 40%) and a moderate increase (less than 20%) in open-gate forms [20]. In contrast, allosteric small-molecule or peptide inhibitors docking in the α face pockets suppressed the open-gate conformers [20,39]. The apparent strong stabilization of the open-gate conformation by (5) would be expected to promote catalysis by easing the rate-limiting obstacle of a closed gate. However, the fact that ChT-L and not the other two proteasomal peptidases are activated by TAT peptides (FIGS. 11, 12) also points at the possible role of allosteric signaling. Indeed, proteins, peptides or small molecules targeting the α face may in vitro affect one or more peptidases [28]. Explanation of the diverse effects may involve a direct signaling between the α face pockets and catalytic chamber, between the gate and catalytic chamber, or any of the former plus inter-catalytic sites allosteric loops [47,48]. TAT peptides can be used for studying proteasome allostery.

In the light of significant proteasome-enhancing effects of TAT peptides observed both in cellulo (FIGS. 13 and [15]) and in vivo [15], there is an important question of how they influence proteolytic activity in the most widespread form of the proteasome, the 26S holoenzyme. The most-explored TAT compounds are proposed to dock in the α1/α2 pocket, which, alongside the α5/α6 pocket, is permanently occupied in the conformational forms of the 26S assembly [46]. Therefore, activation of the core already decorated with two 19S modules seems excluded. Still, in the in vitro experiments, a significant, up to three-fold activation of the 26S proteasome was observed. Although it was lower than for the 20S proteasome, it was concentration-dependent ([15] and Osmulski, Gaczynska). The two most plausible explanations of the phenomenon are: (i) the compounds affect the free core present in small quantities in purified 26S preparations and present to a physiologically determined extent in living cells; (ii) the previous case extended with activation of the half-26S assemblies with one α face blocked by 19S cap and the other left free. Since single-cap proteasomes are fully capable of recognizing and processing polyubiquitinated substrates, the latter opens an opportunity of TAT peptides mediated activation of ubiquitin-dependent proteolysis. Importantly, as revealed by cryoelectron tomography in live neurons, two-thirds of 19S-decorated proteasomes are in the single-capped form [49], whereas in many other cells, full 26S assemblies or hybrids with both a faces blocked were reported as most abundant [50,51]. Such opportunity to efficiently activate proteasomes in neural cells would be relevant to anti-Alzheimer's disease actions of the peptides. As reported by Chocron et al. [15], the proteins with turnover increased by treatment with (5) or (8) included proteasome substrates possibly processed in ubiquitin-independent (APP; [52]) but also in the ubiquitin-dependent manner (β secretase; [53]).

Materials and Methods. Synthesis of Selected Peptides. Synthesis and properties (1) have been described[22], (2)-(5) and (9) have been described[24]. Synthesis and purification of (6) and (7) followed the procedures described in [24]. The peptides have been purified to at least 99% of purity.

Synthesis of TAT1-Den Peptide (8). Synthesis of (8) was performed on 0.25 mmol scale, according to Fmoc/tBu methodology, in a Liberty Blue™ automated microwave synthesizer (CEM Corporation). The TentaGel PHB resin was used as a solid support with an initial capacity of 0.23 mmol/g.

The following Fmoc-protected amino acid derivatives were used in the synthesis: Fmoc-Lys(Boc)-OH and Di-Fmoc-3,5-diaminobenzoic acid.

The first amino acid, Fmoc-Lys(Boc)-OH, was attached to the solid support using 1-methylimidazole (MeIm) and 1-(2-mesitylenesulfonyl)-3-nitro-1H-1,2,4-triazole (MSNT). 5 eq. of Fmoc-Ser(t-Bu)-OH (relative to the resin capacity) was dissolved in dichloromethane (DCM) with addition of a few drops of tetrahydrofuran. Next, 3.37 eq. of MeIm and 5 eq. of MSNT were added, and the mixture stirred for 15 min. The mixture was then transferred to a round-bottom flask containing the resin swollen in DCM. The mixture was flushed with argon and left on a vertical shaker for 2 h, then the peptidyl resin was drained, washed and dried in a vacuum desiccator. The resin loading was determined as follows: a few milligrams of the dry peptidyl resin were transferred to a 2 mL test tube, 1 mL of 20% piperidine in dimethylformamide (DMF) was added, and the tube was shaken for 30 min. Then, the mixture was transferred to a 25 mL volumetric flask and filled with methanol. The solution was transferred to a quartz cuvette and the loading of the peptidyl resin was calculated from measurement of the absorbance at λ=301 nm.

The Fmoc-Lys(Boc)-resin was transferred into a reaction vessel and soaked prior the synthesis cycle in DMF for 30 min. In the next step, the Fmoc group was removed (deprotection cycle) using 30% solution of piperidine in DMF. The mixture was irradiated for 15 s with a 167 W microwave power (temperature 75° C.), then with a power of 31 W for 50 s (temperature in the range 89-90° C.). The solid support was then drained and washed four times with DMF, and the deprotection cycle was repeated. Next N-terminally protected amino acid was attached, using as a coupling solution a mixture of 0.5 M N,N'-diisopropylcarbodiimide (DIC) and 1 M Oxyma pure (racemization suppressor) in DMF. The coupling reaction step was carried out with a four-fold excess of an amino acid derivative, calculated based on the initial capacity of the solid support. The efficiency of this step was enhanced with microwave radiation of 162 W for 15 s (temperature 75° C.), then 33 W for 110 s (temperature in the range of 89-90° C.). The peptidyl resin was then drained and the coupling cycle was repeated. Next, the 30% piperidine solution in DMF was added to de-protect the N-terminal amino group. This step was carried out in the same conditions as described herein. Double coupling cycles with the use of DIC/Oxyma reagents were performed till the attachment of the third Fmoc-Lys(Boc)-OH residue (fifth residue in the sequence). Coupling of the fourth residue in the sequence (Di-Fmoc-3,5-diaminobenzoic acid) was carried out with a three-fold excess of the amino acid, calculated based on the initial capacity of the solid support. The efficiency of this step was enhanced by applying microwave irradiation (85 W for 60 s, temperature 40° C., then 25 W for 540 s, temperature in the range of 63-65° C.). The peptidyl resin was then drained and the coupling cycle was repeated. The residue was deprotected under the same conditions as described herein, with triple repetition of the cycle. Starting from the third residue in the sequence, the coupling reagents were switched to 1-Cyano-2-ethoxy-2-oxoethylidenaminooxy) dimethylamino-morpholino-carbenium hexafluoro phosphate COMU. The N-protected amino acid derivatives were coupled with the use of a three-fold excess of an amino acid, calculated based on the initial capacity of the solid support, 2.9-fold of COMU and 5.8-fold of diisopropylethylamine. The coupling efficiency was enhanced by applying microwave irradiation of 120 W for 60 s (temperature 60° C.), then 25 W for 30 s (temperature in the range of 78-80° C.). The peptidyl resin was then drained and the coupling cycle was repeated. The deprotection reagents and protocols were not changed. After completion of the synthesis, the peptidyl resin was washed four times with DMF, then three times with methanol and left overnight to dry in a vacuum desiccator.

Peptide Cleavage from the Solid Support. The peptide was cleaved from the solid support, along with the removal of protecting groups from amino acid side chains, using the mixture of trifluoroacetic acid (TFA), triisopropylsilane and water (92:4:4, v/v/v). The reaction was carried out for two hours on a laboratory shaker. The resin was then drained under the reduced pressure on a filter funnel and the filtrate was concentrated to a volume of about 2 mL with a vacuum evaporator. The remaining filtrate was treated with diethyl ether (cooled to about 4° C.). A white precipitate was obtained and centrifuged in a centrifuge tube for 15 min (4500×g). The supernatant was decanted and the pellet was treated with another portion of diethyl ether. The precipitate was washed this way three times, and then dried in a vacuum desiccator. The obtained crude product was dissolved in water and freeze-dried.

Purification. The compound was purified using a reversed-phase HPLC (RP-HPLC). The crude product was dissolved in water and injected onto a Jupiter® Proteo C12 semipreparative column (21.2 mm×250 mm, 90 Å, 4 μm; Phenomenex). The chromatographic separation was carried out using a linear gradient of 1-100% B over 75 min, and the eluents: A: 0.1% TFA in $H_2O$ and B: 0.1% TFA, 10% methanol in $H_2O$. The eluent flow rate was 15 mL/min, UV detection at λ=223 nm. After the collection of the main fraction, solvents were evaporated using a vacuum evaporator. Next, the fraction was dissolved in water and injected onto the same semipreparative column. The second purification was carried out in a linear gradient of 1-40% B over 75 min with the eluents: A: 0.1% TFA in $H_2O$ and B: 0.1% TFA in 5% acetonitrile (ACN) in $H_2O$. The eluent flow rate was 15 mL/min, UV detection at λ=223 nm.

Characterization of the Product with HPLC and Mass Spectrometry. The product was subjected to chromatographic analysis using RP-HPLC. Conditions: chromatographic column: Kinetex 2.1 mm×100 mm, 100 Å, 2.6 μm (Phenomenex); eluents: A: 0.1% TFA in H2O, B: 0.1% TFA, 80% ACN/H20; flow rate 0.5 mL/min; UV detection at A=223 nm; gradient 5-45% B over 7 min, temperature of an oven 40° C., Rt=4.42 min. The calculated molecular weight of the compound was confirmed using a LC-MS IT-TOF (Shimadzu) mass spectrometer. Peptide was injected directly into the ion source. Theoretical average molecular weight of the compound: 1305.2 Da, obtained m/z: 1304.81 [M]+.

Determination of Proteasome Activity. Human housekeeping core (20S) proteasome purified from erythrocytes was purchased from Boston Biochem, Inc. (Cambridge, Mass.) or from Enzo Life Sciences, Inc. (Farmingdale, N.Y.). Multiple batches of the proteasomes were used and performed reproducibly. The stock proteasome was diluted to 0.2 mg/mL working solution in "dilution buffer" (50 mM Tris/HCl, pH 8, 20% glycerol). The following model peptide substrates, releasing fluorescent 7-amino-4-methylcoumarin (AMC) reporter group after cleavage, were used: succinyl-LeuLeuValTyr-AMC (SEQ ID NO: 14) (for the ChT-L peptidase; SucLLVY-AMC; Bachem Bioscience Inc., Philadelphia, Pa.), butoxycarbonyl-LeuArgArg-AMC (T-L; Bachem Bioscience Inc., Philadelphia, Pa.) and carbobenzoxy-LeuLeuGlu-AMC (PGPH; Enzo Life Sciences Inc., Farmingdale, N.Y.). The substrates were used at concentration of 50 μM (ChT-L) or 100 μM (T-L, PGPH). Free AMC (Sigma-Aldrich, St. Louis, Mo.) was used as the standard. The C-terminal peptides derived from Rpt2, Rpt3, Rpt5 and Rpt6 were synthesized (standard solid-phase peptide chemistry) and purified to at least 98% purity by GenScript (Piscataway, N.J.). The TAT peptides, Rpt peptides (except Rpt6) and the peptide substrates were dissolved in anhydrous dimethylsulfoxide (DMSO; Sigma-Aldrich, St. Louis, Mo.) and such stock solutions were stored at −20° C. The total concentration of DMSO in final reaction mixtures never exceeded 3% (vol/vol). The Trp (tryptophan)-containing Rpt6 peptide was dissolved in ultrapure water and stored at −20° C., protected from light. The reaction was carried out in 96-well plates, in 100 μL of reaction mixture that consisted of 45 mM Tris/HCl, pH 8, 100 mM KCl, 1 mM EDTA (reaction buffer) and a fluorogenic peptide substrate, to which 200 ng (nearly 0.3 nmol) of proteasome were added. The addition of KCl/EDTA (ethylenediaminetetraacetic acid) to reaction buffer assured latency of the core proteasome. The proteasome was preincubated with a substrate for 10 min at room temperature, then 1 μL of DMSO or a desired concentration of a TAT peptide in 1 μL of DMSO were added. After mixing, the plate was transferred to a Fluoroskan Ascent plate reader (Thermo Fisher Scientific Inc., Waltham, Mass.) for 1 h (37° C.), with fluorescence readouts once per minute [54]. To test the competition with Rpt derived peptides, the Rpt peptide (1 μM) was added before the TAT peptide to the reaction mixture. The reaction rates were calculated from a linear segment of kinetic curves constructed from measurements in 1-min intervals. Reaction rates were calculated using a linear fit performed with the Slope Analyser and Enzyme Kinetics applications launched within Origin Pro 2019 (OriginLab Corporation, Northampton, Mass.). Specific ChT-L activity of the latent control 20S proteasome ranged from 3.4 to 6.0 nanomoles of AMC product released by 1 mg of 20S per minute (4.2±0.8; n=26). The data are presented as mean±SD from at least three independent experiments.

Cell Culture. Human SK-N-SH neuroblastoma cell line (ATCC® HTB-11™ American Type Culture Collection; Manassas, Va.) were cultured according to ATCC specifications (EMEM, 10% heat-inactivated FBS) The cells at passage 2-4 were treated with 1 μM TAT peptides or the DMSO vehicle diluted with the medium 1:1000, for 24 h. The content of live cells was determined by the Trypan Blue-exclusion assay. The cells were harvested, washed twice in PBS, resuspended in dilution buffer (as described herein) and stored in −80° C. To prepare lysates, the thawed preparations were vortexed with glass beads and centrifuged for 5 min 5,000×g (4° C.). The supernatant was centrifuged for 20 min 14,000×g (4° C.). The resulting supernatant—"crude lysate" was diluted to 1 mg/mL of total protein with dilution buffer. 1 μg of lysate per assay (reaction buffer: 50 mM Tris/HCl pH 8, 0.1 mM $MgCl_2$, 0.2 mM ATP, 0.1 mM dithiothreitol, 50 μM Suc-LLVY-AMC (SEQ ID NO: 14)) was used for determination of ChT-L activity in a 96-well format, as above. Activities in lysates were also tested in the presence of a high concentration (1 μM) of a strong competitive proteasome inhibitor Bortezomib. The resulting negligible degradation of the model substrate in the presence of bortezomib indicated that proteasome is the sole source of activity observed in the lysates.

Molecular Docking. Relative binding locations of (5) were determined on the surface of human core proteasome represented by crystal structure 5LE5 [35]. The 3D structures of (5) were used [24]. Docking poses were determined with Rhodium® 3.9 in four separate docking trials, as described in Results. For each trial, poses were generated on a grid covering the surface of the protein model, with 72 trial states per grid point, with resolution of 1.7 Å. Forty poses with the maximum cavity-filling scores were prepared and analyzed with PyMol v.1.5.0.5 (Schrodinger LLC, New York, N.Y. [55-57]). The top-ranking pose with ligand-proteasome contacts along both activation anchor and specificity clamp is presented.

Atomic Force Microscopy (AFM) Imaging. Single molecules of 20S proteasomes were imaged in tapping (oscillating) mode in liquid, with a scanner E of the Multimode Nanoscope IIIa (Bruker Inc., Santa Barbara, Calif.) [45]. The proteasomes were electrostatically attached to a muscovite mica substrate, covered with imaging buffer (5 mM Tris/HCl, pH 7) and scanned using cantilevers with the spring constant of 0.35 N/m from the SNL (Sharp Nitride Lever) probes (Bruker Inc., Santa Barbara, Calif.) tuned to 9-10 kHz. The amplitude set-point in the range of 1.5-2.0V, drive voltage of 300-500 mV and 3.05 Hz scanning rate were used. Scans of 1 $μm^2$ fields (512×512 pixels) were collected in height-mode. The images of fields typically contained several dozens of top-view ("standing") 20S proteasome particles. The gate status was deduced from a profile of raw height values of pixels measured by a probe scanning across the single proteasome particles [20,39]. In short, under the employed scanning conditions the proteasome a face with the central gate area was completely rendered by a six-pixel (11-12 nm) scan-line fragment. Numerical values of the height of particles of raw (after standard flattening) images were collected with a practical vertical resolution reaching 1 Å. When this scan-line presented a local minimum (a central dip), the particle was classified as containing the open gate. The particle was classified as an intermediate conformer when a plot of height values presented a concave function without a local minimum. When the function was convex, the particle was classified as containing the closed gate. The "events" of gate opening/closing were analysed for scans of distinct particles as well as multiple scans of the same particles.

Statistical Analysis. Experiments were performed at least in three independent replicates. The results are presented as a mean±SD. A two-tailed t-test was applied to compare the means. The comparisons were allowing for unequal variances with a Welch correction. Abundance of proteasome conformers was compared with the chi squared test and two-sample proportion test. A significance level was set at 0.05. Statistical analysis was performed using statistical procedures offered by OriginPro 2019 (OriginLabs, Northampton, Mass.). Reaction rates were calculated from a smoothed linear segment of kinetic traces using OriginPro 2019. Response curves (activity vs. compound concentration) were fitted with a nonlinear fitting application of OriginPro 2019. The $AC_{50}$ and maximum activation fold was calculated based on the equations implemented to fit the response curves.

REFERENCES

1. Jankowska, E.; Stoj, J.; Karpowicz, P.; Osmulski, P. A.; Gaczynska, M. The proteasome in health and disease. *Curr Pharm Des.* 2013, 19, 1010-1028.
2. Adams, J. The proteasome: A suitable antineoplastic target. *Nat. Rev. Cancer.* 2004, 4, 349-360.
3. Besse, A.; Besse, L.; Kraus, M.; Mendez-Lopez, M.; Bader, J.; Xin, B.-T. Proteasome Inhibition in Multiple Myeloma: Head-to-Head Comparison of Currently Available Proteasome Inhibitors. *Cell Chem Biol.* 2019, 26, 340-351.
4. Rodriguez, K. A.; Gaczynska, M.; Osmulski, P. A. Molecular mechanisms of proteasome plasticity in aging. *Mech Ageing Dev.* 2010, 131, 144-155.
5. Chondrogianni, N., Gonos, E. S. Proteasome dysfunction in mammalian aging: Steps and factors involved. *Exp. Gerontol.* 2005, 40, 931-938.
6. Keller, J. N.; Hanni, K. B.; Markesbery, W. R. Impaired proteasome function in Alzheimer's disease. *J. Neurochem.* 2000, 75, 436-439.
7. McNaught, K. S.; Belizaire, R.; Jenner, P.; Olanow, C. W.; Isacson, O. Selective loss of 20S proteasome α-subunits in the substantia nigra pars compacta in Parkinson's disease. *Neurosci Lett.* 2002, 326, 155-158.
8. Rubinsztein, D. C. The roles of intracellular protein-degradation pathways in neurodegeneration. Nature. 2006, 443, 780-786.
9. Bedford, L.; Hay, D.; Devoy, A.; Paine, S.; Powe, D. G.; Seth, R. Depletion of 26S Proteasomes in Mouse Brain Neurons Causes Neurodegeneration and Lewy-Like Inclusions Resembling Human Pale Bodies. *J. Neurosci.* 2008, 28, 8189-8198.
10. Jones, C. L.; Tepe, J. J. Proteasome Activation to Combat Proteotoxicity. *Molecules.* 2019, 24, 2841.
11. Coleman, R. A.; Trader, D. J. Methods to Discover and Evaluate Proteasome Small Molecule Stimulators. *Molecules.* 2019, 24, 2341.
12. Njomen, E.; Tepe, J. J. Proteasome Activation as a New Therapeutic Approach To Target Proteotoxic Disorders. *J. Med. Chem.* 2019, 62, 6469-6481.
13. Chondrogianni, N.; Georgila, K.; Kourtis, N.; Tavernarakis, N.; Gonos, E. S. 20S proteasome activation promotes life span extension and resistance to proteotoxicity in *Caenorhabditis elegans. FASEB J.* 2015, 29, 611-622.
14. Munkácsy E, Chocron E S, Quintanilla L, Gendron C M, Pletcher S D, Pickering A M. Neuronal-specific proteasome augmentation via Prosβ5 overexpression extends lifespan and reduces age-related cognitive decline. *Aging Cell.* 2019, 18, 5.
15. Chocron, S. E.; Munkacsy, E.; Kim, Harper, S.; Jiang, N.; Van Skike, C. E.; DeRosa, N. Genetic and pharmacologic proteasome augmentation ameliorates Alzheimer's disease-like symptoms through increased turnover of β-amyloid machinery. *Nat. Commun.* 2020, under revision.
16. Huang, L.; Ho, P.; Chen, C.-H. Activation and inhibition of the proteasome by betulinic acid and its derivatives. *FEBS Lett.* 2007, 581, 4955-4959.
17. Coleman, R. A.; Muli, C. S.; Zhao, Y.; Bhardwaj, A.; Newhouse, T. R.; Trader, D. J. Analysis of chain length, substitution patterns, and unsaturation of AM-404 derivatives as 20S proteasome stimulators. *Bioorg Med. Chem Lett.* 2019, 29, 420-423.
18. Jones, C. L.; Njomen, E.; Sjögren, B.; Dexheimer, T. S.; Tepe, J. J. Small Molecule Enhancement of 20S Proteasome Activity Targets Intrinsically Disordered Proteins. *ACS Chem Biol.* 2017, 12, 2240-2247.
19. Njomen, E.; Osmulski, P. A.; Jones, C. L.; Gaczynska, M.; Tepe, J. J. Small Molecule Modulation of Proteasome Assembly. *Biochemistry.* 2018, 57, 4214-4224.
20. Giżyńska, M.; Witkowska, J.; Karpowicz, P.; Rostankowski, R.; Chocron, E. S.; Pickering, A. M. Proline- and Arginine-Rich Peptides as Flexible Allosteric Modulators of Human Proteasome Activity. *J. Med. Chem.* 2019, 62, 359-370.
21. Huang, X.; Seifert, U.; Salzmann, U.; Henklein, P.; Preissner, R.; Henke, W. The RTP Site Shared by the HIV-1 Tat Protein and the 11S Regulator Subunit α is Crucial for their Effects on Proteasome Function Including Antigen Processing. *J. Mol. Biol.* 2002, 323, 771-782.
22. Jankowska, E.; Gaczynska, M.; Osmulski, P.; Sikorska, E.; Rostankowski, R.; Madabhushi, S. Potential allosteric modulators of the proteasome activity. *Biopolymers.* 2010, 93, 481-495.
23. Witkowska, J.; Karpowicz, P.; Gaczynska, M.; Osmulski, P. A.; Jankowska, E. Dissecting a role of a charge and conformation of Tat2 peptide in allosteric regulation of 20S proteasome. *J. Pept Sci.* 2014, 20, 649-656.
24. Karpowicz, P.; Osmulski, P. A.; Witkowska, J.; Sikorska, E.; Giżyńska M.; Belczyk-Ciesielska, A. Interplay between Structure and Charge as a Key to Allosteric Modulation of Human 20S Proteasome by the Basic Fragment of HIV-1 Tat Protein. Itzhaki L, editor. *PLoS ONE.* 2015, 10, E0143038.
25. Chen, S.; Wu, J.; Lu, Y., Ma, Y. B.; Lee B H, Yu, Z. Structural basis for dynamic regulation of the human 26S proteasome. *Proc Natl Acad Sci USA.* 2016, 113, 12991-12996.

26. Jeang, K.-T.; Xiao, H.; Rich, E. A. Multifaceted Activities of the HIV-1 Transactivator of Transcription, *Tat. J. Biol Chem.* 1999, 274, 28837-28840.
27. Rana, T. M.; Jeang, K.-T. Biochemical and Functional Interactions between HIV-1 Tat Protein and TAR RNA. *Arch. Biochem Biophys.* 1999, 365, 175-185.
28. Gaczynska, M.; Osmulski, P. A. Targeting Protein-Protein Interactions in the Ubiquitin-Proteasome Pathway. in: Advances in Protein Chemistry and Structural Biology. Protein-Protein Interactions in Human Disease, Part A. Elsevier Inc.; Amsterdam, Netherlands, 2018, 123-65.
29. Schwarze, S. R.; Hruska, K. A.; Dowdy, S. F. Protein transduction: Unrestricted delivery into all cells? *Trends Cell Biol.* 2000, 10, 290-295.
30. Lata, S.; Mishra, R.; Banerjea, A. C. Proteasomal Degradation Machinery: Favorite Target of HIV-1 Proteins. *Front. Microbiol.* 2018, 9, 2738.
31. Kisselev, A. F.; Kaganovich, D.; Goldberg, A. L. Binding of hydrophobic peptides to several non-catalytic sites promotes peptide hydrolysis by all active sites of 20 S proteasomes-Evidence for peptide-induced channel opening in the alpha-rings. *J. Biol Chem.* 2002, 277, 22260-22270.
32. Tanaka, K.; Mizushima, T.; Saeki, Y. The proteasome: Molecular machinery and pathophysiological roles. *Biol Chem.* 2012, 393, 217-234.
33. Vakser, I. A. Long-distance potentials: An approach to the multiple-minima problem in ligand-receptor interaction. "*Protein Eng. Des. Sel.* 1996, 9, 37-41.
34. Vakser, I. A. Protein-Protein Docking: From Interaction to Interactome. *Biophys, J.* 2014, 107, 1785-1793.
35. Schrader, J.; Henneberg, F.; Mata, R. A.; Tittmann, K.; Schneider, T. R.; Stark, H. The inhibition mechanism of human 20S proteasomes enables next-generation inhibitor design. *Science* 2016, 353, 594-598.
36. Whitby, F. G.; Masters, E. I.; Kramer, L.; Knowlton, J. R.; Yao, Y.; Wang, C. C. Structural basis for the activation of 20S proteasomes by 11S regulators. *Nature* 2000, 408, 115-120.
37. Ortega, J.; Heymann, J. B.; Kajava, A. V.; Ustrell, V.; Rechsteiner, M.; Steven, A. C. The axial channel of the 20S proteasome opens upon binding of the PA200 activator. *J. Mol. Biol.* 2005, 346, 1221-1227.
38. Smith, D. M.; Chang, S.-C.; Park, S.; Finley, D.; Cheng, Y.; Goldberg, A. L. Docking of the proteasomal ATPases' carboxyl termini in the 20S proteasome's alpha ring opens the gate for substrate entry. *Mol. Cell.* 2007, 27, 731-744.
39. Giletto, M. B.; Osmulski, P. A.; Jones, C. L.; Gaczynska, M. E.; Tepe, J. J. Pipecolic esters as minimized templates for proteasome inhibition. *Org. Biomol Chem.* 2019, 17, 2734-2746.
40. Toste Rêgo, A.; da Fonseca, P. C. A. Characterization of Fully Recombinant Human 20S and 20S-PA200 Proteasome Complexes. *Mol. Cell* 2019, 76, 138-147.
41. Witkowska, J.; Giżyńska, M.; Grudnik, P.; Golik, P.; Karpowicz, P.; Gieldoń, A. Crystal structure of a low molecular weight activator Blm-pep with yeast 20S proteasome-insights into the enzyme activation mechanism. *Sci Rep.* 2017, 7, 6177.
42. Forster, A.; Whitby, F. G.; Hill, C. P. The pore of activated 20S proteasomes has an ordered 7-fold symmetric conformation. *EMBO J.* 2003, 22, 4356-4364.
43. Schweitzer, A.; Aufderheide, A.; Rudack, T.; Beck, F.; Pfeifer, G.; Plitzko, J. M. Structure of the human 26S proteasome at a resolution of 3.9 Å. *Proc. Natl. Acad. Sci.* 2016, 113, 7816-7821
44. Osmulski, P. A.; Gaczynska, M. Nanoenzymology of the 20S proteasome: Proteasomal actions are controlled by the allosteric transition. *Biochemistry.* 2002, 41, 7047-7053.
45. Osmulski, P. A.; Hochstrasser, M.; Gaczynska, M. A Tetrahedral Transition State at the Active Sites of the 20S Proteasome Is Coupled to Opening of the α-Ring Channel. *Structure.* 2009, 17, 1137-1147.
46. Dong, Y.; Zhang, S.; Wu, Z.; Li, X.; Wang, W. L.; Zhu, Y. Cryo-EM structures and dynamics of substrate-engaged human 26S proteasome. *Nature* 2019, 565, 49-55.
47. Gaczynska, M.; Osmulski, P. A. Harnessing proteasome dynamics and allostery in drug design. *Antioxidants Redox Signal.* 2014, 21, 2286-2301.
48. Wakata, A.; Lee, H.-M.; Rommel, P.; Toutchkine, A.; Schmidt, M.; Lawrence, D. S. Simultaneous Fluorescent Monitoring of Proteasomal Subunit Catalysis. *J. Am. Chem Soc.* 2010, 132, 1578-1582.
49. Asano, S.; Fukuda, Y.; Beck, F.; Aufderheide, A.; Forster, F.; Danev, R. A molecular census of 26S proteasomes in intact neurons. *Science* 2015, 347, 439-442.
50. Yoshimura, T.; Kameyama, K.; Takagi, T.; Ikai, A.; Tokunaga, F.; Koide, T. Molecular Characterization of the "26S" Proteasome Complex from Rat Liver. *J. Struct Biol.* 1993, 111, 200-211.
51. Tanahashi, N.; Murakami, Y.; Minami, Y.; Shimbara, N.; Hendil, K., B.; Tanaka, K. Hybrid Proteasomes. *J. Biol Chem.* 200, 275, 14336-14345.
52. Nunan, J.; Williamson, N. A.; Hill, A. F.; Sernee, M. F.; Masters, C. L.; Small, D. H. Proteasome-mediated degradation of the C-terminus of the Alzheimer's disease ?-amyloid protein precursor: Effect of C-terminal truncation on production of ?-amyloid protein. *J. Neurosci Res.* 2003, 74, 378-385.
53. Qing, H.; Zhou, W.; Christensen, M. A.; Sun, X.; Tong, Y.; Song, W. Degradation of BACE by the ubiquitin-proteasome pathway. *FASEB J.* 2004, 18, 1571-1573.
54. Osmulski, P. A.; Gaczynska, M. Rapamycin allosterically inhibits the proteasome. *Mol. Pharmacol.* 2013, 84, 104-113.
55. Schrodinger, L. L. C. *The AxPyMOL Molecular Graphics Plugin for Microsoft PowerPoint*, Version 1.5; 2015.
56. Schrodinger, L. L. C. *The JyMOL Molecular Graphics Development Component*, Version 1.5; 2015
57. Schrodinger, L. L. C. *The PyMOL Molecular Graphics System*, Version 1.5; 2015.

Example 3

Stability of Tat1 8,9 TOD and Tat-Den in Human Serum

Figure 17:
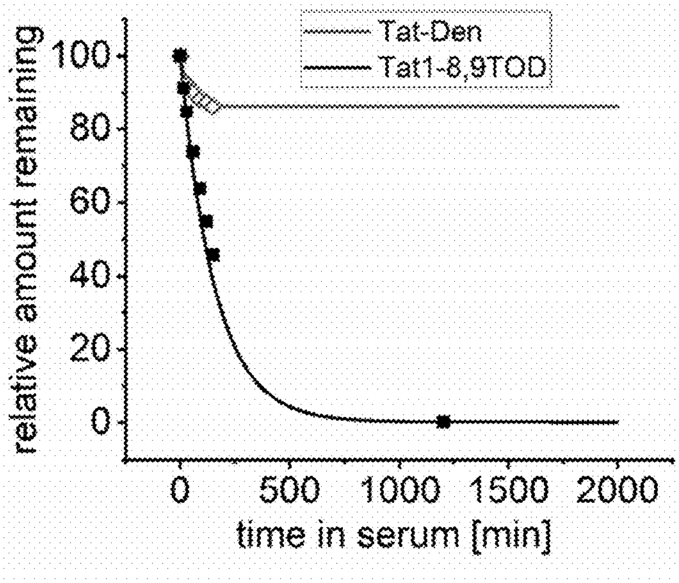
FIG. 17 shows the stability of Tat1 8,9, TOD and Tat-Den in human serum.

The half-life of Tat1 8,9 TOD in serum was about 2 hours (FIG. 17), which is comparable to many established drugs. In turn, Tat-Den was rapidly modified from triple-lysines to double-lysines, and the modified version was stable in serum. The modified Tat-Den (first metabolite) still activated both 20S and 26S human proteasomes. The fold activation was comparable with Tat-Den, however, maximum activation was reached at higher concentration (5 microM-10 microM) the original Tat-Den compound.

Example 4

Tat1 8,9 TOD Activates the 26S Proteasome

Figure 18:
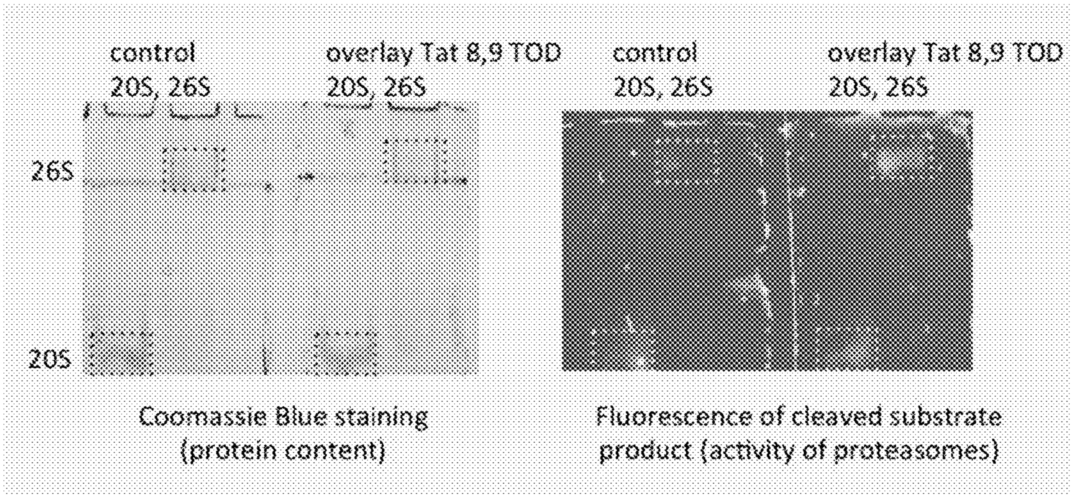
FIG. 18 shows purified human 20S and 26S proteasomes separated on non-denaturing polyacrylamide gel.
Figure 19:
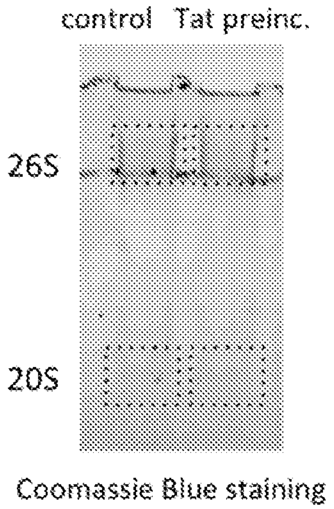
FIG. 19 shows a Coomassie-stained non-denaturing gel with 26S preparations separated after 15 min pre-incubation with the vehicle (DMSO) or 1 microM Tat1 8,9 TOD.

Purified human 20S and 26S proteasomes were separated on non-denaturing polyacrylamide gel. The gel was overlayed with reaction buffer containing 100 microM fluorogenic peptide substrate Suc-LLVY-MCA (SEQ ID NO: 14) and 1% of vehicle solvent (DMSO) or the substrate and 1 microM Tat1 8,9 TOD. The gel was photographed after 15 min of incubation and then stained for the total protein content with Coomassie Brilliant Blue, and photographed. FIG. 18 shows the total protein content on the left, and the proteasome activity on the right. The protein content was the same for the control and Tat-overlayed sets. The activities of both 26S and 20S are enhanced by Tat1 8,9 TOD. The enhanced activity of 26S was not the result of Tat1 8,9 TOD—induced breaking of the 26S assembly into its components (19S and 20S) and activation of the released 20S catalytic core that still remains in the gel together with the whole 26S assembly. FIG. 19 shows Coomassie-stained non-denaturing gel with 26S preparations separated after 15 min pre-incubation with the vehicle (DMSO) or 1 microM Tat1 8,9 TOD. Traces of the 20S in both control 26S preparation and preparation pre-incubated with Tat1 8,9 TOD.

Example 5

Small Peptide Based Compounds Activate the Proteasome and Attenuate Alzheimer's Disease Progression and Pathology The compounds were tested as follows: in neuroblast MC65 cell culture model with overexpressed C99 fragment of amyloid precursor protein (APP) upon tetracycline withdrawal or with external APP added; and in fruit fly (*D. melanogaster*) model of AD with overexpressed APP and BACE1. The compounds (1 μM) were mixed with food. Flies were trained to recognize "positive" and "negative" odors (olfaction aversion). The compounds were also treated in hAPP (J20) mice which overexpress a familial variant of APP. The compounds were injected for 14 days (1 mg/kg). Novel Object Recognition assay was used to test learning and memory.

The compounds were also tested in vitro with purified human housekeeping core proteasome, including competition of 1 μM mimetics with 1 μM peptide fragments of a face-docking Rpt subunits of 26S proteasome.

Single-molecule Atomic Force Microscopy (AFM) performed with native 20S particles.

Molecular docking studies were performed with Rhodium® (SwRI).

Figure 20:
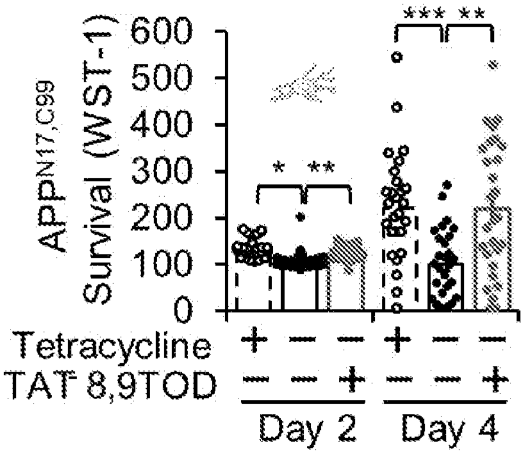
FIG. 20 shows 1 μM Tat-TOD improves survival of neuroblasts overexpressing APP.
Figure 21:
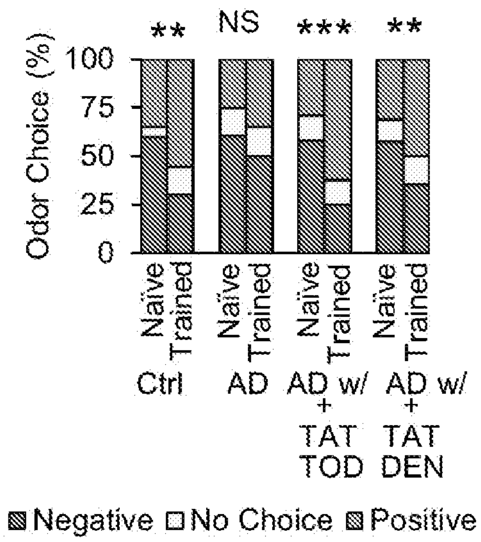
FIG. 21 shows in an AD-model that flies fed with TATs survive longer and learn to recognize odors as efficiently as controls. *p<0.01;p<0.001;* p<0.0001.
Figure 22:
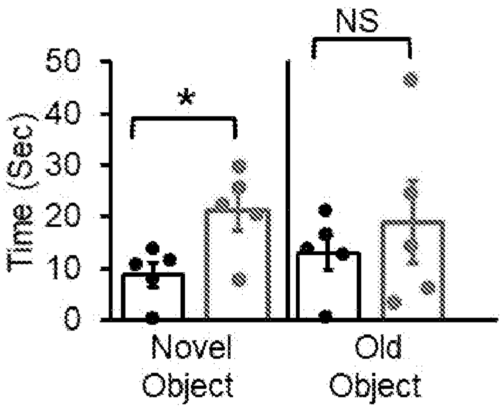
FIG. 22 shows in an AD-model that mice treated with Tat-TOD efficiently explore their surroundings to recognize novel objects.

The results are shown in FIGS. 20, 21, and 22. The data shows that specific activation of the proteasome with the compounds disclosed herein can attenuate and even reverse cognitive and metabolic symptoms of AD.

What is claimed is:

1. A compound having a structure

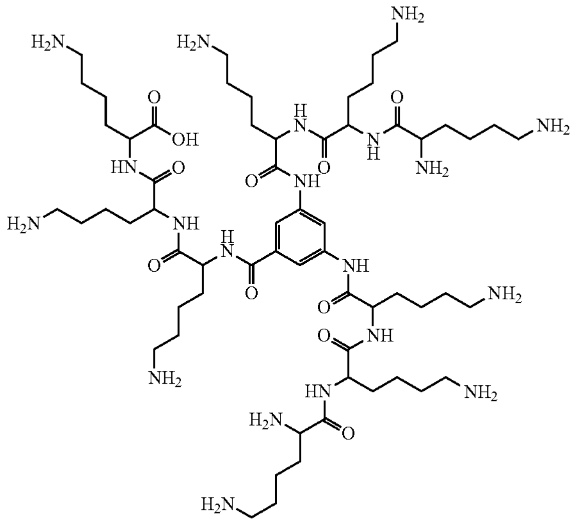 [SMILES: NCCCCC(N)C(=O)NC(CCCCN)C(=O)NC(CCCCN)C(=O)Nc1cc(NC(=O)C(CCCCN)NC(=O)C(CCCCN)NC(=O)C(N)CCCCN)cc(C(=O)NC(CCCCN)C(=O)NC(CCCCN)C(=O)NC(CCCCN)C(=O)O)c1]

or a pharmaceutically acceptable salt thereof.

2. A composition comprising the compound of claim 1, wherein the composition is formulated for intravenous, subcutaneous, or intranasal administration.

3. A pharmaceutical composition comprising a therapeutically effective amount of at least one compound of claim 1, or a pharmaceutically acceptable salt or solvate thereof; and a pharmaceutically acceptable carrier.

4. A method of increasing 20S or 26S proteasome activity in a subject, the method comprising administering to the subject with a disease a therapeutically effective amount of the compound of claim 1.

5. The method of claim 4, wherein the chymotrypsin-like activity of latent human 20S proteasome is activated.

6. The method of claim 4, wherein the disease is Alzheimer's disease.

7. A method of ameliorating one or more symptoms of Alzheimer's disease in a subject, the method comprising administering to the subject a therapeutically effective amount of the compound of claim 1.

8. The method of claim 7, wherein 20S or 26S proteasome activity is increased.

9. The method of claim 7, wherein the chymotrypsin-like activity of latent human 20S proteasome is activated.

10. The method of claim 7, wherein the subject has Alzheimer's disease.

11. A method of improving cognitive function in a subject, the method comprising administering to the subject a therapeutically effective amount of the compound of claim 1.

12. The method of claim 11, wherein the subject has or has been diagnosed with Alzheimer's disease.

* * * * *

SEQUENCE LISTING

```
<160> NUMBER OF SEQ ID NOS: 19

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Gly Arg Lys Lys Arg Arg Gln Arg Arg Arg Pro Ser
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Lys Asp Glu Gln Glu His Glu Phe Tyr Lys
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Tic-d-Oic

<400> SEQUENCE: 3
```

-continued

Gly Arg Lys Lys Arg Arg Gln Arg Pro Ser
1 5 10

<210> SEQ ID NO 4
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: alpha-aminoisobutyric acid

<400> SEQUENCE: 4

Gly Arg Lys Lys Arg Arg Gln Gly Arg Pro Ser
1 5 10

<210> SEQ ID NO 5
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: alpha-aminoisobutyric acid

<400> SEQUENCE: 5

Gly Arg Lys Lys Arg Arg Gln Gly Gln Arg Arg Lys Lys Arg Gly
1 5 10 15

<210> SEQ ID NO 6
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: 3,5-diaminobenzoic acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Lys Lys Lys Xaa Lys Lys Lys
1 5

<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

Gly Arg Lys Lys Arg Arg Gln Ala Ala Ala Pro Ser
1 5 10

<210> SEQ ID NO 8
<211> LENGTH: 7
<212> TYPE: PRT
<213> ORGANISM: Artificial Sequence
<220> FEATURE:
<223> OTHER INFORMATION: Synthetic construct -continued

<400> SEQUENCE: 8

Gly Arg Lys Lys Arg Arg Gln
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic construct

<400> SEQUENCE: 9

Arg Gln Arg Arg Arg Pro Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

Gln Glu Gly Thr Pro Glu Gly Leu Tyr Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Lys Asp Glu Gln Glu His Glu Phe Tyr Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct

<400> SEQUENCE: 12

Lys Lys Lys Ala Asn Leu Gln Tyr Tyr Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic construct

<400> SEQUENCE: 13

Lys Asn Met Ser Ile Lys Lys Leu Trp Lys
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: succinyl
<220> FEATURE:
<221> NAME/KEY: MISC_FEATURE
<222> LOCATION: (4)..(4)
<223> OTHER INFORMATION: 7-amino-4-methylcoumarin

<400> SEQUENCE: 14

Leu Leu Val Tyr
1

<210> SEQ ID NO 15
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-1,2,3,4-tetrahydroisoquinoline -3-carboxylic
      acid covalently attached to Octahydroindole-2-carboxylic acid
<220> FEATURE:
<221> NAME/KEY: MISC_FEATURE
<222> LOCATION: (4)..(4)
<223> OTHER INFORMATION: is covalently attached to Octahydroindole-2-
      carboxylic acid
<220> FEATURE:
<221> NAME/KEY: MISC_FEATURE
<222> LOCATION: (5)..(5)
<223> OTHER INFORMATION: Tic D-Oic is between residue 5 and residue 6

<400> SEQUENCE: 15

Gly Arg Lys Arg Gln Arg Pro Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Tic-Oic is between residue 3 and residue 4

<400> SEQUENCE: 16

Gly Arg Lys Arg Gln Arg Arg Arg Pro Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Tic-Oic is between residue 7 and 8

<400> SEQUENCE: 17

Gly Arg Lys Lys Arg Arg Gln Arg Pro Ser
1               5                   10

<210> SEQ ID NO 18
<211> LENGTH: 6
<212> TYPE: PRT
<213> ORGANISM: Artificial Sequence
<220> FEATURE:

-continued

```
<223> OTHER INFORMATION: Synthetic construct
<220> FEATURE:
<221> NAME/KEY: MISC_FEATURE
<222> LOCATION: (3)..(3)
<223> OTHER INFORMATION: Tic-Oic is between residues 3 and 4

<400> SEQUENCE: 18

Lys Lys Lys Lys Lys Lys
1               5


<210> SEQ ID NO 19
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Tic-Oic is between residues 3 and 4

<400> SEQUENCE: 19

Ala Ala Ala Ala Ala Ala
1               5
```